(12) United States Patent
Finch et al.

(10) Patent No.: US 11,939,353 B2
(45) Date of Patent: Mar. 26, 2024

(54) FLUORINATED AND ALKYLATED BILE ACIDS

(71) Applicant: Metselex, Inc., Minneapolis, MN (US)

(72) Inventors: Michael Finch, Minneapolis, MN (US); Cyrus B. Munshi, Blaine, MN (US); Cecilia M. P. Rodrigues, Lisbon (PT); Susana Dias Lucas de Oliveira, Sao Joao da Talha (PT)

(73) Assignee: Metselex, inc., Minneapolis, MN (US)

( * ) Notice: Subject to any disclaimer, the term of this patent is extended or adjusted under 35 U.S.C. 154(b) by 228 days.

(21) Appl. No.: 17/378,198

(22) Filed: Jul. 16, 2021

(65) Prior Publication Data

US 2022/0002339 A1 Jan. 6, 2022

Related U.S. Application Data

(62) Division of application No. 15/556,768, filed as application No. PCT/US2016/021809 on Mar. 10, 2016, now Pat. No. 11,072,630.

(60) Provisional application No. 62/141,506, filed on Apr. 1, 2015, provisional application No. 62/130,931, filed on Mar. 10, 2015.

(51) Int. Cl.
| | | |
|---|---|---|
| *A61K 31/025* | (2006.01) | |
| *C07J 9/00* | (2006.01) | |
| *C07J 41/00* | (2006.01) | |
| *C07J 51/00* | (2006.01) | |
| *C07J 63/00* | (2006.01) | |
| *B01J 37/26* | (2006.01) | |

(52) U.S. Cl.
CPC .............. *C07J 9/005* (2013.01); *A61K 31/025* (2013.01); *C07J 41/0061* (2013.01); *C07J 51/00* (2013.01); *C07J 63/008* (2013.01); *B01J 37/26* (2013.01); *C07C 2603/52* (2017.05)

(58) Field of Classification Search
CPC .......................... A61K 31/025; C07C 2603/52
See application file for complete search history.

(56) References Cited

U.S. PATENT DOCUMENTS

| | | | |
|---|---|---|---|
| 5,175,320 | A | 12/1992 | Pellicciari et al. |
| 11,072,630 | B2 * | 7/2021 | Finch .................... C07J 41/0061 |
| 2003/0130246 | A1 | 7/2003 | Bhat et al. |
| 2009/0258847 | A1 | 10/2009 | Schreiner et al. |
| 2014/0323748 | A1 | 10/2014 | Dosa et al. |
| 2014/0371190 | A1 | 12/2014 | Pellicciari |
| 2018/0044373 | A1 | 2/2018 | Finch et al. |

FOREIGN PATENT DOCUMENTS

| | | |
|---|---|---|
| EP | 0285285 A2 | 10/1988 |
| WO | WO-9401122 A1 | 1/1994 |
| WO | WO-2008071169 A2 | 6/2008 |
| WO | WO-2014036379 A2 | 3/2014 |
| WO | WO-2014154131 A1 | 10/2014 |
| WO | WO-2016045642 A1 | 3/2016 |
| WO | WO-2016145216 A1 | 9/2016 |

OTHER PUBLICATIONS

"U.S. Appl. No. 15/556,768, Advisory Action dated Dec. 31, 2020", 3 pgs.
"U.S. Appl. No. 15/556,768, Final Office Action dated Oct. 27, 2020", 8 pgs.
"U.S. Appl. No. 15/556,768, Non Final Office Action dated May 7, 2021", 8 pgs.
"U.S. Appl. No. 15/556,768, Non Final Office Action dated Jun. 15, 2020", 6 pgs.
"U.S. Appl. No. 15/556,768, Non Final Office Action dated Jul. 25, 2018", 6 pgs.
"U.S. Appl. No. 15/556,768, Notice of Allowance dated Jun. 8, 2021", 6 pgs.
"U.S. Appl. No. 15/556,768, Preliminary Amendment filed Sep. 8, 2017", 3 pgs.
"U.S. Appl. No. 15/556,768, Response filed Jan. 5, 2021 to Advisory Action dated Dec. 31, 2020".
"U.S. Appl. No. 15/556,768, Response filed Apr. 28, 2020 to Restriction Requirement dated Mar. 27, 2020", 18 pgs.
"U.S. Appl. No. 15/556,768, Response filed May 27, 2021 to Non Final Office Action dated May 7, 2021", 16 pgs.
"U.S. Appl. No. 15/556,768, Response filed Jun. 4, 2018 to Restriction Requirement dated May 3, 2018", 18 pgs.
"U.S. Appl. No. 15/556,768, Response filed Aug. 12, 2020 to Non Final Office Action dated Jun. 15, 2020", 21 pgs.
"U.S. Appl. No. 15/556,768, Response filed Sep. 24, 2018 to Non Final Office Action dated Jul. 25, 2018", 19 pgs.
"U.S. Appl. No. 15/556,768, Response filed Dec. 17, 2020 to Final Office Action dated Oct. 27, 2020", 17 pgs.
"U.S. Appl. No. 15/556,768, Restriction Requirement dated Mar. 27, 2020", 8 pgs.
"U.S. Appl. No. 15/556,768, Restriction Requirement dated May 3, 2018", 7 pgs.
"CAS Reg. No. 1486619-50-4; Entered STN".
"CAS Reg. No. 77-52-1; Entered STN", (Nov. 16, 1984).
"International Application Serial No. PCT/US2016/021809, International Search Report dated May 31, 2016", 3 pgs.
"International Application Serial No. PCT/US2016/021809, Written Opinion dated May 31, 2016", 7 pgs.
Macchiarulo, et al., "Molecular Field Analysis and 3D-Quantitative Structure—Activity Relationship Study (MFA 3D-QSAR) Unveil Novel Features of Bile Acid Recognition at TGR5", J. Chem. Inf. Model ,48(9) 1792-801, (Sep. 2008), 10 pgs.
Sievanen, et al., "1H, 13C, 19FNMR, and ESI mass spectral-characterization of two germinal difluorosteroids", Magn. Reson. Chem, 46(4), (2008), 392-97.
Une, et al., "Natural occurrence and chemical synthesis of bile alcohols, higher bile acids, and short side chain bile acids", Hiroshima J. Med. Sci, 43(2), (1994), 37-67.

\* cited by examiner

*Primary Examiner* — Theodore R. Howell

(74) *Attorney, Agent, or Firm* — Schwegman Lundberg & Woessner, P.A.

(57) ABSTRACT

The present invention relates to fluorinated and alkylated bile acids.

6 Claims, 5 Drawing Sheets

FLUORINATED AND ALKYLATED BILE ACIDS

This patent document pertains to the field of pharmaceutical molecules and specifically to fluorinated and alkylated versions of UDCA, TUDCA, as well as their analogs and derivatives for the treatment of diseases caused by tissue degeneration.

PRIORITY APPLICATIONS

This application is a divisional of U.S. patent application Ser. No. 15/556,768, filed Sep. 8, 2017, which is a U.S. National Stage Application filed under 35 U.S.C. § 371 from International Application Serial No. PCT/US2016/021809, filed on Mar. 10, 2016, and published as WO 2016/145216 on Sep. 15, 2016, which claims the benefit of priority to U.S. Provisional Application Ser. No. 62/130,931, filed on Mar. 10, 2015 and U.S. Provisional Application Ser. No. 62/141,506, filed on Apr. 1, 2015, which applications are incorporated herein by reference in their entireties.

BACKGROUND OF THE INVENTION

Neurodegenerative disorders such as Alzheimer's disease, Parkinson's disease, Amyotrophic lateral sclerosis and Huntington's disease are crippling disorders with poor prognosis and worsening progression over time. Existing therapies for the treatment of these disease states are of limited efficacy, and at best only attenuate the symptoms. The result is a steadily worsening of the quality of life for the patient accompanied by an increasing burden on the health care system.

Existing data indicates that bile acids confer a protective function on several disorders associated with tissue degeneration including those of the neurological system, diabetes, spinal cord injury, and ocular tissue. Bile acids, including ursodeoxycholic acid (UDCA) and tauroursodeoxycholic acid (TUDCA), inhibit tissue degeneration through a variety of mechanisms such as down-regulation of endoplasmic stress response elements (ERSE), blocking the Bax-induced perturbation of the cell membrane, and modulation of miRNA gene regulation.

BRIEF SUMMARY OF THE INVENTION

Described here in, inter alia, are compositions and preparations of fluorine derivatives of bile acids.

The invention provides in some embodiments a compound having formula (I):

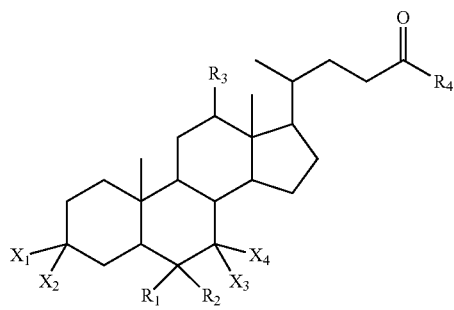

wherein
$R_1$ is —OH, —H—F, or —OP(O)(OH)$_2$;
$R_2$ is —OH, —H, —F, or —OP(O)(OH)$_2$;
$R_3$ is —OH, —H, —F or —OP(O)(OH)$_2$;
$R_4$ is —OH, —NH(CH$_2$)$_2$SO$_3$H, —NHCH$_2$COOH, —O—(CH$_2$)—O—P(O)(OH)$_2$, or —F;
$X_1$ is —F, —H, —O(CH$_3$), —O(C$_2$H$_5$), —OCH(CH$_3$)$_2$, —OH, or —OP(O)(OH)$_2$,
$X_2$ is —F, —OH, or —OP(O)(OH)$_2$;
$X_3$ is —F, —H, —O(CH$_3$), —O(C$_2$H$_5$), —OCH(CH$_3$)$_2$, —OH, or —OP(O)(OH)$_2$;
$X_4$ is —F or —OH, or —OP(O)(OH)$_2$;
or a compound having the formula (II):

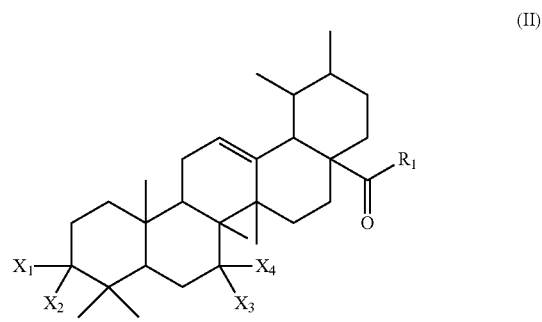

wherein
$R_1$ is —OH, —O—(CH$_2$)—O—P(O)(OH)$_2$, —OP(O)(OH)$_2$, or —F;
$X_1$ is —F, —H, —O(CH$_3$), —O(C$_2$H$_5$), —OCH(CH$_3$)$_2$, —OH, or —OP(O)(OH)$_2$;
$X_2$ is —F, —OH, or H;
$X_3$ is —F or —H, —O(CH$_3$), —O(C$_2$H$_5$), —(CH$_3$), —(C$_2$H$_5$), or —OCH(CH$_3$)$_2$; and
$X_4$ is —F or —H,
or a pharmaceutically acceptable salt thereof.

In the first aspect is a bile acid compound having the Formula (1):

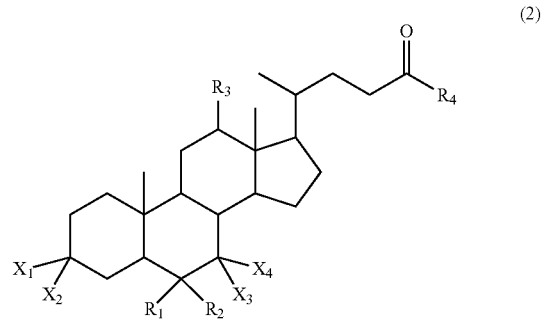

where $R_1$ is —OH or —H, $R_2$ is —OH or —H, $R_3$ is —OH, —H, —F or —OP(O)(OH)$_2$, $R_4$ is —OH, —NH(CH$_2$)$_2$SO$_3$H, —NHCH$_2$COOH, or —O—(CH$_2$)—O—P(O)(OH)$_2$; $X_1$ is —F or —H, $X_2$ is —F, —OH, —H or —OP(O)(OH)$_2$; $X_3$ is —F or —H, $X_4$ is —F or —OH, —H or —OP(O)(OH)$_2$.

In one aspect Formula (1) represents a tetrafluoro compound where $X_1$, $X_2$, $X_3$ and $X_4$ are all —F.

In another aspect the Formula (1) represents a trifluoro compound where $X_1$ is —F, $X_2$ is —F, $X_3$ is —F, and $X_4$ is —OP(O)(OH)$_2$.

In another aspect the Formula (1) represents a trifluoro compound where $X_1$ is —F, $X_2$ is —OH, $X_3$ is —F, and $X_4$ is —F.

In another aspect the Formula (1) represents a trifluoro compound where $X_1$ is —F, $X_2$ is —OP(O)(OH)$_2$, $X_3$ is —F, and $X_4$ is —F.

In another aspect the Formula (1) represents a trifluoro compound where $X_1$ is —F, $X_2$ is —H, $X_3$ is —F, and $X_4$ is —F.

In another aspect the Formula (1) represents a trifluoro compound where $X_1$ is —F, $X_2$ is —F, $X_3$ is —F, and $X_4$ is —OH.

In another aspect the Formula (1) represents a trifluoro compound where $X_1$ is —F, $X_2$ is —F, $X_3$ is —F, and $X_4$ is —OP(O)(OH)$_2$.

In another aspect the Formula (1) represents a trifluoro compound where $X_1$ is —F, $X_2$ is —F, $X_3$ is —F, and $X_4$ is —H.

In another aspect Formula (1) represents a difluoro compound where $X_1$ is —H, $X_2$ is —F, $X_3$ is —H, and $X_4$ is —OH.

In another aspect the Formula (1) represents a difluoro compound where $X_1$ is —F, $X_2$ is —F, $X_3$ is —H, and $X_4$ is —OP(O)(OH)$_2$.

In another aspect the Formula (1) represents a difluoro compound where $X_1$ is —F, $X_2$ is —F, $X_3$ is —H, and $X_4$ is —H.

In another aspect the Formula (1) represents a difluoro compound where $X_1$ is —F, $X_2$ is —OH, $X_3$ is —F, and $X_4$ is —OP(O)(OH)$_2$.

In another aspect the Formula (1) represents a difluoro compound where $X_1$ is —F, $X_2$ is —OP(O)(OH)$_2$, $X_3$ is —F, and $X_4$ is —OP(O)(OH)$_2$.

In another aspect the Formula (1) represents a difluoro compound where $X_1$ is —F, $X_2$ is —H, $X_3$ is —F, and $X_4$ is —OP(O)(OH)$_2$. In another aspect the Formula (1) represents a difluoro compound where $X_1$ is —F, $X_2$ is —OH, $X_3$ is —H, and $X_4$ is —F.

In another aspect the Formula (1) represents a difluoro compound where $X_1$ is —F, $X_2$ is —OP(O)(OH)$_2$, $X_3$ is —H, and $X_4$ is —F.

In another aspect the Formula (1) represents a difluoro compound where $X_1$ is —F, $X_2$ is —H, $X_3$ is —H, and $X_4$ is —F.

In another aspect the Formula (1) represents a difluoro compound where $X_1$ is —H, $X_2$ is —OH, $X_3$ is —F, and $X_4$ is —F.

In another aspect the Formula (1) represents a difluoro compound where $X_1$ is —H, $X_2$ is —OP(O)(OH)$_2$, $X_3$ is —F, and $X_4$ is —F.

In another aspect the Formula (1) represents a difluoro compound where $X_1$ is —H, $X_2$ is —H, $X_3$ is —F, and $X_4$ is —F.

In another aspect Formula (1) represents a monofluoro compound where $X_1$ is —F, $X_2$ is-OH, $X_3$ is —H and $X_4$ is —OH.

In another aspect Formula (1) represents a monofluoro compound where $X_1$ is —F, $X_2$ is —OP(O)(OH)$_2$, $X_3$ is —H and $X_4$ is —OH.

In another aspect Formula (1) represents a monofluoro compound where $X_1$ is —F, $X_2$ is-H, $X_3$ is —H and $X_4$ is —OH.

In another aspect Formula (1) represents a monofluoro compound where $X_1$ is —F, $X_2$ is-OH, $X_3$ is —H and $X_4$ is —OP(O)(OH)$_2$.

In another aspect Formula (1) represents a monofluoro compound where $X_1$ is —F, $X_2$ is —OP(O)(OH)$_2$, $X_3$ is —H and $X_4$ is —OP(O)(OH)$_2$.

In another aspect Formula (1) represents a monofluoro compound where $X_1$ is —F, $X_2$ is-H, $X_3$ is —H and $X_4$ is —OP(O)(OH)$_2$.

In another aspect Formula (1) represents a monofluoro compound where $X_1$ is —F, $X_2$ is-OH, $X_3$ is —H and $X_4$ is —H.

In another aspect Formula (1) represents a monofluoro compound where $X_1$ is —F, $X_2$ is —OP(O)(OH)$_2$, $X_3$ is —H and $X_4$ is —H.

In another aspect Formula (1) represents a monofluoro compound where $X_1$ is —F, $X_2$ is —H, $X_3$ is —H and $X_4$ is —H.

In another aspect Formula (1) represents a monofluoro compound where $X_1$ is —H, $X_2$ is-F, $X_3$ is —H and $X_4$ is —OH.

In another aspect Formula (1) represents a monofluoro compound where $X_1$ is —H, $X_2$ is-F, $X_3$ is —H and $X_4$ is —OP(O)(OH)$_2$.

In another aspect Formula (1) represents a monofluoro compound where $X_1$ is —H, $X_2$ is-F, $X_3$ is —H and $X_4$ is —H.

In another aspect Formula (1) represents a monofluoro compound where $X_1$ is —H, $X_2$ is-OH, $X_3$ is —F and $X_4$ is —OH.

In another aspect Formula (1) represents a monofluoro compound where $X_1$ is —H, $X_2$ is-OH, $X_3$ is —F and $X_4$ is —OP(O)(OH)$_2$.

In another aspect Formula (1) represents a monofluoro compound where $X_1$ is —H, $X_2$ is-OH, $X_3$ is —F and $X_4$ is —H.

In another aspect Formula (1) represents a monofluoro compound where $X_1$ is —H, $X_2$ is —OP(O)(OH)$_2$, $X_3$ is —F and $X_4$ is —OH.

In another aspect Formula (1) represents a monofluoro compound where $X_1$ is —H, $X_2$ is —OP(O)(OH)$_2$, $X_3$ is —F and $X_4$ is —OP(O)(OH)$_2$.

In another aspect Formula (1) represents a monofluoro compound where $X_1$ is —H, $X_2$ is —OP(O)(OH)$_2$, $X_3$ is —F and $X_4$ is —H.

In another aspect Formula (1) represents a monofluoro compound where $X_1$ is —H, $X_2$ is-H, $X_3$ is —F and $X_4$ is —OH.

In another aspect Formula (1) represents a monofluoro compound where $X_1$ is —H, $X_2$ is-H, $X_3$ is —F and $X_4$ is —OP(O)(OH)$_2$.

In another aspect Formula (1) represents a monofluoro compound where $X_1$ is —H, $X_2$ is-H, $X_3$ is —F and $X_4$ is —H.

In another aspect Formula (1) represents a monofluoro compound where $X_1$ is —H, $X_2$ is-OH, $X_3$ is —H and $X_4$ is —F.

In another aspect Formula (1) represents a monofluoro compound where $X_1$ is —H, $X_2$ is —OP(O)(OH)$_2$, $X_3$ is —H and $X_4$ is —F.

In another aspect Formula (1) represents a monofluoro compound where $X_1$ is —H, $X_2$ is —H, $X_3$ is —H and $X_4$ is —F.

In another aspect is a bile acid having the Formula (1'):

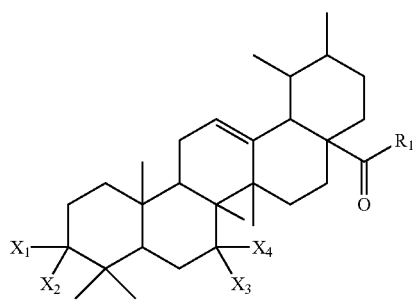

(1')

where $R_1$ is —OH or —O—(CH$_2$)—O—P(O)(OH)$_2$ or —OP(O)(OH)$_2$; $X_1$ is —F or —H; $X_2$ is —F or —OH, or —OP(O)(OH)$_2$ or —H; $X_3$ is —F or —H; and $X_4$ is —F or —H.

In one aspect Formula (1') represents a tetrafluoro compound where $X_1$, $X_2$, $X_3$, $X_4$ are all —F.

In another aspect Formula (1') represents a trifluoro compound where $X_1$ is —F, $X_2$-is —F, $X_3$ is —F and $X_4$ is —H In another aspect Formula (1') represents a trifluoro compound where $X_1$ is —F, $X_2$-is —F, $X_3$ is —H and $X_4$ is —F In another aspect Formula (1') represents a trifluoro compound where $X_1$ is —F, $X_2$-is —OH, $X_3$ is —F and $X_4$ is —F.

In another aspect Formula (1') represents a trifluoro compound where $X_1$ is —F, $X_2$-is —OP(O)(OH)$_2$, $X_3$ is —F and $X_4$ is —F.

In another aspect Formula (1') represents a trifluoro compound where $X_1$ is —F, $X_2$-is —H, $X_3$ is —F and $X_4$ is —F.

In another aspect Formula (1') represents a difluoro compound where $X_1$ is —F, $X_2$ is —F, $X_3$ is —H, and $X_4$ is —H.

In another aspect Formula (1') represents a difluoro compound where $X_1$ is —F, $X_2$ is —OH, $X_3$ is —F, and $X_4$ is —H.

In another aspect Formula (1') represents a difluoro compound where $X_1$ is —F, $X_2$ is —OP(O)(OH)$_2$, $X_3$ is —F, and $X_4$ is —H.

In another aspect Formula (1') represents a difluoro compound where $X_1$ is —F, $X_2$ is —H, $X_3$ is —F, and $X_4$ is —H.

In another aspect Formula (1') represents a difluoro compound where $X_1$ is —F, $X_2$ is —OH, $X_3$ is —H, and $X_4$ is —F.

In another aspect Formula (1') represents a difluoro compound where $X_1$ is —F, $X_2$ is —OP(O)(OH)$_2$, $X_3$ is —H, and $X_4$ is —F.

In another aspect Formula (1') represents a difluoro compound where $X_1$ is —F, $X_2$ is —H, $X_3$ is —H, and $X_4$ is —F.

In another aspect Formula (1') represents a difluoro compound where $X_1$ is —H, $X_2$ is —F, $X_3$ is —F, and $X_4$ is —H.

In another aspect Formula (1') represents a difluoro compound where $X_1$ is —H, $X_2$ is —F, $X_3$ is —H, and $X_4$ is —F.

In another aspect Formula (1') represents a difluoro compound where $X_1$ is —H, $X_2$ is —OH, $X_3$ is —F, and $X_4$ is —F.

In another aspect Formula (1') represents a difluoro compound where $X_1$ is —H, $X_2$ is —OP(O)(OH)$_2$, $X_3$ is —F, and $X_4$ is —F.

In another aspect Formula (1') represents a difluoro compound where $X_1$ is —H, $X_2$ is —H, $X_3$ is —F, and $X_4$ is —F.

In another aspect is a bile acid compound having the Formula (2):

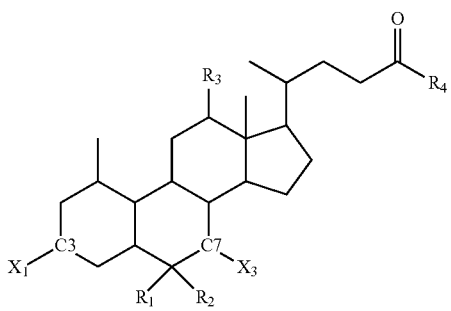

(2)

where $R_1$ is —OH or —H or —OP(O)(OH)$_2$; $R_2$ is —OH or —H or —OP(O)(OH)$_2$; $R_3$ is —OH, —H, or —OP(O)(OH)$_2$; $R_4$ is —OH, —NH(CH$_2$)$_2$SO$_3$H, —NHCH$_2$COOH, or —O—(CH$_2$)—O—P(O)(OH)$_2$; $X_1$ is —O(CH$_3$) or —O(C$_2$H$_5$) or —OCH(CH$_3$)$_2$ or —H or —OH or —OP(O)(OH)$_2$; $X_3$ is —O(CH$_3$) or —O(C$_2$H$_5$), or —CH(CH$_3$)$_2$ or —OH, or —H or —OP(O)(OH)$_2$. Carbon positions 3 and 7 are identified in Formula (I) above.

In one aspect of the Formula (2) $X_1$ is —O(CH$_3$) and $X_2$ is —O(CH$_3$) or —O(C$_2$H$_5$), or —CH(CH$_3$)$_2$ or —OH, —H or —OP(O)(OH)$_2$.

In another aspect of the Formula (2), $X_1$ is —O(C$_2$H$_5$) and $X_2$ is —O(CH$_3$) or —O(C$_2$H$_5$) or —CH(CH$_3$)$_2$ or —OH or —H or —OP(O)(OH)$_2$.

In one aspect of the Formula (2) $X_1$ is —OCH(CH$_3$)$_2$ and $X_3$ is —O(CH$_3$) or —O(C$_2$H$_5$), or —CH(CH$_3$)$_2$ or —OH or —H or —OP(O)(OH)$_2$.

In another aspect of the Formula (2), $X_1$ is —OH and $X_3$ is —O(CH$_3$) or —O(C$_2$H$_5$) or —CH(CH$_3$)$_2$.

In another aspect of the Formula (2), $X_1$ is —H and $X_3$ is —O(CH$_3$) or —O(C$_2$H$_5$), or —CH(CH$_3$)$_2$.

In another aspect of the Formula (2), $X_1$ is —OP(O)(OH)$_2$ and $X_3$ is —O(CH$_3$) or —O(C$_2$H$_5$) or —CH(CH$_3$)$_2$.

In another aspect of the Formula (2) $X_1$ is —O(CH$_3$) or —O(C$_2$H$_5$) or —H or —OH or OP(O)(OH)$_2$ and $X_3$ is —O(CH$_3$).

In another aspect of the Formula (2) $X_1$ is —O(CH$_3$) or —O(C$_2$H$_5$) or —H or —OH or OP(O)(OH)$_2$ and $X_3$ is —O(C$_2$H$_5$).

In another aspect of the Formula (2) $X_1$ is —O(CH$_3$) or —O(C$_2$H$_5$) or —H or —OH or OP(O)(OH)$_2$ and $X_3$ is —OCH(CH$_3$)$_2$.

In another aspect of the Formula (2) $X_1$ is —O(CH$_3$) or —O(C$_2$H$_5$) and $X_3$ is —OH.

In another aspect of the Formula (2) $X_1$ is —O(CH$_3$) or —O(C$_2$H$_5$) and $X_3$ is —H.

In another aspect of the Formula (2) $X_1$ is —O(CH$_3$) or —O(C$_2$H$_5$) and $X_3$ is —OP(O)(OH)$_2$.

In another aspect of the Formula (2), if both $R_1$ and $R_2$ are —H, then only either $X_1$ or $X_3$ are —OH, but not both.

In another aspect of the Formula (2) at least one of the groups $X_1$ or $X_3$ contains a carbon atom.

In another aspect of the Formula (2) at least one of the $X_1$ or $X_3$ groups are alkylated.

In another aspect of the Formula (2) at least one of the $X_1$ or $X_3$ groups are O-alkylated.

In another aspect is a bile acid having the Formula (2'):

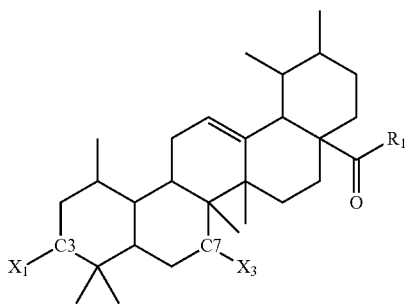

(2)

where $R_1$ is —OH or —O—$(CH_2)$—O—P(O)$(OH)_2$ or —OP(O)$(OH)_2$; $X_1$ is —O$(CH_3)$ or —O$(C_2H_5)$ or —OCH$(CH_3)_2$ or —OH or —H or —OP(O)$(OH)_2$; $X_3$ is —O$(CH_3)$ or —O$(C_2H_5)$ or —$(CH_3)$ or —$(C_2H_5)$ or —OCH$(CH_3)_2$. Carbons 3 and 7 are identified in Formula (2') above.

In one aspect of the Formula (2') $X_1$ is —O$(CH_3)$ and $X_3$ is —O$(CH_3)$ or —O$(C_2H_5)$ or —$(CH_3)$ or —$(C_2H_5)$ or —OCH$(CH_3)_2$.

In another aspect of the Formula (2') $X_1$ is —O$(C_2H_5)$ and $X_3$ is —O$(CH_3)$ or —O$(C_2H_5)$ or —$(CH_3)$ or —$(C_2H_5)$ or —OCH$(CH_3)_2$.

In another aspect of the Formula (2') $X_1$ is —OCH$(CH_3)_2$ and $X_3$ is —O$(CH_3)$ or —O$(C_2H_5)$ or —$(CH_3)$ or —$(C_2H_5)$ or —OCH$(CH_3)_2$.

In another aspect of the Formula (2') $X_1$ is —OH and $X_3$ is —O$(CH_3)$ or —O$(C_2H_5)$ or —$(CH_3)$ or —$(C_2H_5)$ or —OCH$(CH_3)_2$.

In another aspect of the Formula (2') $X_1$ is —H and $X_3$ is —O$(CH_3)$ or —O$(C_2H_5)$ or —$(CH_3)$ or —$(C_2H_5)$ or —OCH$(CH_3)_2$.

In another aspect of the Formula (2') $X_1$ is —OP(O)$(OH)_2$ and $X_3$ is —O$(CH_3)$ or —O$(C_2H_5)$ or —$(CH_3)$ or —$(C_2H_5)$ or —OCH$(CH_3)_2$.

In another aspect of the Formula (2') $X_1$ is —O$(CH_3)$ or —O$(C_2H_5)$ or —OCH$(CH_3)_2$ or —OH or —H or —OP(O)$(OH)_2$ and $X_3$ is —O$(CH_3)$.

In another aspect of the Formula (2') $X_1$ is —O$(CH_3)$ or —O$(C_2H_5)$ or —OCH$(CH_3)_2$ or —OH or —H or —OP(O)$(OH)_2$ and $X_3$ is —O$(C_2H_5)$.

In another aspect of the Formula (2') $X_1$ is —O$(CH_3)$ or —O$(C_2H_5)$ or —OCH$(CH_3)_2$ or —OH or —H or —OP(O)$(OH)_2$ and $X_3$ is —$(CH_3)$.

In another aspect of the Formula (2') $X_1$ is —O$(CH_3)$ or —O$(C_2H_5)$ or —OCH$(CH_3)_2$ or —OH or —H or —OP(O)$(OH)_2$ and $X_3$ is —O$(C_2H_5)$.

In another aspect of the Formula (2') $X_1$ is —O$(CH_3)$ or —O$(C_2H_5)$ or —OCH$(CH_3)_2$ or - and $X_2$ is —H.

In another aspect of the Formula (2') $X_1$ is —O$(CH_3)$ or —O$(C_2H_5)$ or —OCH$(CH_3)_2$ and $X_3$ is —OH.

In another aspect of the Formula (2') $X_1$ is —O$(CH_3)$ or —O$(C_2H_5)$ or —OCH$(CH_3)_2$ H or and $X_3$ is —OP(O)(OH) $_2$.

In another aspect of the Formula (2') at least one of the groups $X_1$ and $X_3$ contains a carbon atom.

In another aspect of the Formula (2') at least one of the $X_1$ or $X_3$ groups are alkylated.

In another aspect of the Formula (2') at least one of the $X_1$ or $X_3$ groups are O-alkylated.

In another aspect is a pharmaceutical composition consists of pharmacologically active and acceptable excipient including compounds (1), (1'), and fluorine-substituted embodiments thereof, and (2), (2'), and alkyl-substituted embodiments thereof.

In another aspect is a method of treating or preventing neurodegenerative disorders, diabetes, eye disorders, or metabolic disease in a subject thereof.

DETAILED DESCRIPTION OF THE INVENTION

Fluorinated Bile Acids

Figure 1:
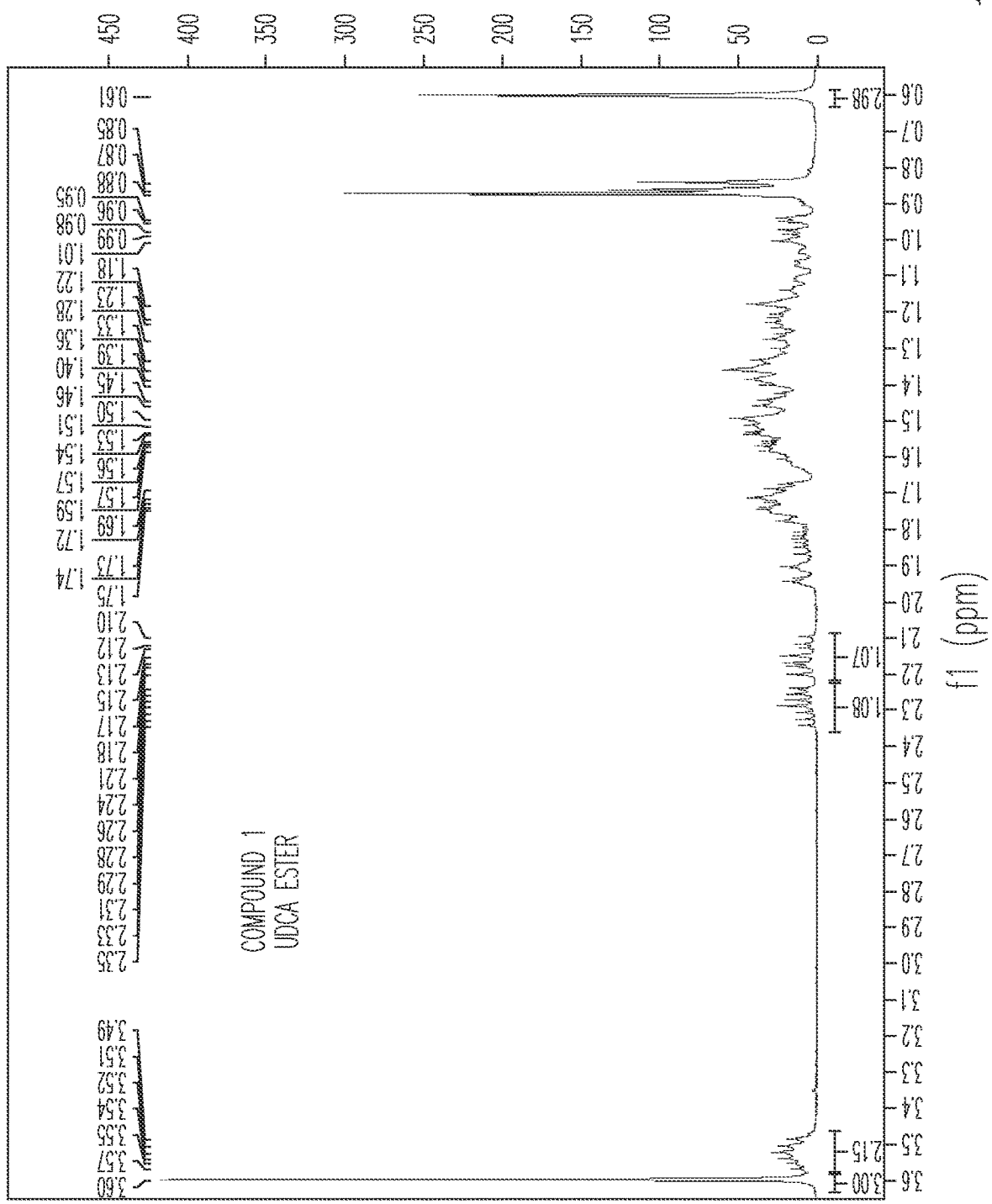
FIG. 1. $^1$H-NMR-Compound 1.

The replacement of the hydrogen or hydroxyl in pharmaceutically-active molecules with fluorine may confer several benefits, among them being metabolic stability, binding affinity, and bioavailability. Further, fluorine substitutions may exert only minor steric hindrances on receptors, proteins, antibodies, or biologic macromolecules, and hence fluorination of pharmaceuticals may be well tolerated. With a van der Walls radius of only 1.47 Angstroms, fluorine is considerably smaller than many of the commonly targeted substituents. Described herein are examples of fluorinated bile acids. Fluorination was conducted at random sites along the bile acid molecules since the metabolic active sites of these molecules is unknown.

As used herein, "pharmaceutically acceptable salts" refers to derivatives of the disclosed compounds where the parent compound is modified by converting an existing acid or base moiety into its salt form. Examples of pharmaceutically acceptable salts include, but are not limited to, mineral or organic acid salts of basic residues such as amines; alkali or organic salts of acidic residues such as carboxylic acids; and the like. Pharmaceutically acceptable salts of the present invention include the conventional non-toxic salts or the quaternary ammonium salts of the parent compound formed, for example, from non-toxic inorganic or organic acids. Pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two.

As used herein, "prodrugs" refer to any covalently bonded carriers which release the active parent drug when administered to a subject. Prodrugs can be prepared by modifying functional groups present in the compounds in such a way that the modifications are cleaved, either in routine manipulation or in vivo, to the parent compounds.

In one aspect is a compound having the formula (1), wherein, (1)

or a pharmaceutically acceptable salt thereof.

In the compound of formula (1) $R_1$ is —OH or —H, $R_2$ is —OH or —H, $R_3$ is —OH, —H, —F or —OP(O)(OH)$_2$, $R_4$ is —OH, —NH(CH$_2$)$_2$SO$_3$H, —NHCH$_2$COOH, or —O—(CH$_2$)—O—P(O)(OH)$_2$; $X_1$ is —F or —H, $X_2$ is —F, —OH, —H or —OP(O)(OH)$_2$; $X_3$ is —F or —H, $X_4$ is —F or —OH, —H or —OP(O)(OH)$_2$.

In one aspect Formula (1) represents a tetrafluoro compound where $X_1$, $X_2$, $X_3$ and $X_4$ are all —F.

In another aspect the Formula (1) represents a trifluoro compound where $X_1$ is —F, $X_2$ is —F, $X_3$ is —F, and $X_4$ is —OP(O)(OH)$_2$.

In another aspect the Formula (1) represents a trifluoro compound where $X_1$ is —F, $X_2$ is —OH, $X_3$ is —F, and $X_4$ is —F.

In another aspect the Formula (1) represents a trifluoro compound where $X_1$ is —F, $X_2$ is —OP(O)(OH)$_2$, $X_3$ is —F, and $X_4$ is —F.

In another aspect the Formula (1) represents a trifluoro compound where $X_1$ is —F, $X_2$ is —H, $X_3$ is —F, and $X_4$ is —F.

In another aspect the Formula (1) represents a trifluoro compound where $X_1$ is —F, $X_2$ is —F, $X_3$ is —F, and $X_4$ is —OH.

In another aspect the Formula (1) represents a trifluoro compound where $X_1$ is —F, $X_2$ is —F, $X_3$ is —F, and $X_4$ is —OP(O)(OH)$_2$.

In another aspect the Formula (1) represents a trifluoro compound where $X_1$ is —F, $X_2$ is —F, $X_3$ is —F, and $X_4$ is —H.

In another aspect Formula (1) represents a difluoro compound where $X_1$ is —H, $X_2$ is —F, $X_3$ is —H, and $X_4$ is —OH.

In another aspect the Formula (1) represents a difluoro compound where $X_1$ is —F, $X_2$ is —F, $X_3$ is —H, and $X_4$ is —OP(O)(OH)$_2$.

In another aspect the Formula (1) represents a difluoro compound where $X_1$ is —F, $X_2$ is —F, $X_3$ is —H, and $X_4$ is —H.

In another aspect the Formula (1) represents a difluoro compound where $X_1$ is —F, $X_2$ is —OH, $X_3$ is —F, and $X_4$ is —OP(O)(OH)$_2$.

In another aspect the Formula (1) represents a difluoro compound where $X_1$ is —F, $X_2$ is —OP(O)(OH)$_2$, $X_3$ is —F, and $X_4$ is —OP(O)(OH)$_2$.

In another aspect the Formula (1) represents a difluoro compound where $X_1$ is —F, $X_2$ is —H, $X_3$ is —F, and $X_4$ is —OP(O)(OH)$_2$. In another aspect the Formula (1) represents a difluoro compound where $X_1$ is —F, $X_2$ is —OH, $X_3$ is —H, and $X_4$ is —F.

In another aspect the Formula (1) represents a difluoro compound where $X_1$ is —F, $X_2$ is —OP(O)(OH)$_2$, $X_3$ is —H, and $X_4$ is —F.

In another aspect the Formula (1) represents a difluoro compound where $X_1$ is —F, $X_2$ is —H, $X_3$ is —H, and $X_4$ is —F.

In another aspect the Formula (1) represents a difluoro compound where $X_1$ is —H, $X_2$ is —OH, $X_3$ is —F, and $X_4$ is —F.

In another aspect the Formula (1) represents a difluoro compound where $X_1$ is —H, $X_2$ is —OP(O)(OH)$_2$, $X_3$ is —F, and $X_4$ is —F.

In another aspect the Formula (1) represents a difluoro compound where $X_1$ is —H, $X_2$ is —H, $X_3$ is —F, and $X_4$ is —F.

In another aspect Formula (1) represents a monofluoro compound where $X_1$ is —F, $X_2$ is-OH, $X_3$ is —H and $X_4$ is —OH.

In another aspect Formula (1) represents a monofluoro compound where $X_1$ is —F, $X_2$ is-OP(O)(OH)$_2$, $X_3$ is —H and $X_4$ is —OH.

In another aspect Formula (1) represents a monofluoro compound where $X_1$ is —F, $X_2$ is-H, $X_3$ is —H and $X_4$ is —OH.

In another aspect Formula (1) represents a monofluoro compound where $X_1$ is —F, $X_2$ is-OH, $X_3$ is —H and $X_4$ is —OP(O)(OH)$_2$.

In another aspect Formula (1) represents a monofluoro compound where $X_1$ is —F, $X_2$ is-OP(O)(OH)$_2$, $X_3$ is —H and $X_4$ is —OP(O)(OH)$_2$.

In another aspect Formula (1) represents a monofluoro compound where $X_1$ is —F, $X_2$ is-H, $X_3$ is —H and $X_4$ is —OP(O)(OH)$_2$.

In another aspect Formula (1) represents a monofluoro compound where $X_1$ is —F, $X_2$ is-OH, $X_3$ is —H and $X_4$ is —H.

In another aspect Formula (1) represents a monofluoro compound where $X_1$ is —F, $X_2$ is —OP(O)(OH)$_2$, $X_3$ is —H and $X_4$ is —H.

In another aspect Formula (1) represents a monofluoro compound where $X_1$ is —F, $X_2$ is —H, $X_3$ is —H and $X_4$ is —H.

In another aspect Formula (1) represents a monofluoro compound where $X_1$ is —H, $X_2$ is-F, $X_3$ is —H and $X_4$ is —OH.

In another aspect Formula (1) represents a monofluoro compound where $X_1$ is —H, $X_2$ is-F, $X_3$ is —H and $X_4$ is —OP(O)(OH)$_2$.

In another aspect Formula (1) represents a monofluoro compound where $X_1$ is —H, $X_2$ is-F, $X_3$ is —H and $X_4$ is —H.

In another aspect Formula (1) represents a monofluoro compound where $X_1$ is —H, $X_2$ is-OH, $X_3$ is —F and $X_4$ is —OH.

In another aspect Formula (1) represents a monofluoro compound where $X_1$ is —H, $X_2$ is-OH, $X_3$ is —F and $X_4$ is —OP(O)(OH)$_2$.

In another aspect Formula (1) represents a monofluoro compound where $X_1$ is —H, $X_2$ is-OH, $X_3$ is —F and $X_4$ is —H.

In another aspect Formula (1) represents a monofluoro compound where $X_1$ is —H, $X_2$ is-OP(O)(OH)$_2$, $X_3$ is —F and $X_4$ is —OH.

In another aspect Formula (1) represents a monofluoro compound where $X_1$ is —H, $X_2$ is-OP(O)(OH)$_2$, $X_3$ is —F and $X_4$ is —OP(O)(OH)$_2$.

In another aspect Formula (1) represents a monofluoro compound where $X_1$ is —H, $X_2$ is-OP(O)(OH)$_2$, $X_3$ is —F and $X_4$ is —H.

In another aspect Formula (1) represents a monofluoro compound where $X_1$ is —H, $X_2$ is-H, $X_3$ is —F and $X_4$ is —OH.

In another aspect Formula (1) represents a monofluoro compound where $X_1$ is —H, $X_2$ is-H, $X_3$ is —F and $X_4$ is —OP(O)(OH)$_2$.

In another aspect Formula (1) represents a monofluoro compound where $X_1$ is —H, $X_2$ is-H, $X_3$ is —F and $X_4$ is —H.

In another aspect Formula (1) represents a monofluoro compound where $X_1$ is —H, $X_2$ is-OH, $X_3$ is —H and $X_4$ is —F.

In another aspect Formula (1) represents a monofluoro compound where $X_1$ is —H, $X_2$ is —OP(O)(OH)$_2$, $X_3$ is —H and $X_4$ is —F.

In another aspect Formula (1) represents a monofluoro compound where $X_1$ is —H, $X_2$ is —H, $X_3$ is —H and $X_4$ is —F.

Preferably the compound of formula (1) is a tetrafluoro compound and may have the formulae:

(1.1)

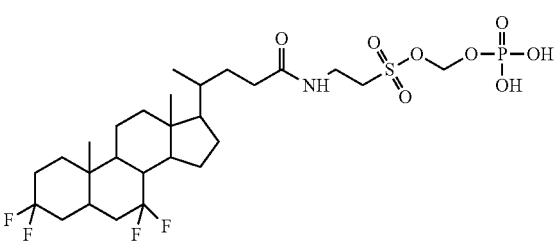

(1.2)

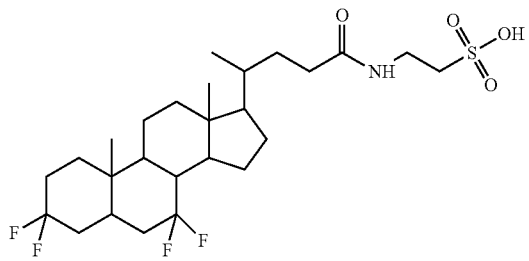

(1.3)

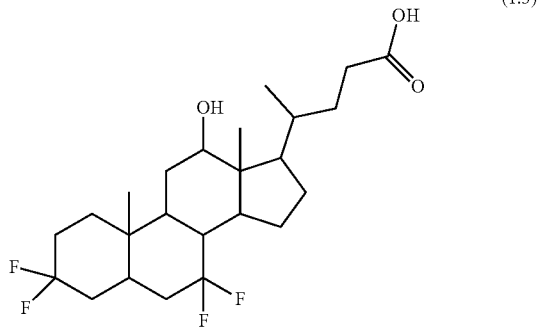

(1.4)

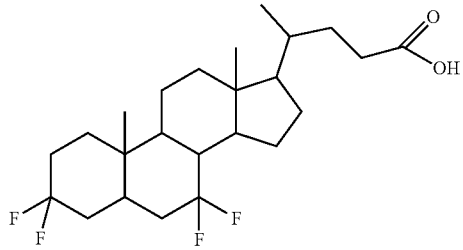

The compound of formula (1.1) is a phosphoryloxy methyl substituent and may have the formula:

(1.5)

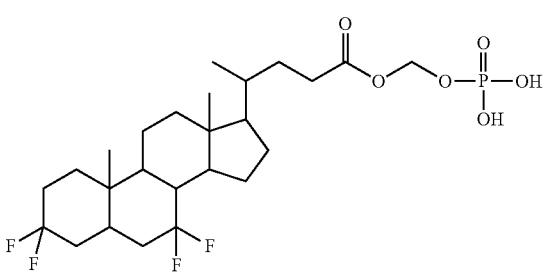

The compound of formula (1.2) is a phosphoryloxy methyl substituent and may have the formula:

(1.6)

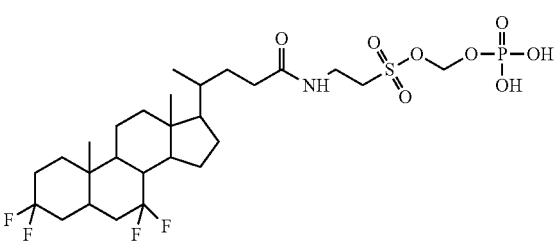

The compound of formula (1.3) is a phosphoryloxy methyl substituent and may have the formula:
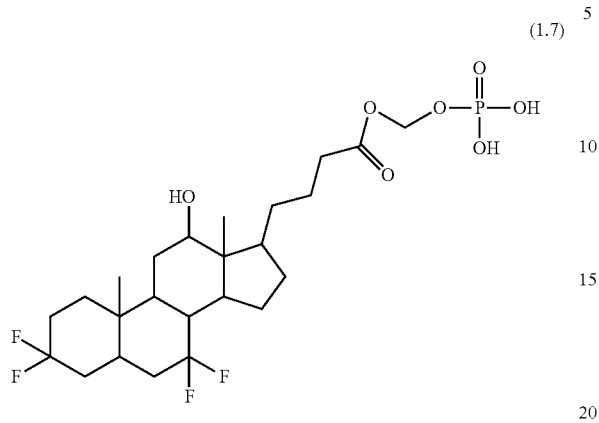
(1.7)
The compound of formula (1.4) is a phosphoryloxy methyl substituent and may have the formula:
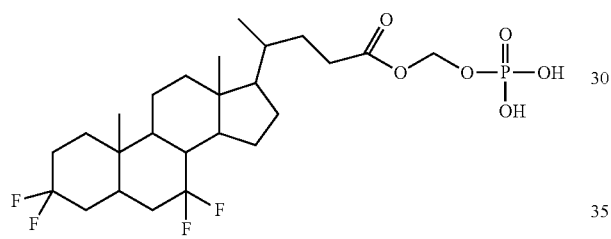
(1.8)
Preferably the compound of formula (1) is a trifluoro compound and may have the formulae:
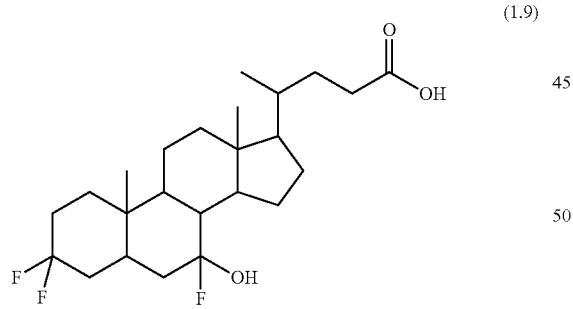
(1.9)
(1.10)
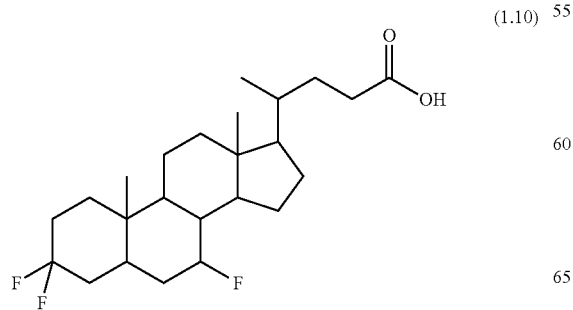
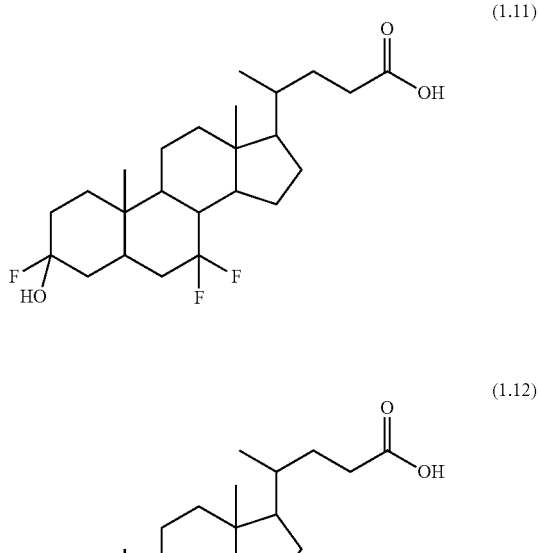
(1.11)
(1.12)
(1.13)
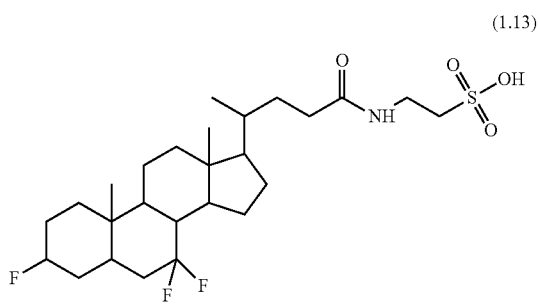
(1.14)
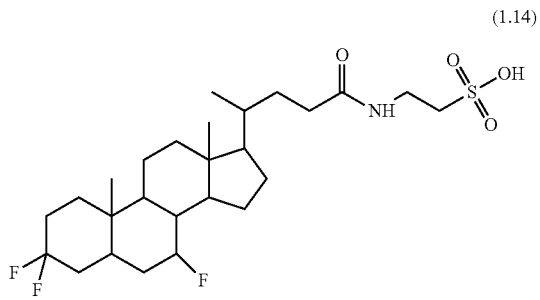
(1.15)
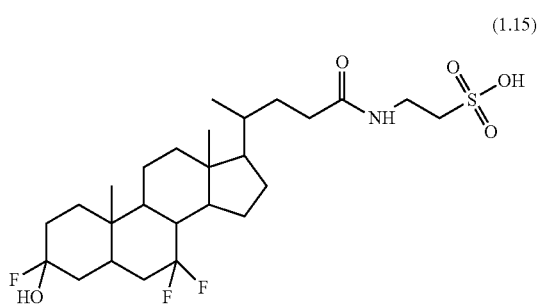

(1.16) 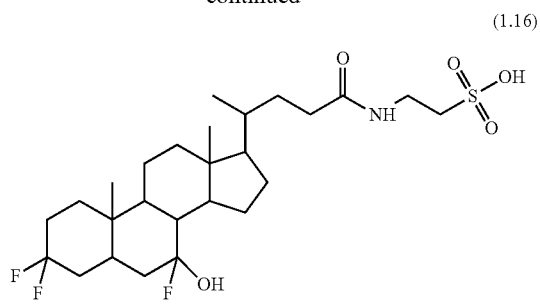
(1.21) 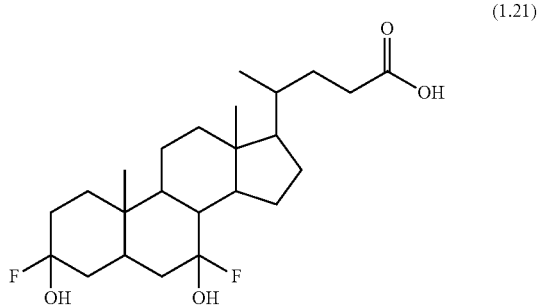
(1.17) 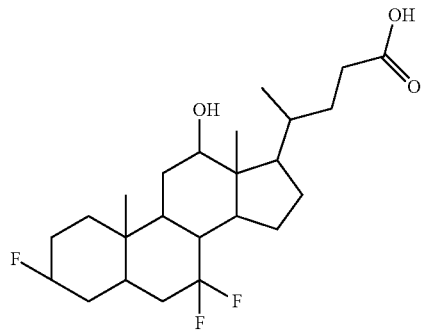
(1.22) 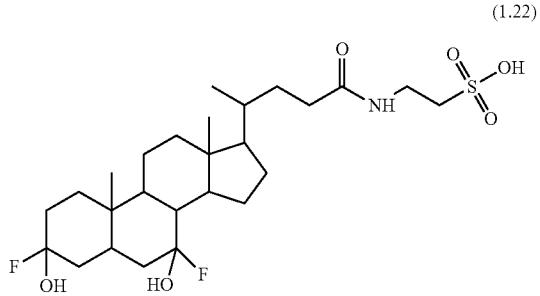
(1.18) 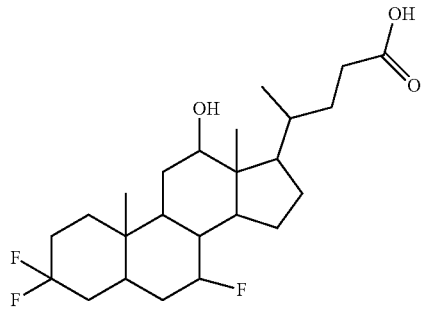
(1.23) 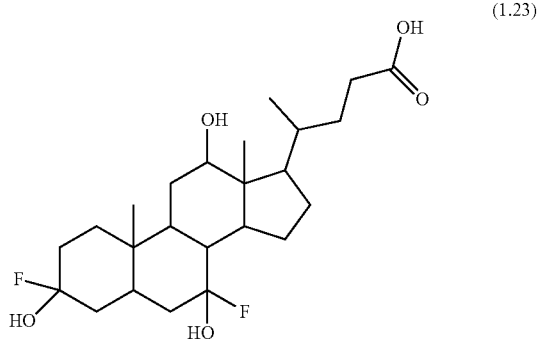
(1.19) 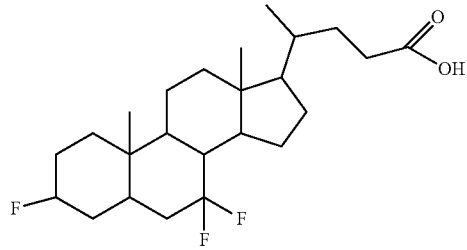
(1.24) 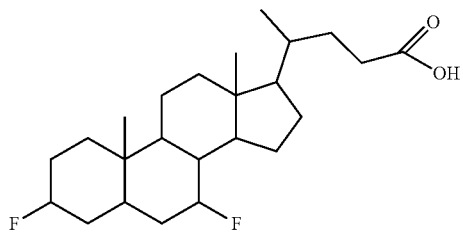
(1.20) 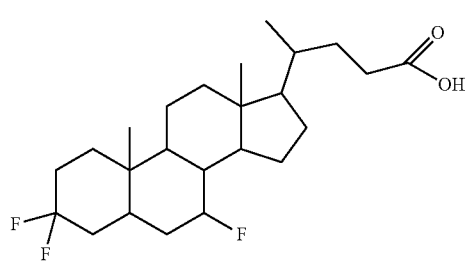
(1.25) 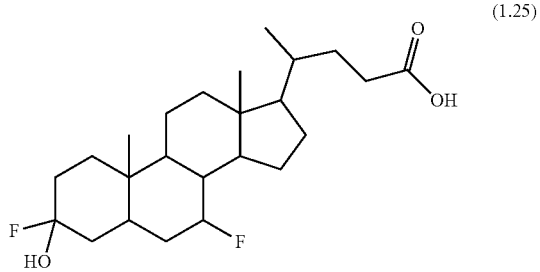
Preferably the compound of formula (1) is a difluoro compound and may have the formulae:
Preferably the compound of formula (1) is a monofluoro compound and may have the formulae:

(1.26) 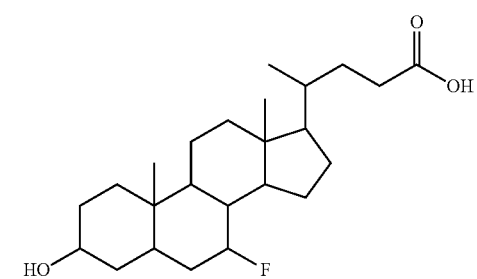
(1.27) 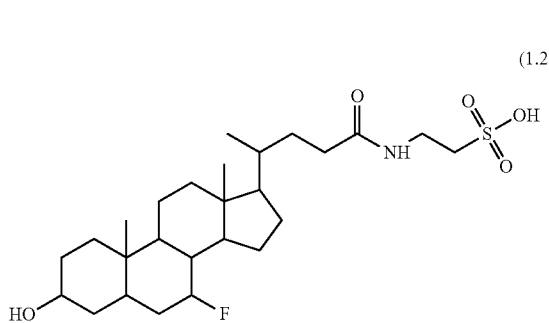
(1.28) 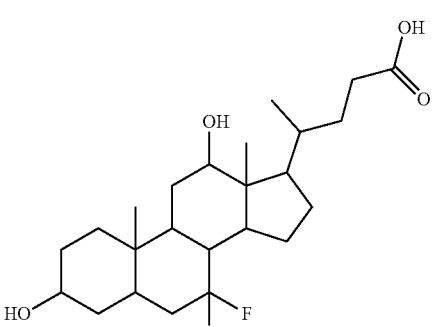
(1.29) 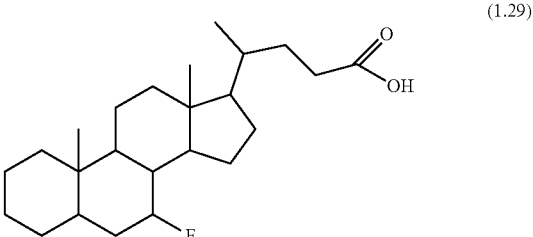
The compound of formula (1) is a phosphoryloxy methyl or a phosphate substituent and may have the formula:
(1.30) 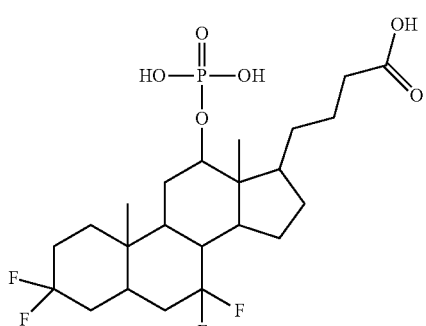
(1.31) 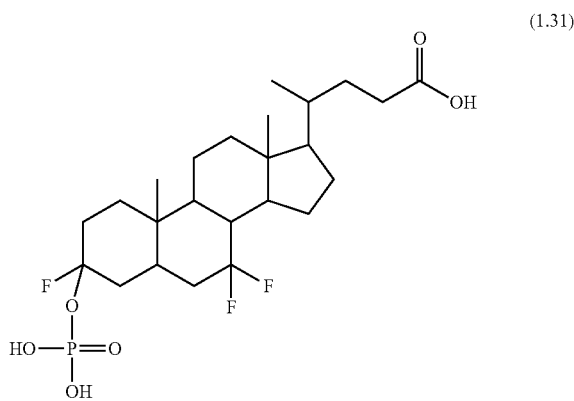
(1.31) 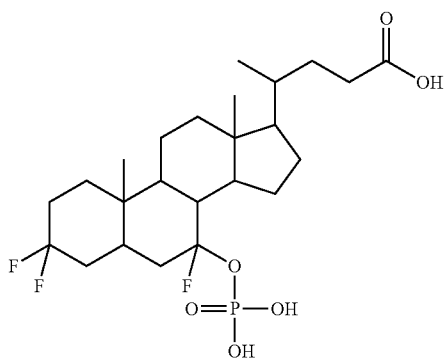
(1.32) 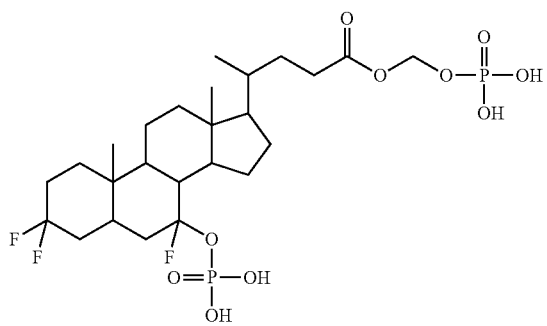

(1.33)
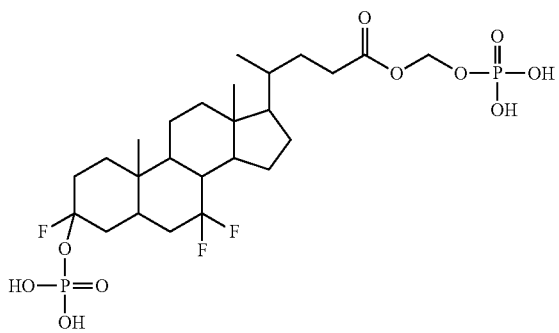
(1.34)
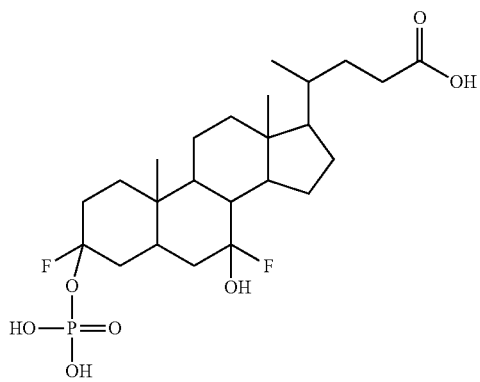
(1.35)
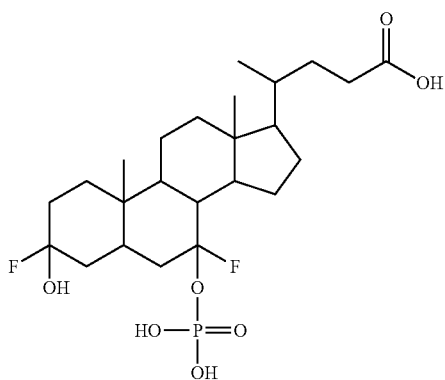
(1.36)
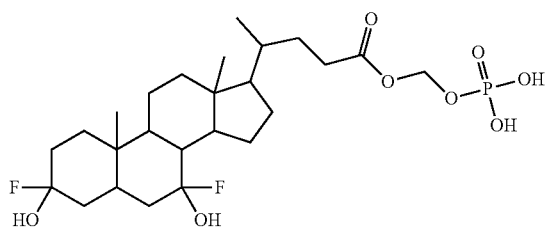
(1.37)
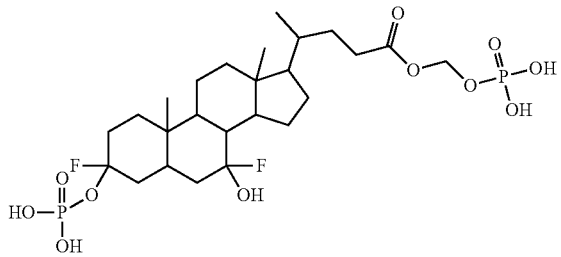
(1.38)
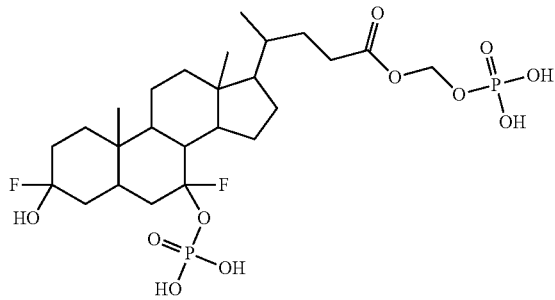
(1.39)
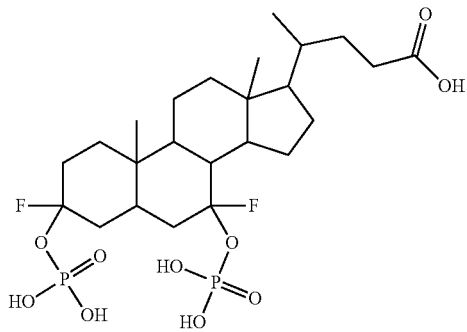
(1.40)
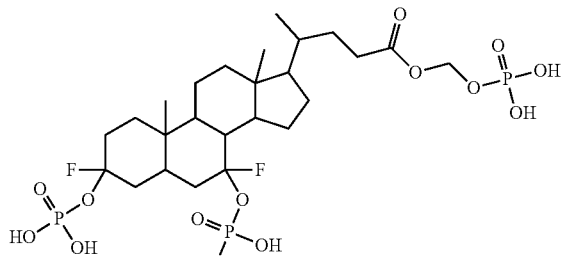

-continued
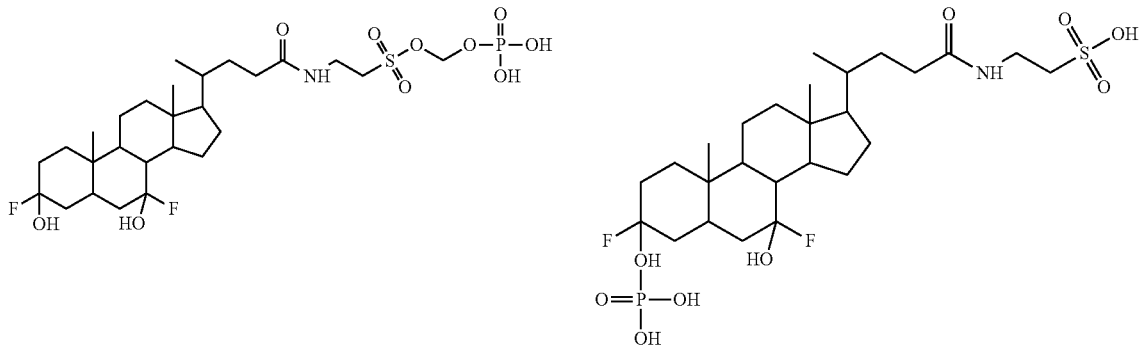
(1.41)
(1.42)
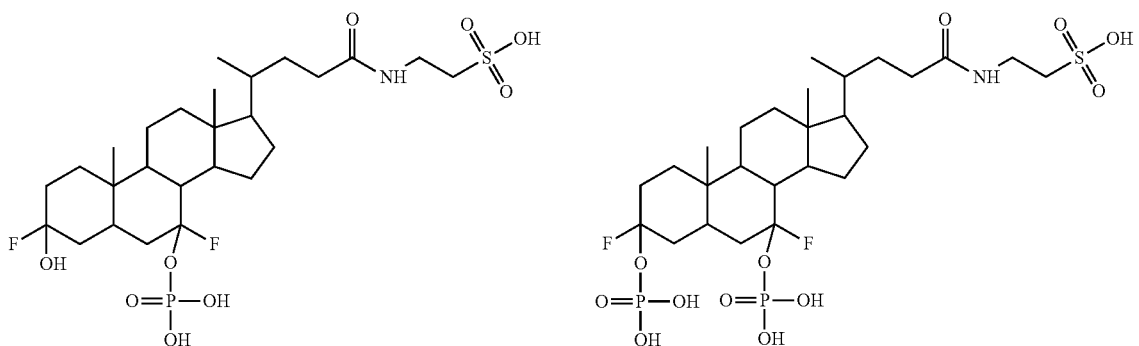
(1.43)
(1.44)
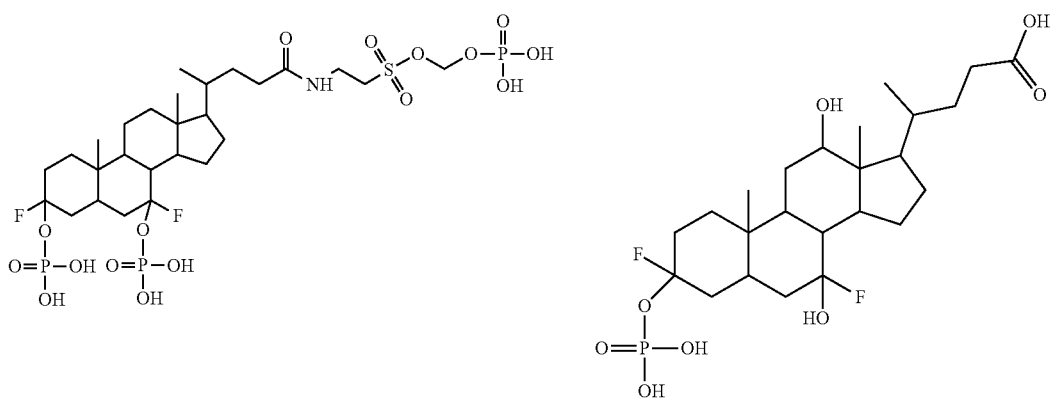
(1.45)
(1.46)
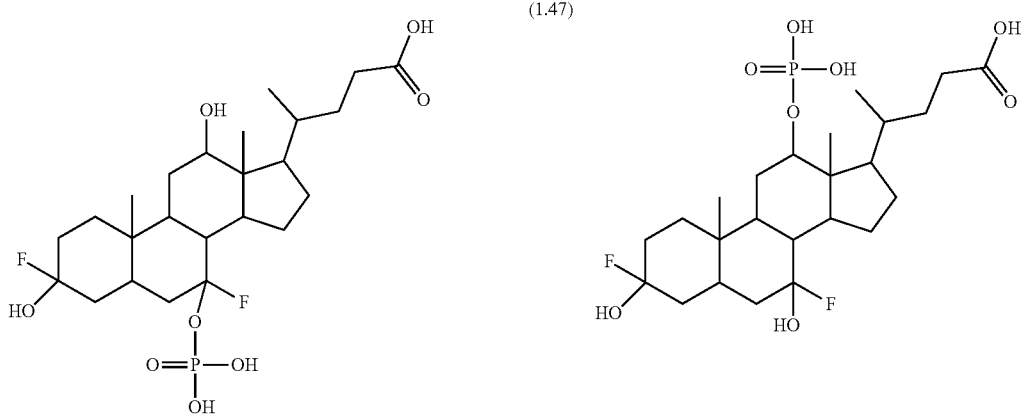
(1.47)
(1.48)

-continued
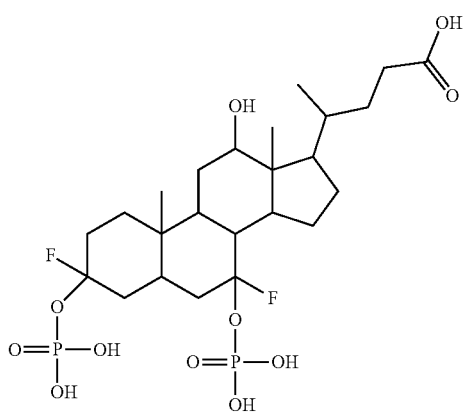
(1.49)
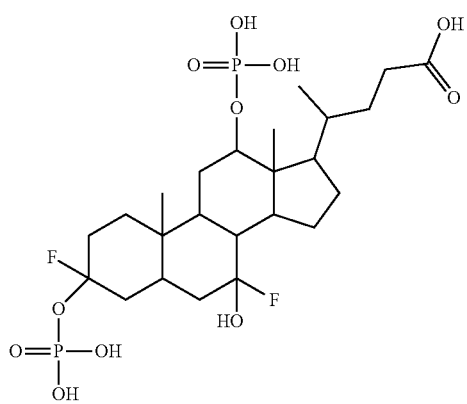
(1.50)
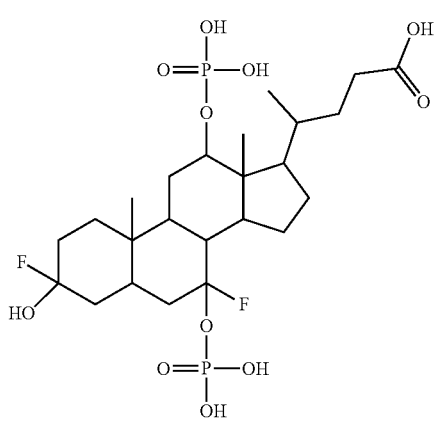
(1.51)
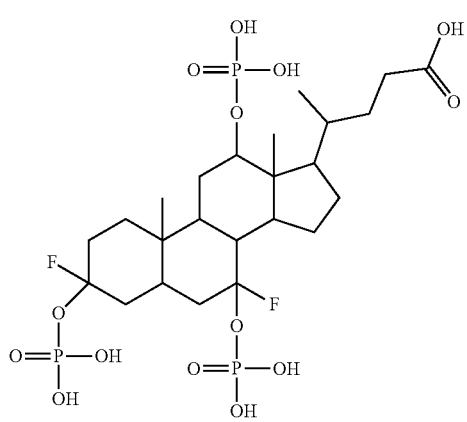
(1.52)
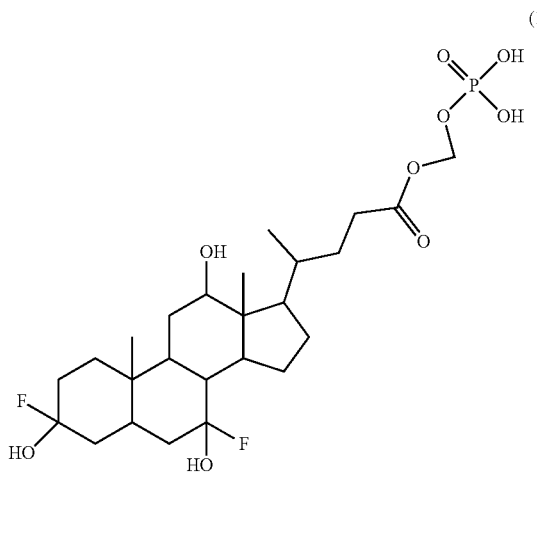
(1.53)
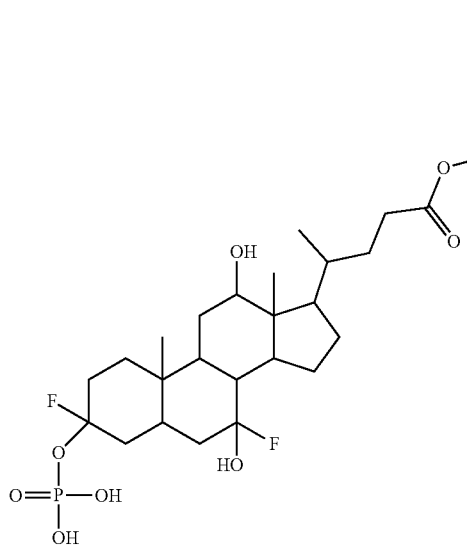
(1.54)

-continued
(1.55)
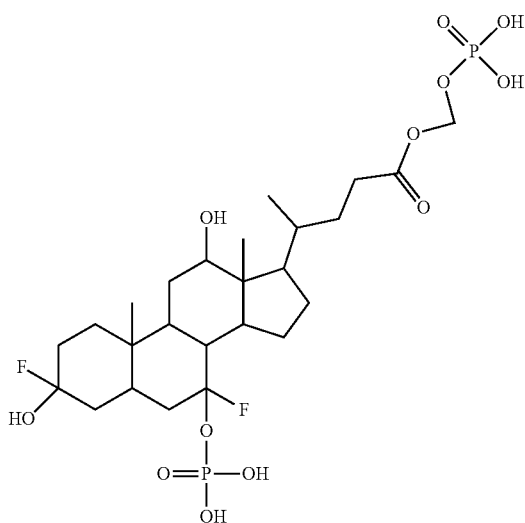
(1.56)
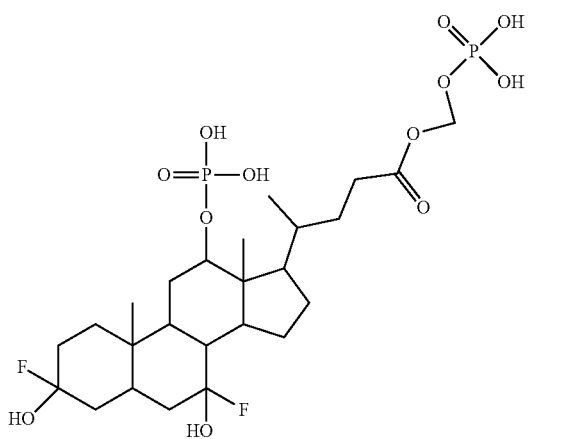
(1.57)
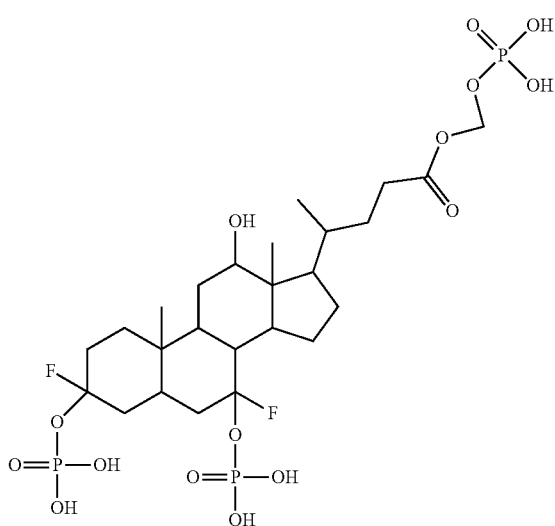
(1.58)
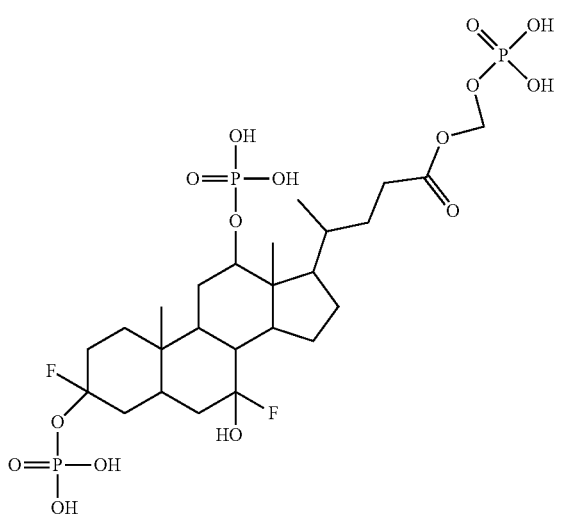
(1.59)
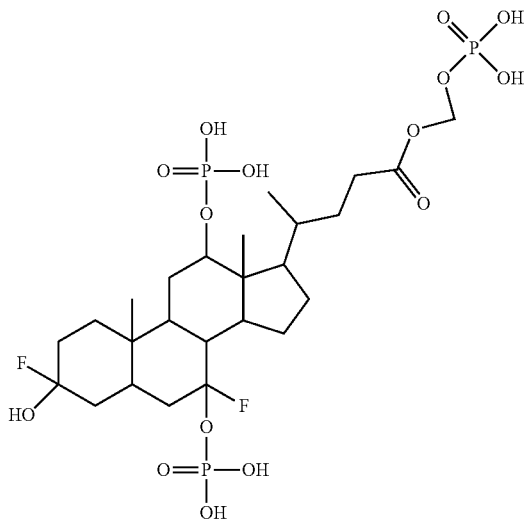
(1.60)
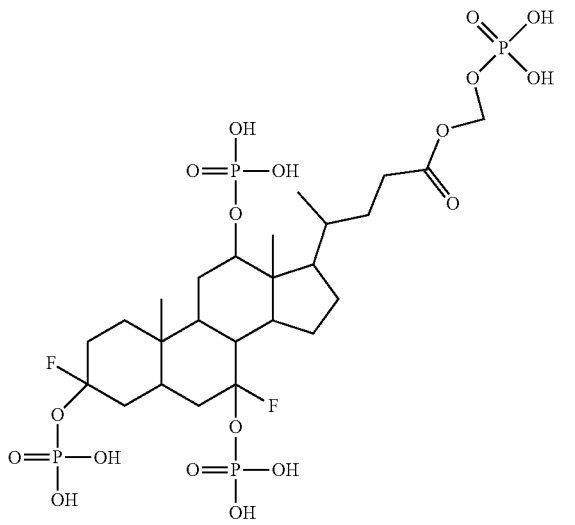

-continued
(1.61)
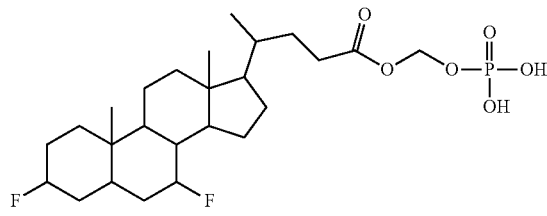
(1.62)
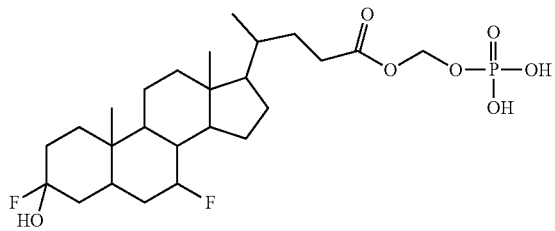
(1.63)
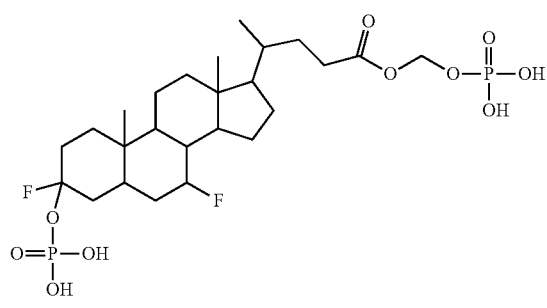
(1.64)
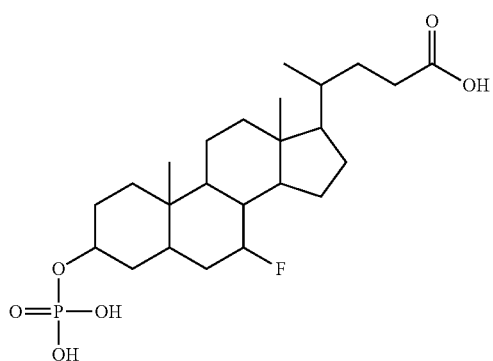
(1.65)
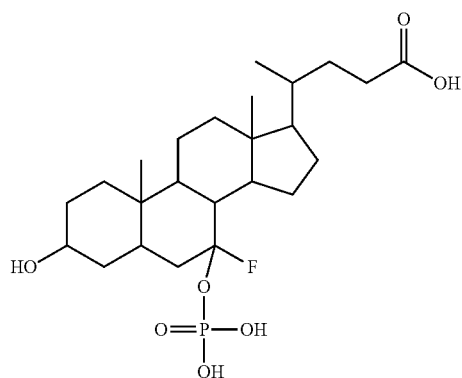
(1.66)
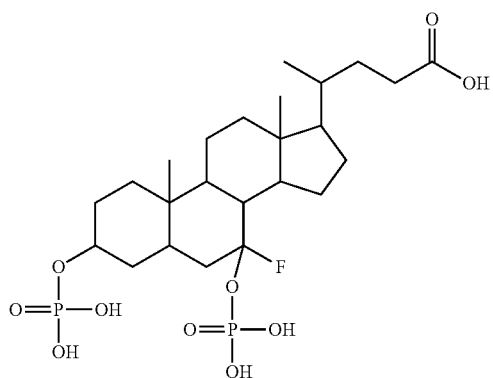
(1.67)
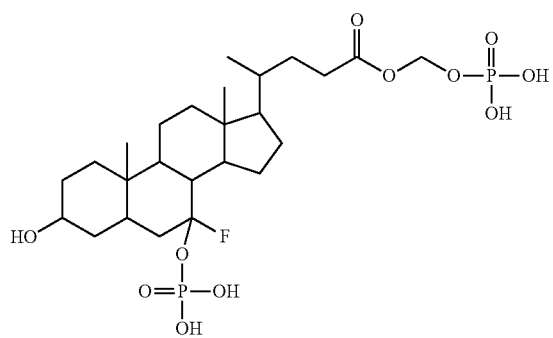
(1.68)
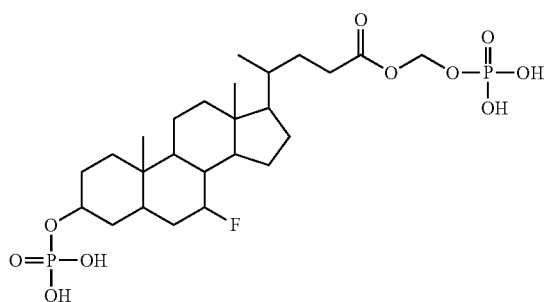

-continued
(1.69)
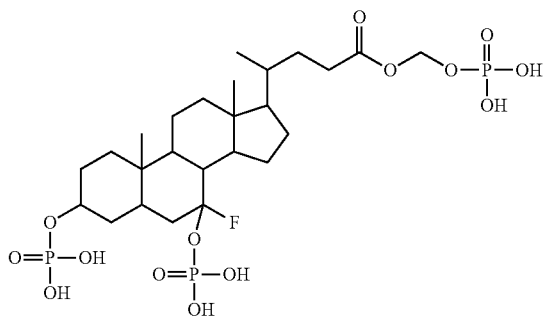
(1.70)
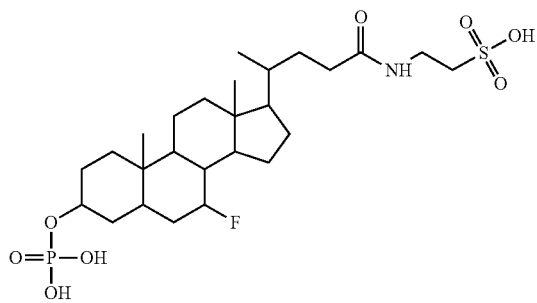
(1.71)
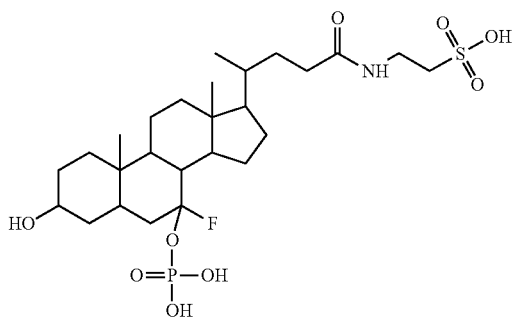
(1.72)
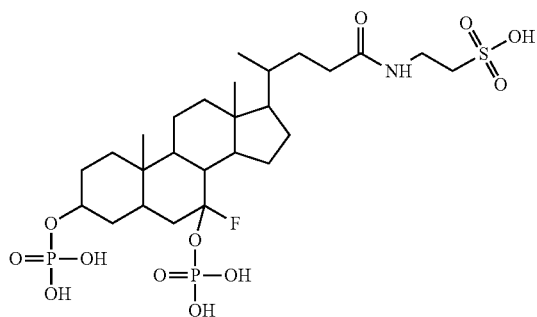
(1.73)
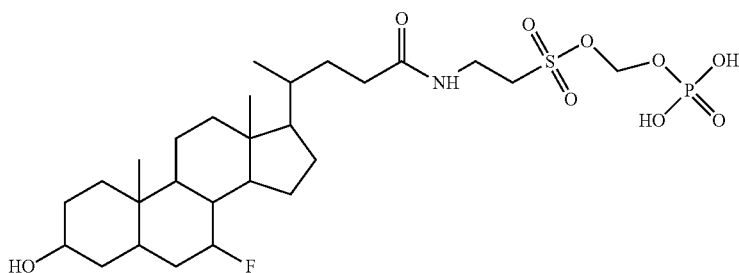
(1.74)
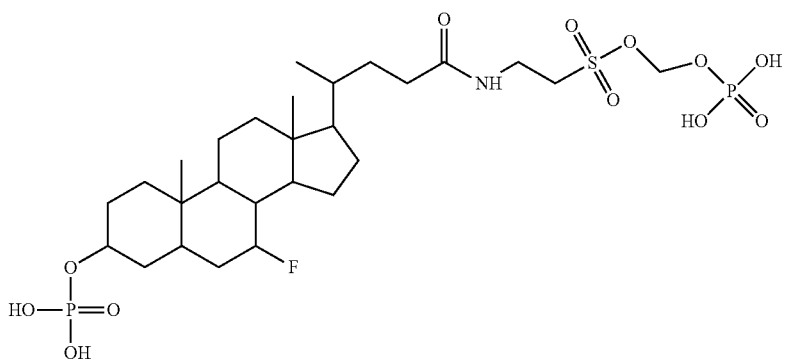

-continued
(1.75)
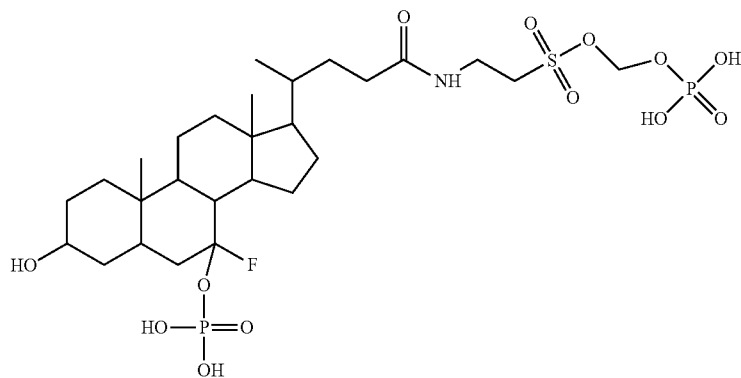
(1.76)
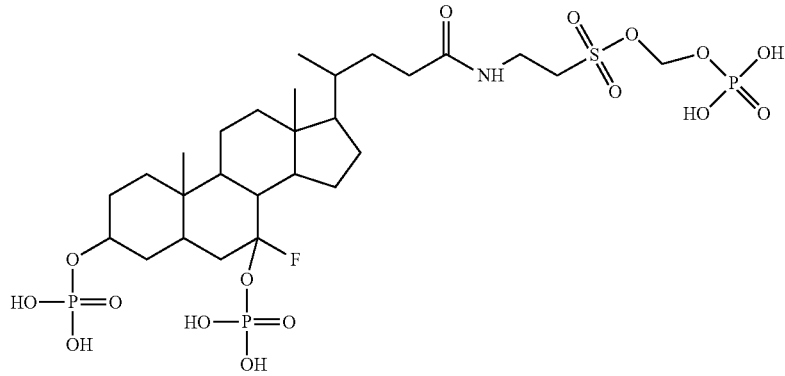
(1.77)
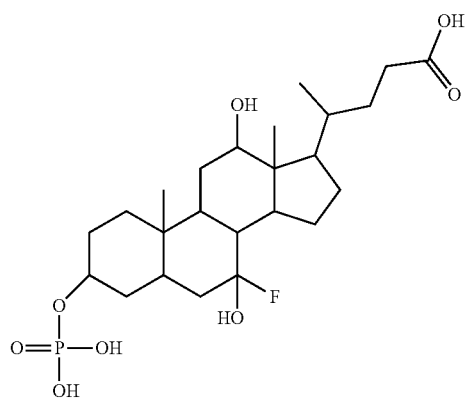
(1.78)
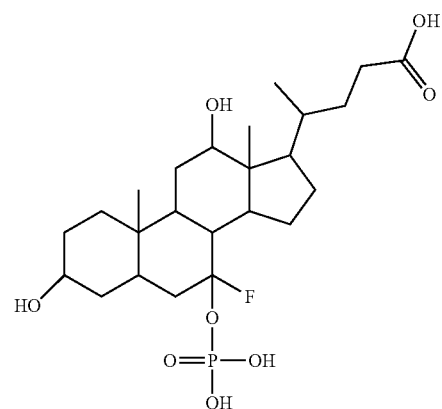
(1.79)
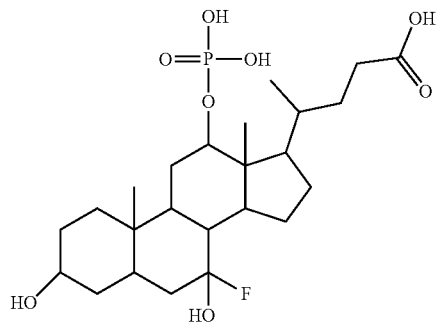
(1.80)
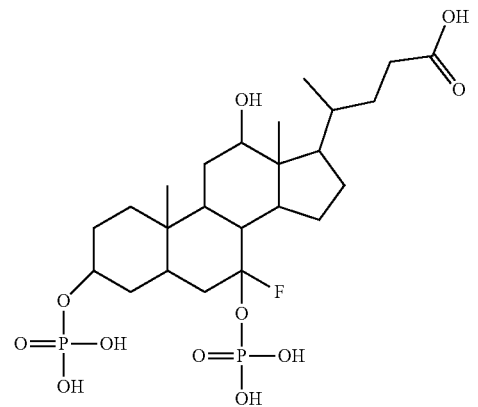

-continued
(1.81)
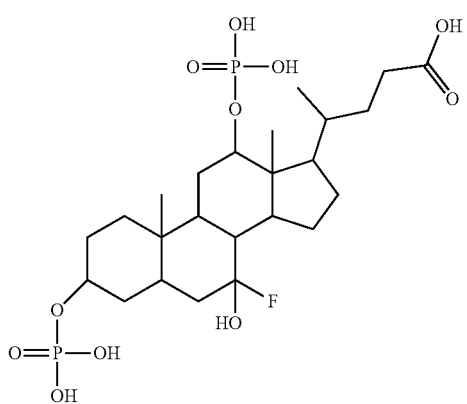
(1.82)
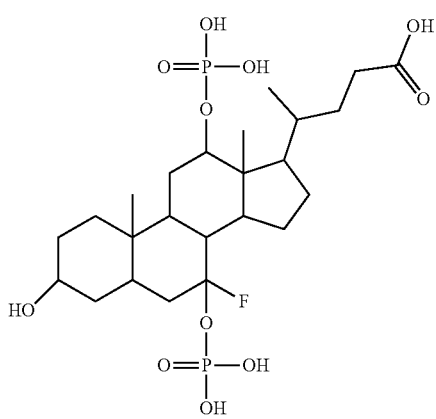
(1.83)
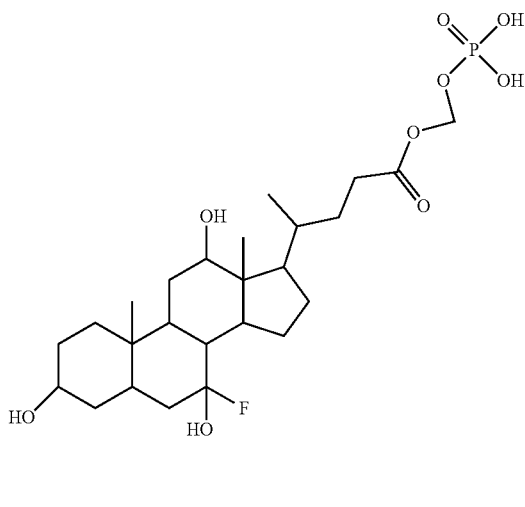
(1.84)
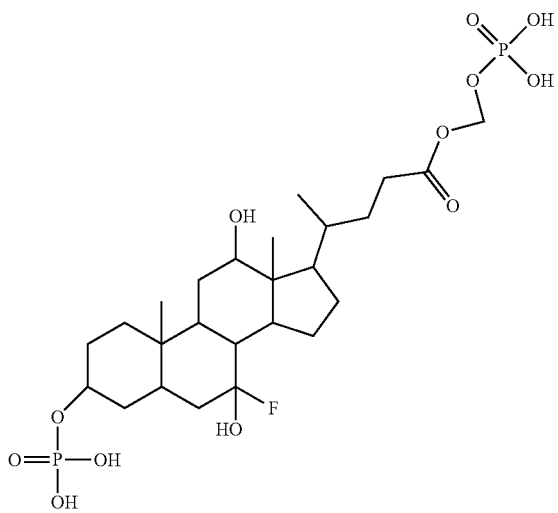
(1.85)
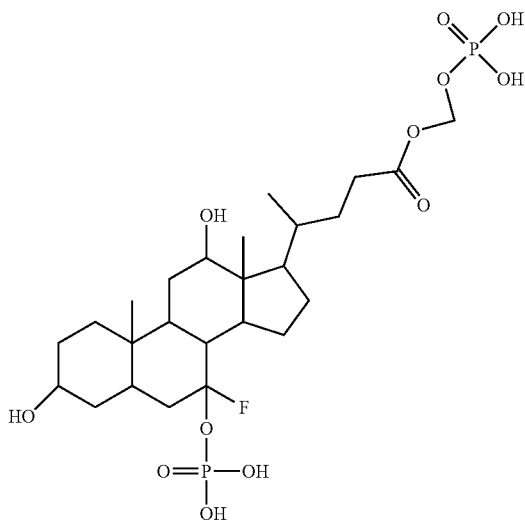
(1.86)
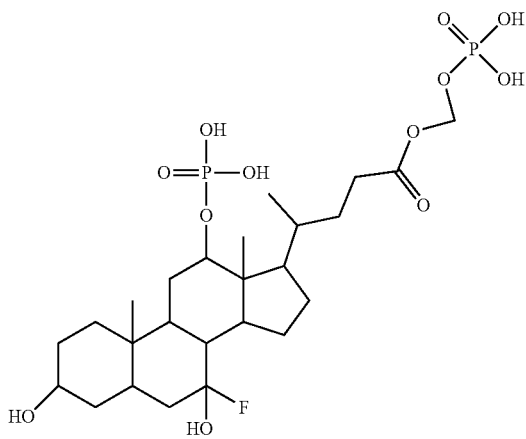

-continued
(1.87)
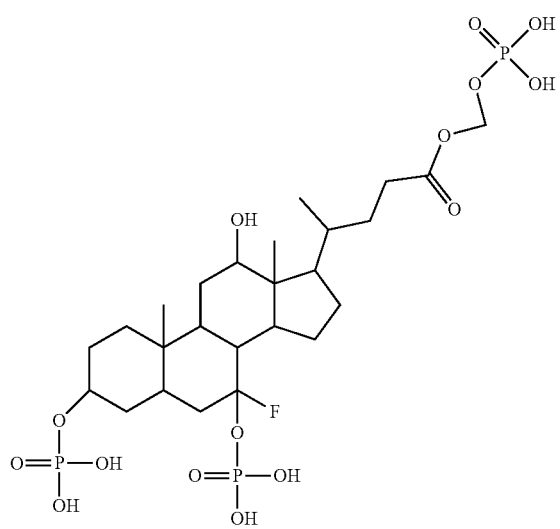
(1.88)
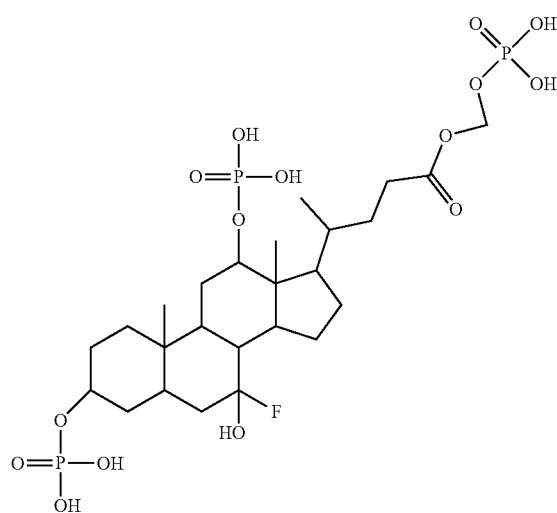
(1.89)
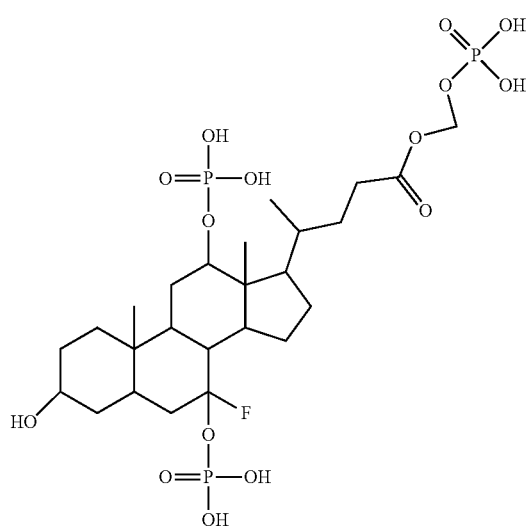
(1.90)
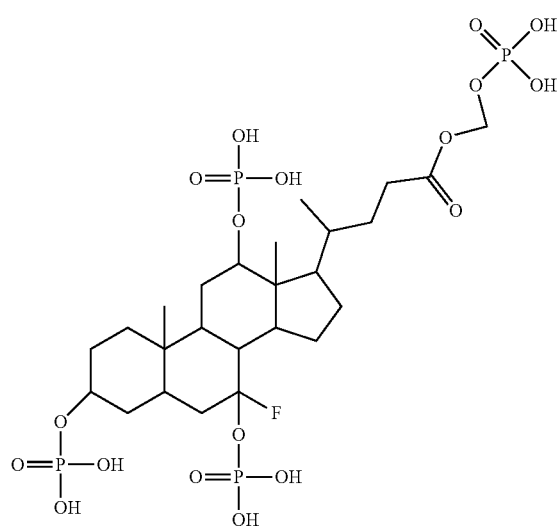
(1.91)
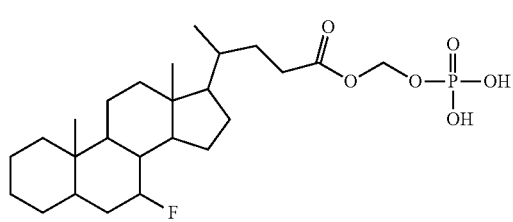
(1.92)
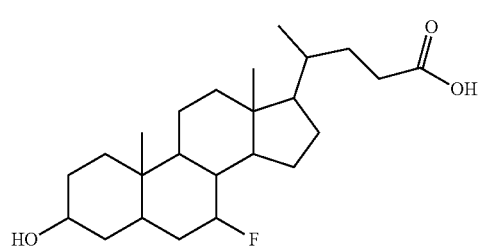

-continued (1.93)
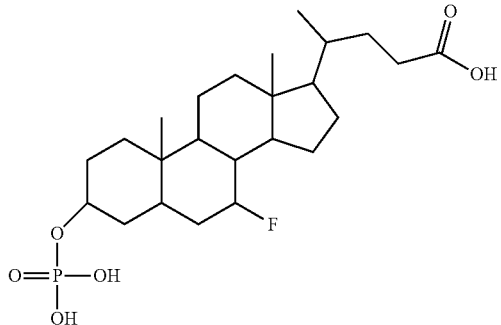

(1.94)
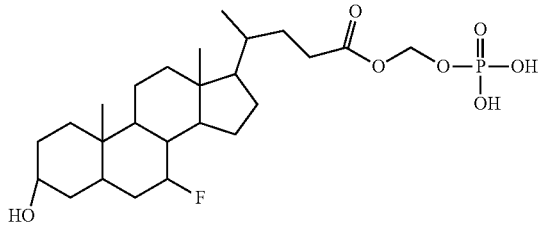

(1.95)
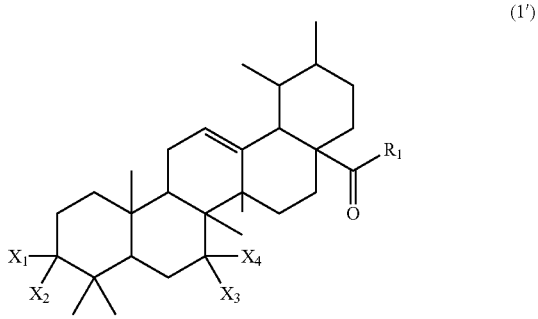

In another aspect is a bile acid having the Formula (1'):

(1')
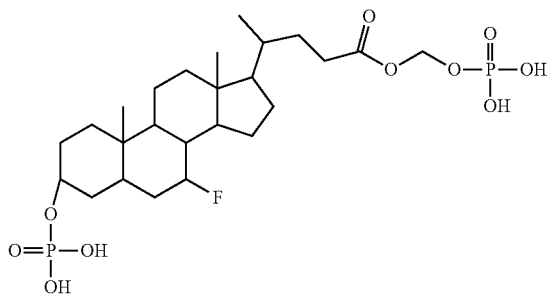

where

R₁ is —OH or —O—(CH₂)—O—P(O)(OH)₂ or —OP(O)(OH)₂; $X_1$ is —F or —H; $X_2$ is —F or —OH, or —OP(O)(OH)₂ or —H; $X_3$ is —F or —H; and $X_4$ is —F or —H.

In one aspect Formula (1') represents a tetrafluoro compound where $X_1$, $X_2$, $X_3$, $X_4$ are all —F.

In another aspect Formula (1') represents a trifluoro compound where $X_1$ is —F, $X_2$-is —F, $X_3$ is —F and $X_4$ is —H In another aspect Formula (1') represents a trifluoro compound where $X_1$ is —F, $X_2$-is —F, $X_3$ is —H and $X_4$ is —F In another aspect Formula (1') represents a trifluoro compound where $X_1$ is —F, $X_2$-is —OH, $X_3$ is —F and $X_4$ is —F.

In another aspect Formula (1') represents a trifluoro compound where $X_1$ is —F, $X_2$-is —OP(O)(OH)₂, $X_3$ is —F and $X_4$ is —F.

In another aspect Formula (1') represents a trifluoro compound where $X_1$ is —F, $X_2$-is —H, $X_3$ is —F and $X_4$ is —F.

In another aspect Formula (1') represents a difluoro compound where $X_1$ is —F, $X_2$ is —F, $X_3$ is —H, and $X_4$ is —H.

In another aspect Formula (1') represents a difluoro compound where $X_1$ is —F, $X_2$ is —OH, $X_3$ is —F, and $X_4$ is —H.

In another aspect Formula (1') represents a difluoro compound where $X_1$ is —F, $X_2$ is —OP(O)(OH)₂, $X_3$ is —F, and $X_4$ is —H.

In another aspect Formula (1') represents a difluoro compound where $X_1$ is —F, $X_2$ is —H, $X_3$ is —F, and $X_4$ is —H.

In another aspect Formula (1') represents a difluoro compound where $X_1$ is —F, $X_2$ is —OH, $X_3$ is —H, and $X_4$ is —F.

In another aspect Formula (1') represents a difluoro compound where $X_1$ is —F, $X_2$ is —OP(O)(OH)₂, $X_3$ is —H, and $X_4$ is —F.

In another aspect Formula (1') represents a difluoro compound where $X_1$ is —F, $X_2$ is —H, $X_3$ is —H, and $X_4$ is —F.

In another aspect Formula (1') represents a difluoro compound where $X_1$ is —H, $X_2$ is —F, $X_3$ is —F, and $X_4$ is —H.

In another aspect Formula (1') represents a difluoro compound where $X_1$ is —H, $X_2$ is —F, $X_3$ is —H, and $X_4$ is —F.

In another aspect Formula (1') represents a difluoro compound where $X_1$ is —H, $X_2$ is —OH, $X_3$ is —F, and $X_4$ is —F.

In another aspect Formula (1') represents a difluoro compound where $X_1$ is —H, $X_2$ is —OP(O)(OH)₂, $X_3$ is —F, and $X_4$ is —F.

In another aspect Formula (1') represents a difluoro compound where $X_1$ is —H, $X_2$ is —H, $X_3$ is —F, and $X_4$ is —F.

Preferably the compound of formula (1') is a tetrafluoro compound and may have the formula:
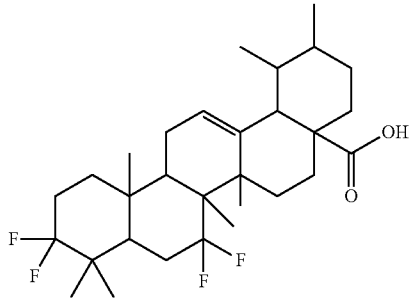
(2.1)
Preferably the compound of formula (2) is a trifluoro compound and may also have the formula:
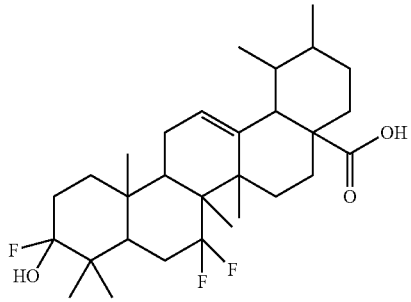
(2.2)
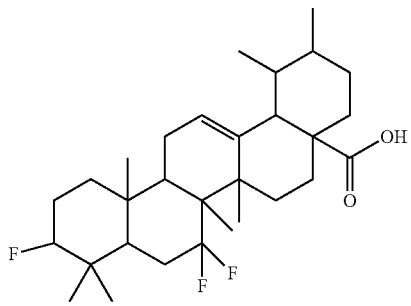
(2.3)
Preferably the compound of formula (2) is a difluoro compound and may also have the formula:
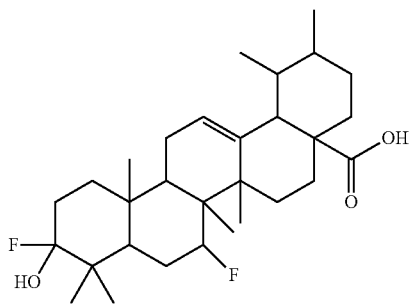
(2.4)
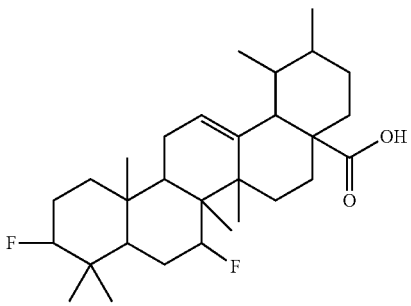
(2.5)
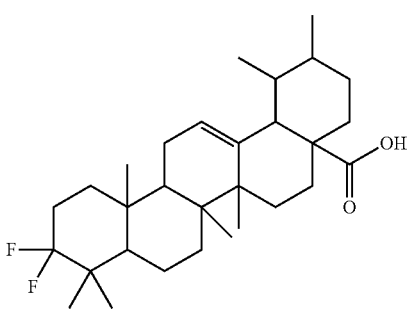
(2.6)
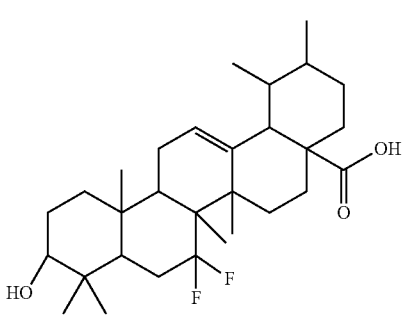
(2.7)
Preferably the compound of formula (2) is a monofluoro compound and may also have the formula:
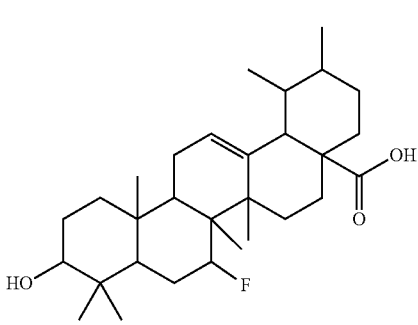
(2.7)
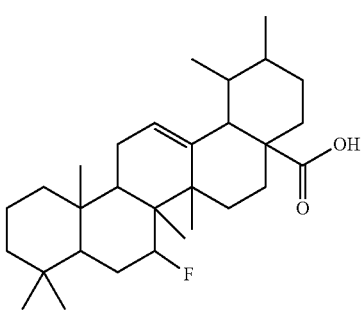
(2.8)

(2.9)
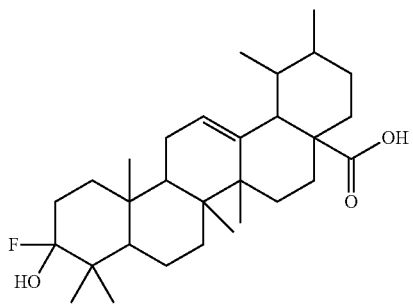
(2.13)
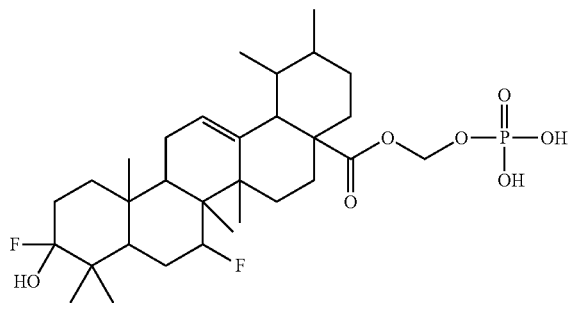
(2.10)
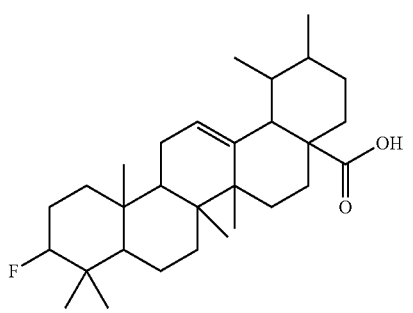
(2.14)
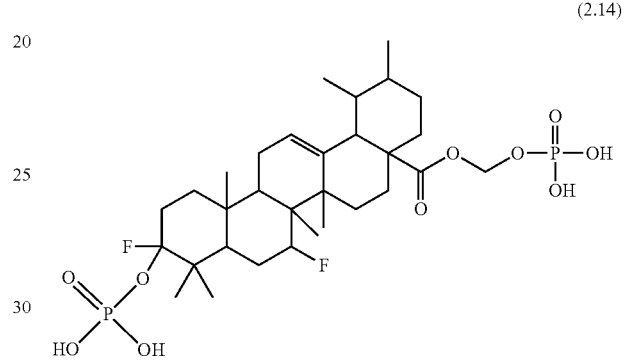
In some embodiments of the compound (2) a phosphoryloxy methyl or phosphate derivative having the formula:
(2.11) (2.15)
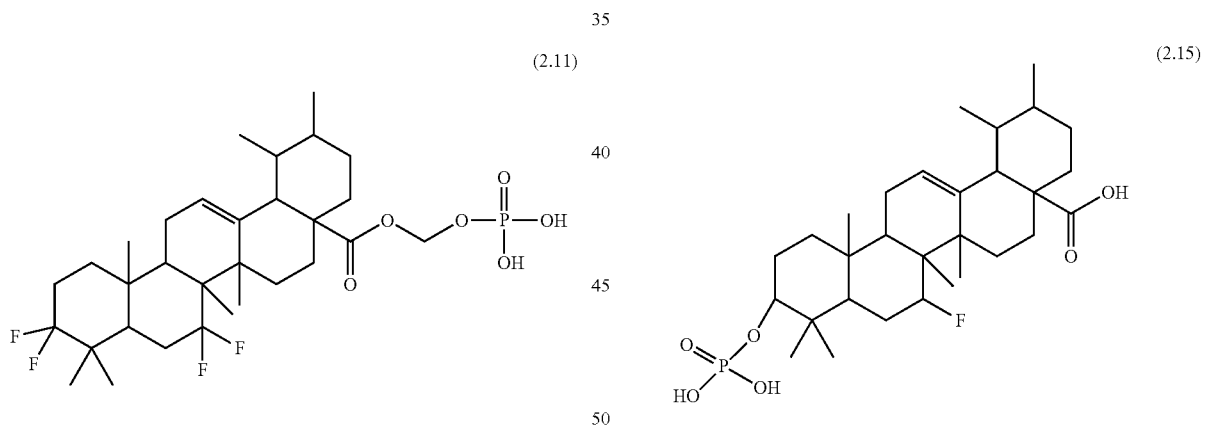
(2.12)
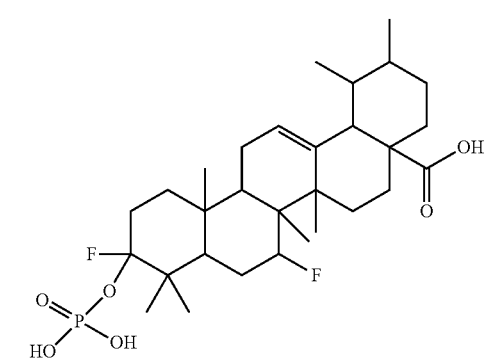
(2.16)
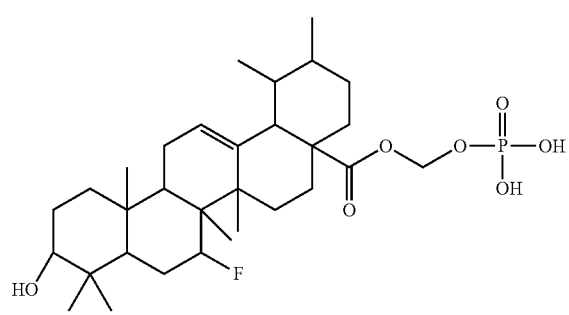

(2.17)

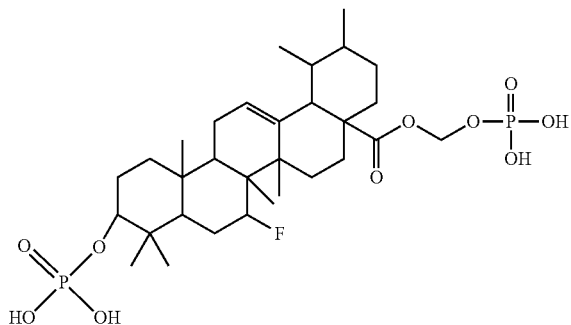

Alkylated Bile Acids

The replacement of the hydrogen or hydroxyl in pharmaceutically-active molecules with an alkyl group such as a —$CH_3$ may greatly improve the biological activity several-fold. Methylation can have a profound effect on both the chemical and pharmacological properties of the target drug molecule. Described herein are examples of methylated bile acids.

In the first aspect is a bile acid compound having the Formula (2):

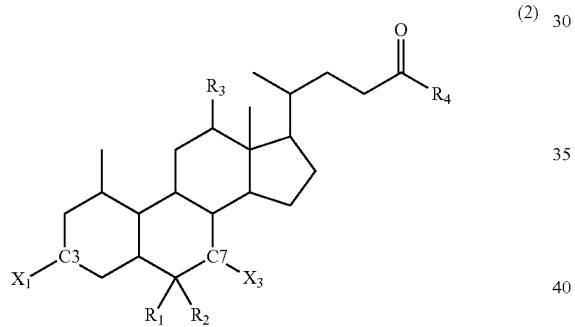

(2)

where $R_1$ is —OH or —H or —OP(O)(OH)$_2$; $R_2$ is —OH or —H or —OP(O)(OH)$_2$; $R_3$ is —OH, —H, or —OP(O)(OH)$_2$; $R_4$ is —OH, —NH(CH$_2$)$_2$SO$_3$H, —NHCH$_2$COOH, or —O—(CH$_2$)—O—P(O)(OH)$_2$; $X_1$ is —O(CH$_3$) or —O(C$_2$H$_5$) or —OCH(CH$_3$)$_2$ or —H or —OH or —OP(O)(OH)$_2$; $X_3$ is —O(CH$_3$) or —O(C$_2$H$_5$), or —CH(CH$_3$)$_2$ or —OH, or —H or —OP(O)(OH)$_2$. Carbon positions 3 and 7 are identified in Formula (I) above.

In one aspect of the Formula (2) $X_1$ is —O(CH$_3$) and $X_3$ is —O(CH$_3$) or —O(C$_2$H$_5$), or —CH(CH$_3$)$_2$ or —OH, —H or —OP(O)(OH)$_2$.

In another aspect of the Formula (2), $X_1$ is —O(C$_2$H$_5$) and $X_3$ is —O(CH$_3$) or —O(C$_2$H$_5$) or —CH(CH$_3$)$_2$ or —OH or —H or —OP(O)(OH)$_2$.

In one aspect of the Formula (2) $X_1$ is —OCH(CH$_3$)$_2$ and $X_3$ is —O(CH$_3$) or —O(C$_2$H$_5$), or —CH(CH$_3$)$_2$ or —OH or —H or —OP(O)(OH)$_2$.

In another aspect of the Formula (2), $X_1$ is —OH and $X_3$ is —O(CH$_3$) or —O(C$_2$H$_5$) or —CH(CH$_3$)$_2$.

In another aspect of the Formula (2), $X_1$ is —H and $X_3$ is —O(CH$_3$) or —O(C$_2$H$_5$), or —CH(CH$_3$)$_2$.

In another aspect of the Formula (2), $X_1$ is —OP(O)(OH)$_2$ and $X_3$ is —O(CH$_3$) or —O(C$_2$H$_5$) or —CH(CH$_3$)$_2$.

In another aspect of the Formula (2) $X_1$ is —O(CH$_3$) or —O(C$_2$H$_5$) or —H or —OH or —OP(O)(OH)$_2$ and $X_3$ is —O(CH$_3$).

In another aspect of the Formula (2) $X_1$ is —O(CH$_3$) or —O(C$_2$H$_5$) or —H or —OH or —OP(O)(OH)$_2$ and $X_3$ is —O(C$_2$H$_5$).

In another aspect of the Formula (2) $X_1$ is —O(CH$_3$) or —O(C$_2$H$_5$) or —H or —OH or —OP(O)(OH)$_2$ and $X_3$ is —OCH(CH$_3$)$_2$.

In another aspect of the Formula (2) $X_1$ is —O(CH$_3$) or —O(C$_2$H$_5$) and $X_3$ is —OH.

In another aspect of the Formula (2) $X_1$ is —O(CH$_3$) or —O(C$_2$H$_5$) and $X_3$ is —H.

In another aspect of the Formula (2) $X_1$ is —O(CH$_3$) or —O(C$_2$H$_5$) and $X_3$ is —OP(O)(OH)$_2$.

In another aspect of the Formula (2), if both $R_1$ and $R_2$ are —H, then only either $X_1$ or $X_3$ are —OH, but not both.

In another aspect of the Formula (2) at least one of the groups $X_1$ or $X_3$ contains a carbon atom.

In another aspect of the Formula (2) at least one of the $X_1$ or $X_3$ groups are alkylated.

In another aspect of the Formula (2) at least one of the $X_1$ or $X_3$ groups are O-alkylated.

In some embodiments of Formula (2) the compound may have the formulae:

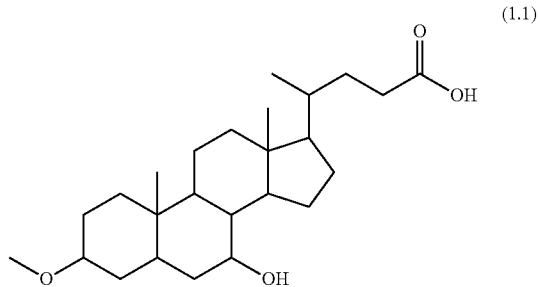

(1.1)

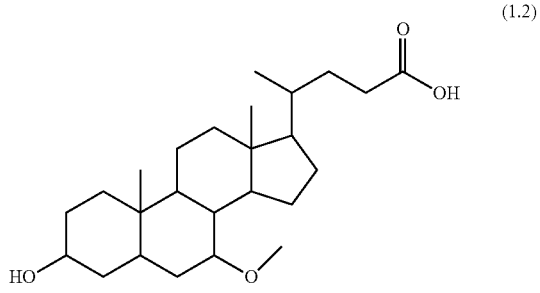

(1.2)

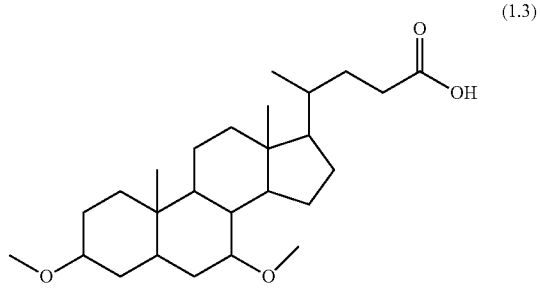

(1.3)

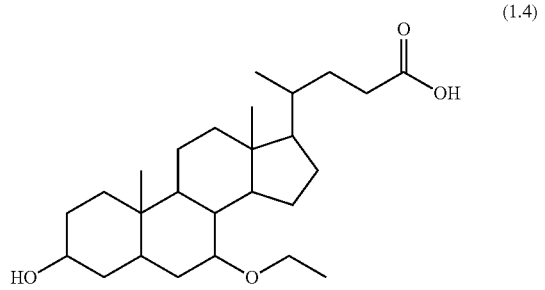
(1.4)
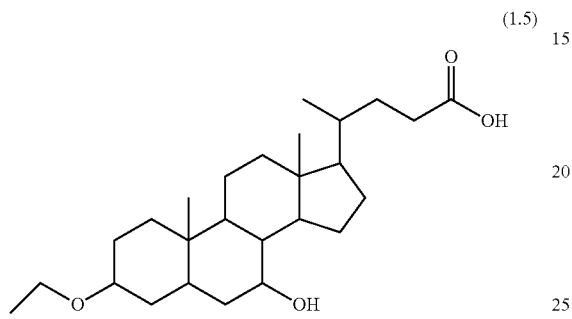
(1.5)
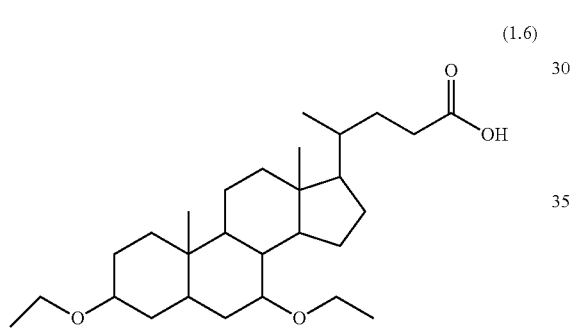
(1.6)
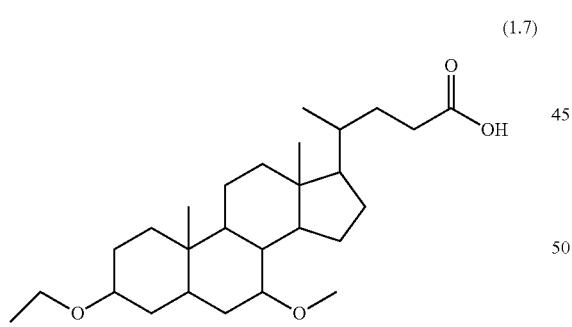
(1.7)
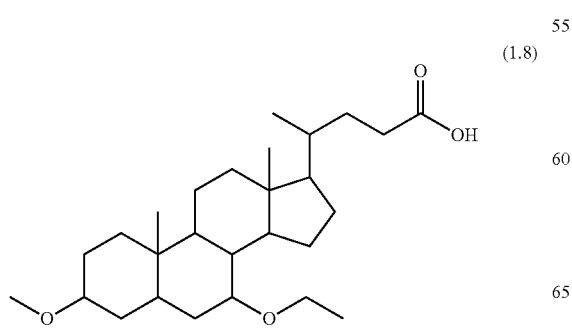
(1.8)
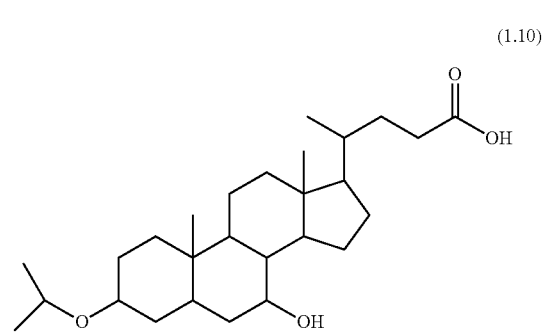
(1.9)
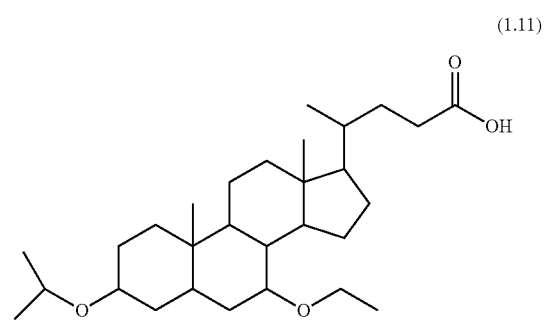
(1.10)
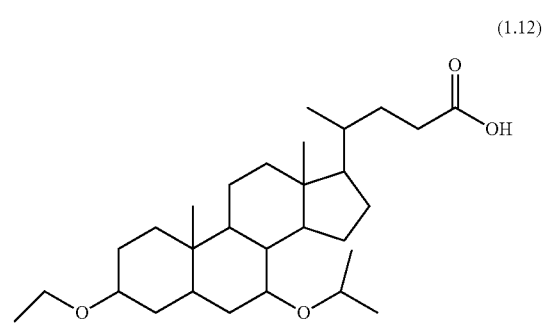
(1.11)
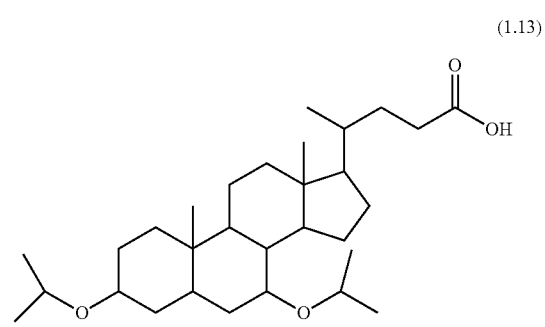
(1.12)
(1.13)

(1.14)
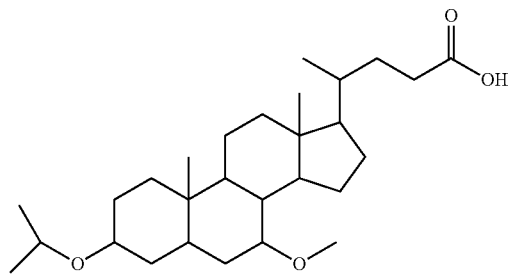
(1.15)
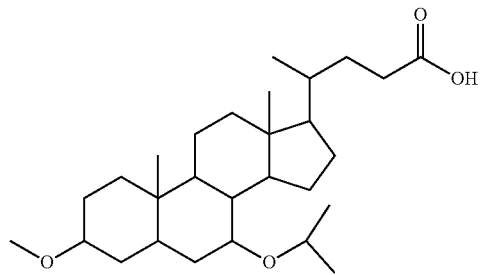
or a pharmaceutically acceptable salt thereof.
In some embodiments of Formulae (1.1-1.15) the compounds may have the formulae:
(1.16)
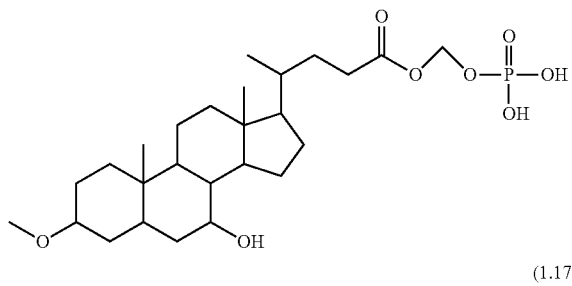
(1.17)
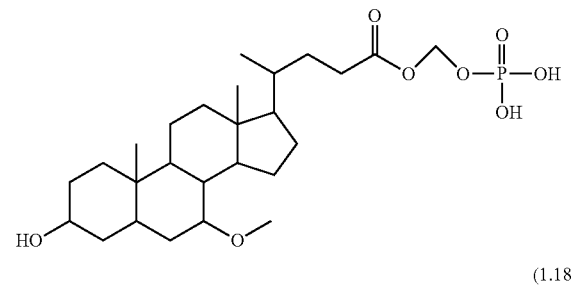
(1.18)
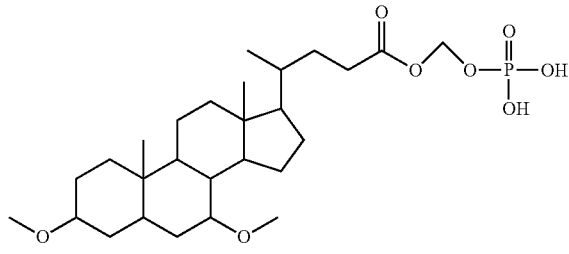
(1.19)
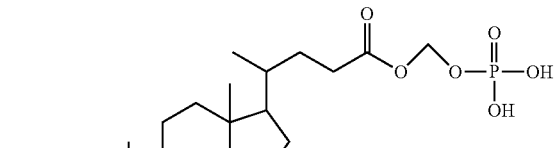
(1.20)
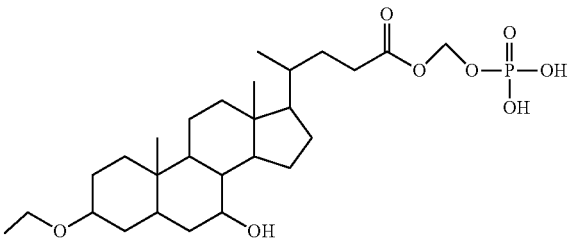
(1.21)
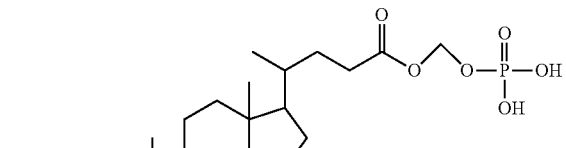
(1.22)
(1.23)
(1.24)
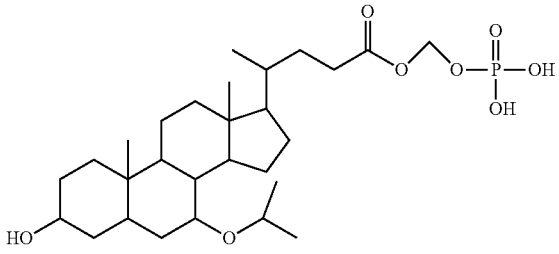

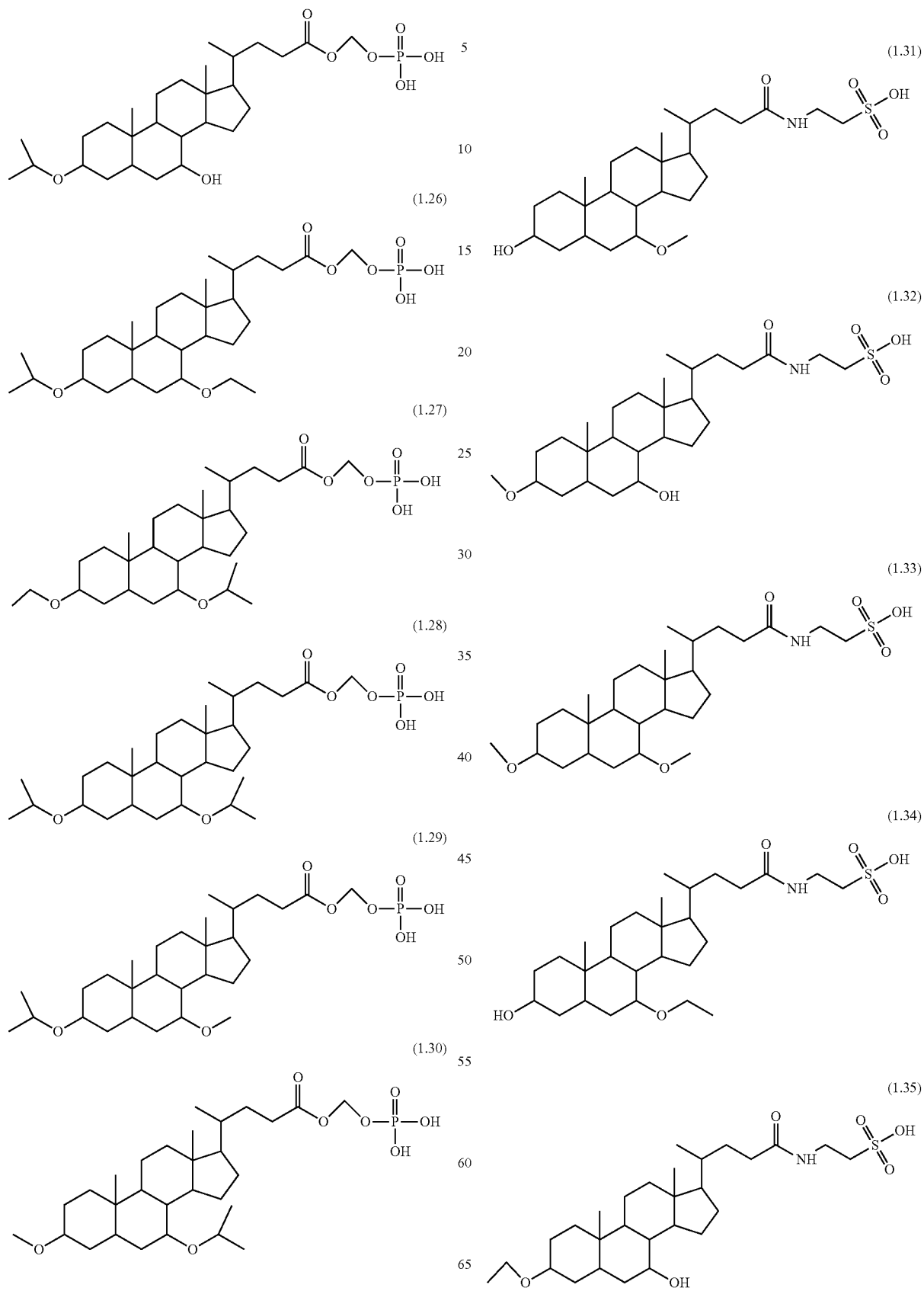
In some embodiments of the Formula (2) the compounds may have the formulae:
or a pharmaceutically acceptable salt thereof.

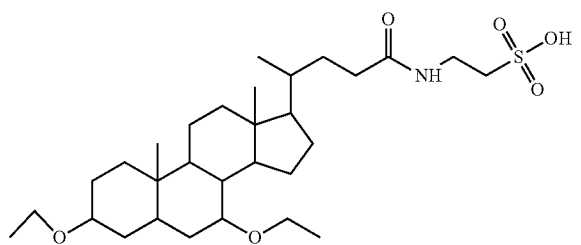
(1.36)
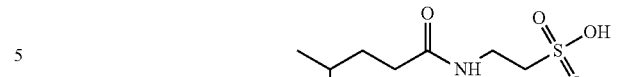
(1.41)
(1.42)
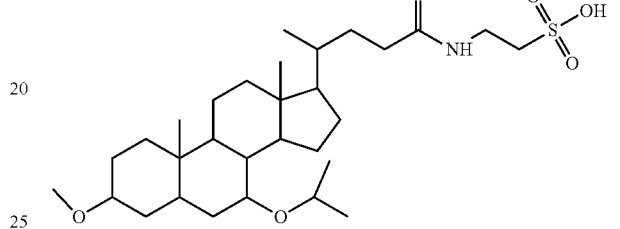
(1.43)
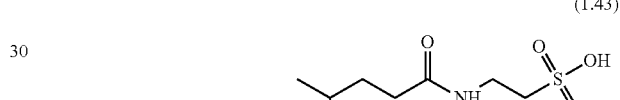
(1.44)
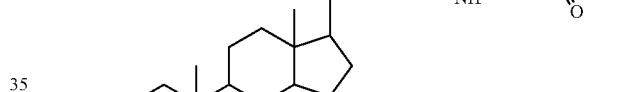
(1.45)
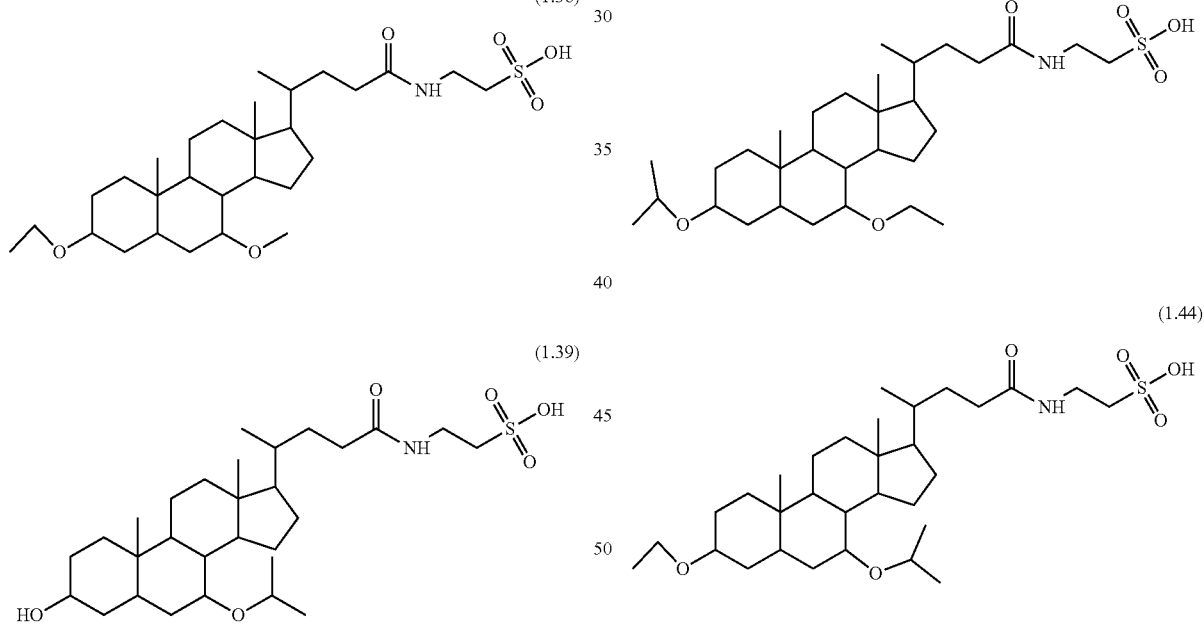
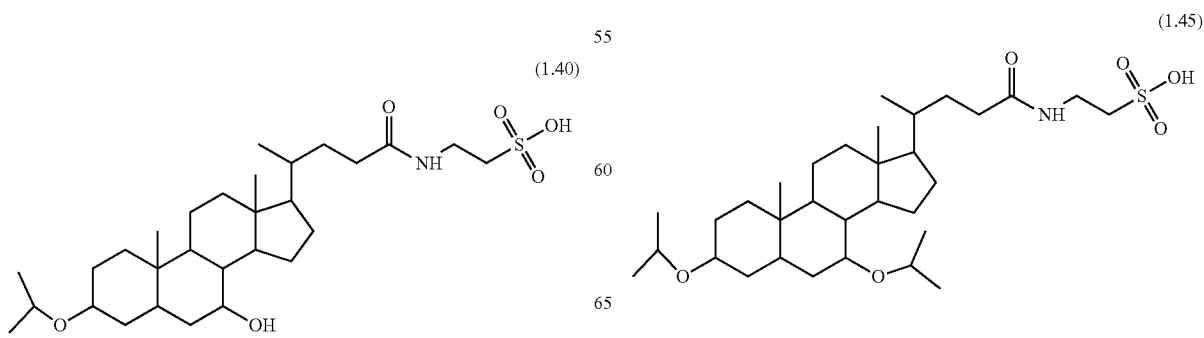
or a pharmaceutically acceptable salt thereof.

In some embodiment of the formula 1.31-1.45) the compounds may have the formulae:
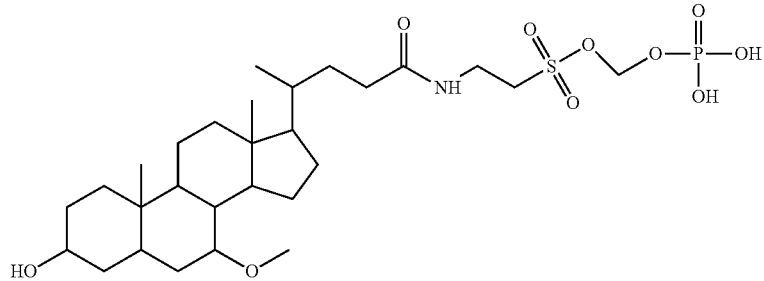
(1.46)
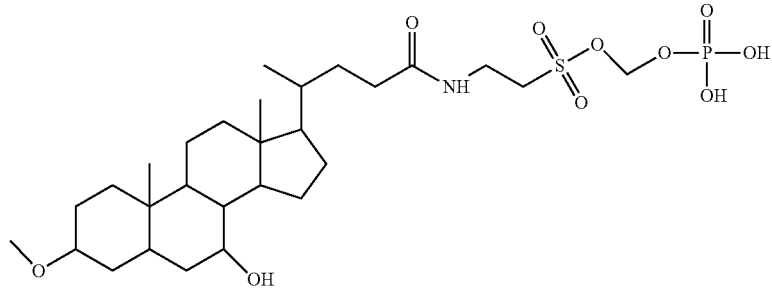
(1.47)
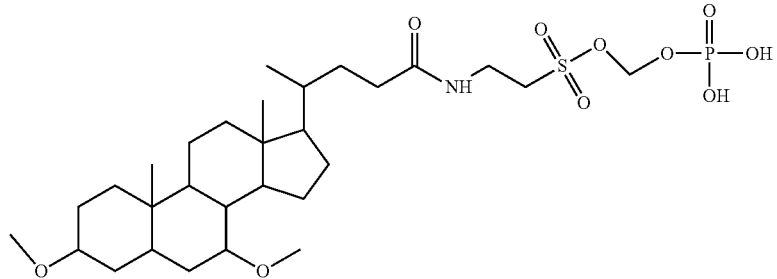
(1.48)
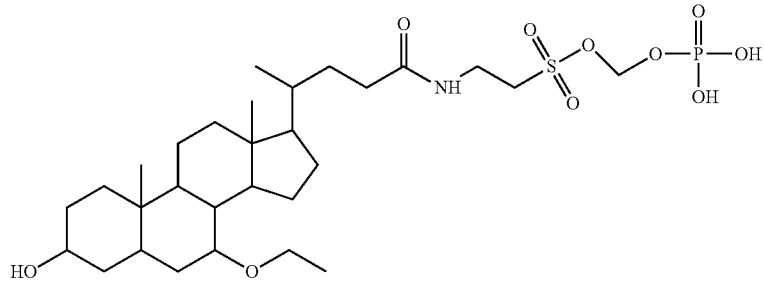
(1.49)
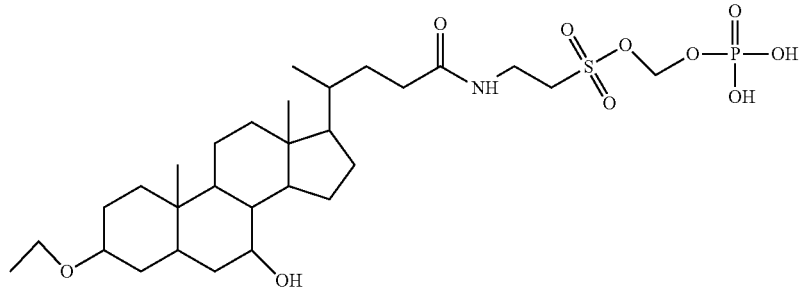
(1.50)

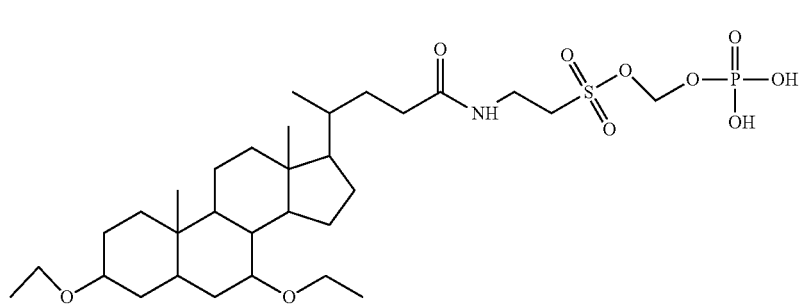
(1.51)
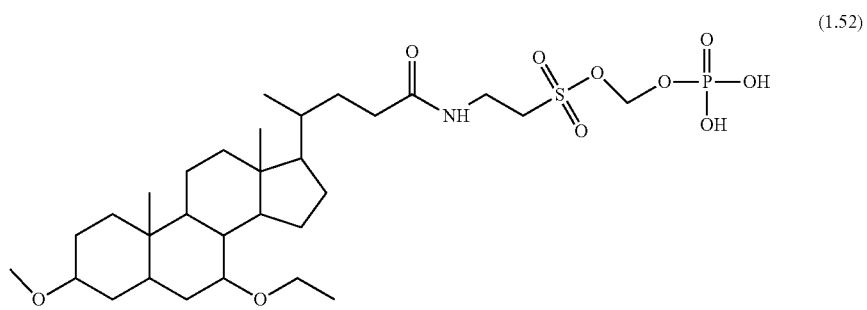
(1.52)
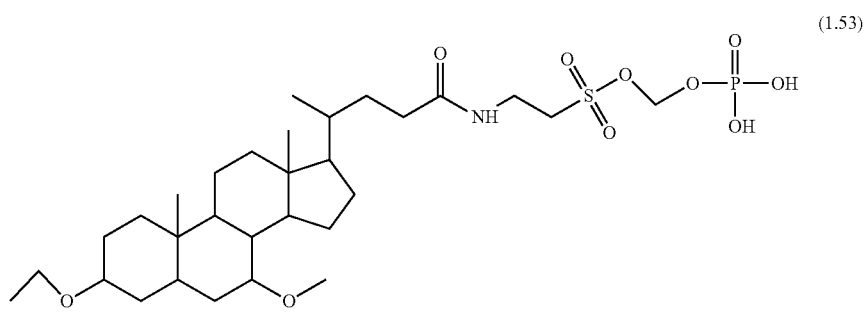
(1.53)
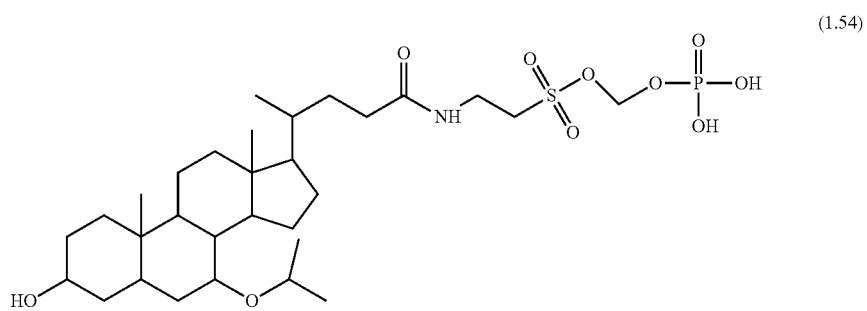
(1.54)
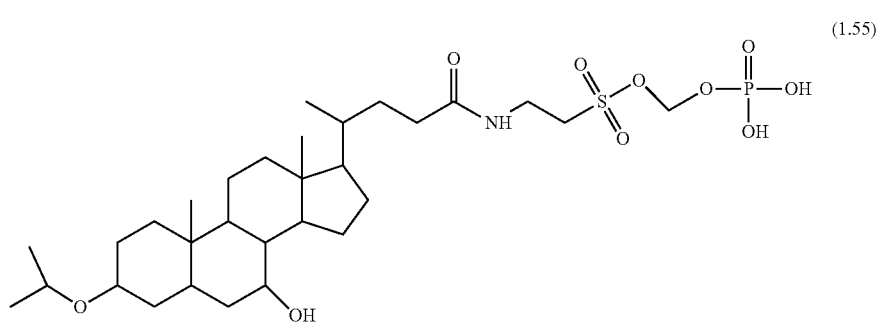
(1.55)

-continued
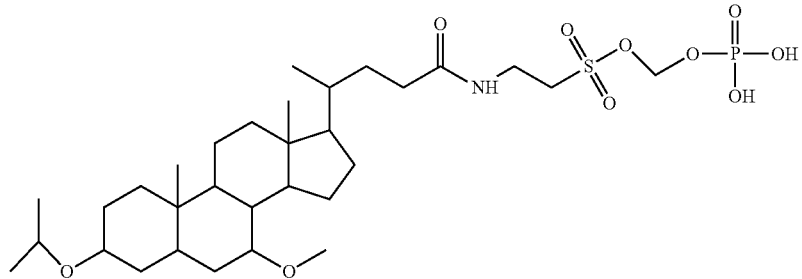
(1.56)
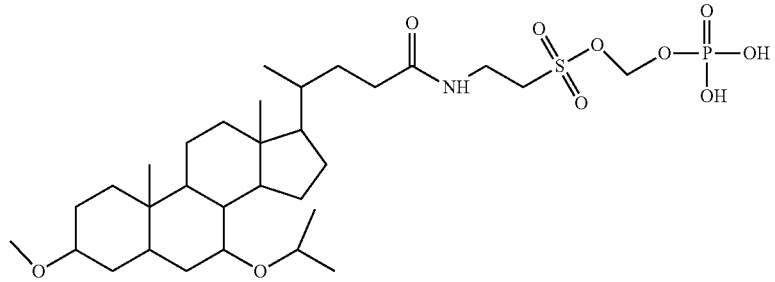
(1.57)
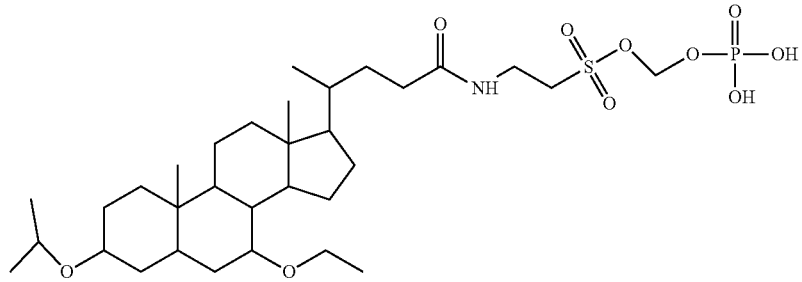
(1.58)
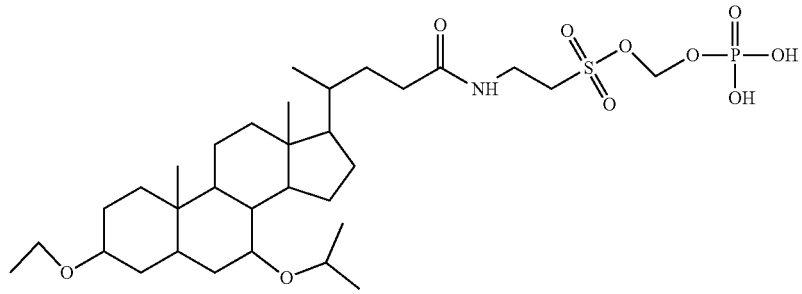
(1.59)
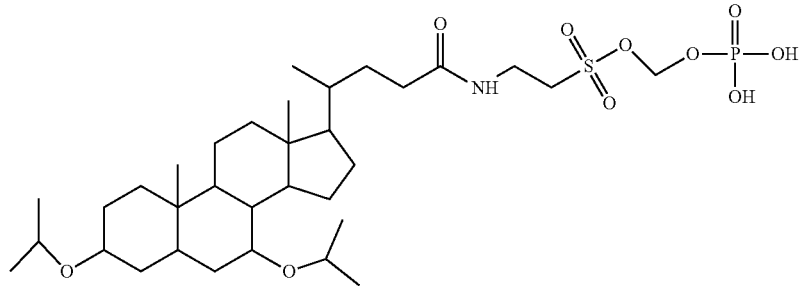
(1.60)
or a pharmaceutically acceptable salt thereof.

In some aspects of the Formula (2) the compound may have the formulae:
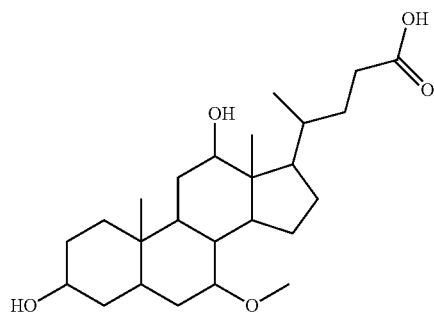
(1.61)
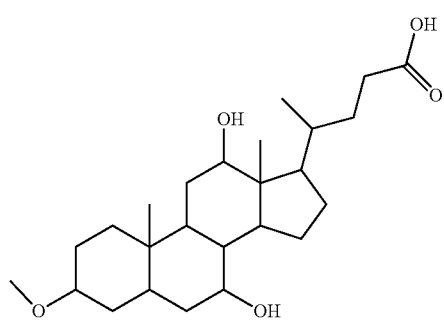
(1.62)
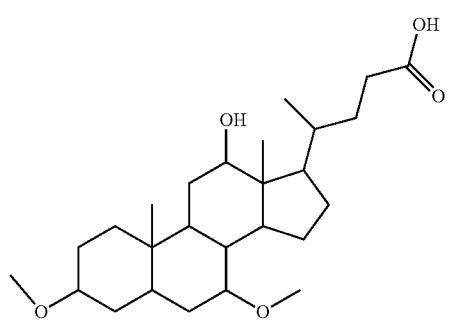
(1.63)
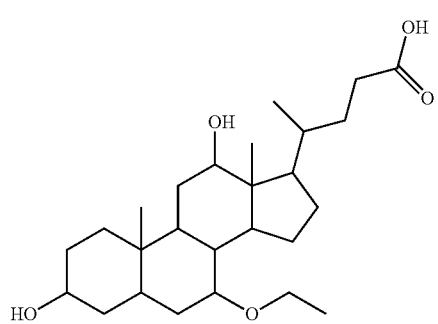
(1.64)
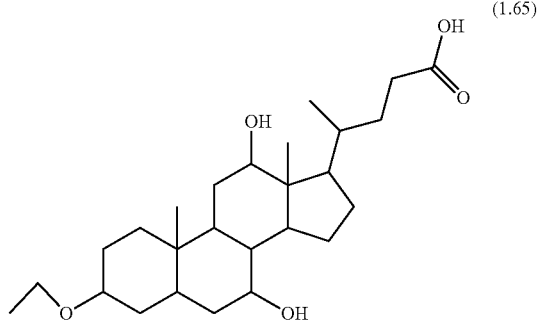
(1.65)
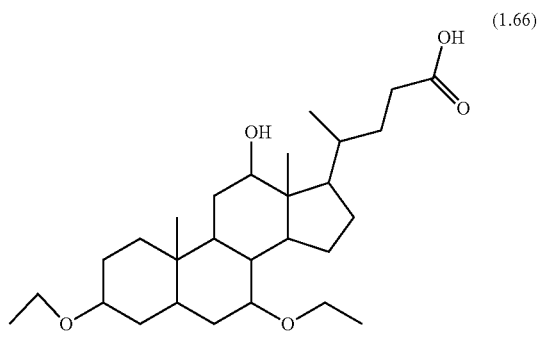
(1.66)
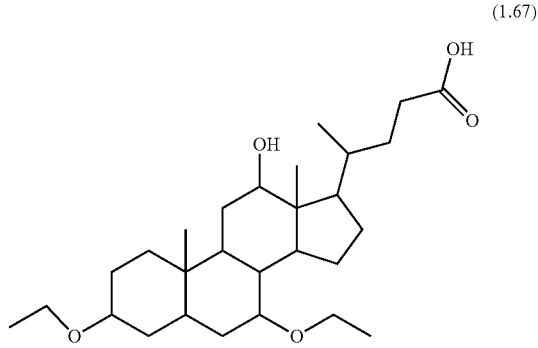
(1.67)
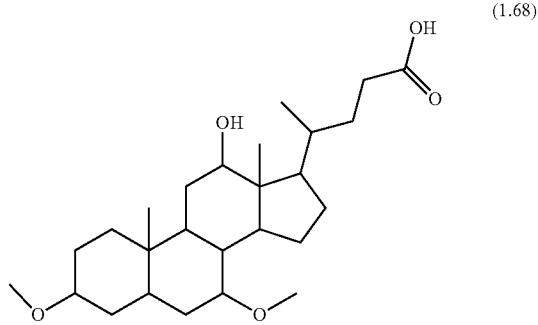
(1.68)

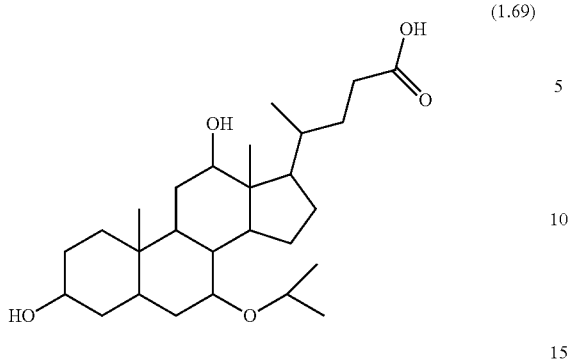
(1.69)
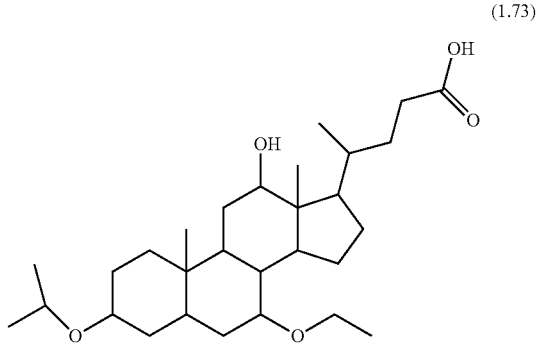
(1.73)
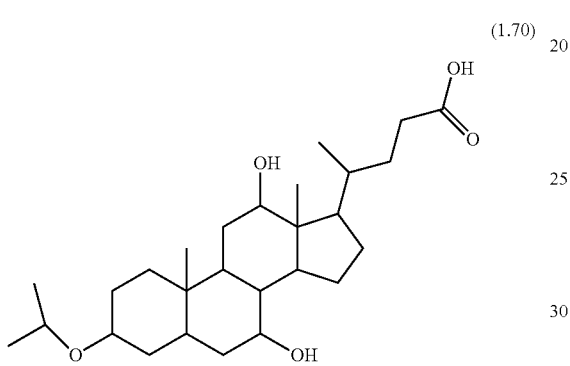
(1.70)
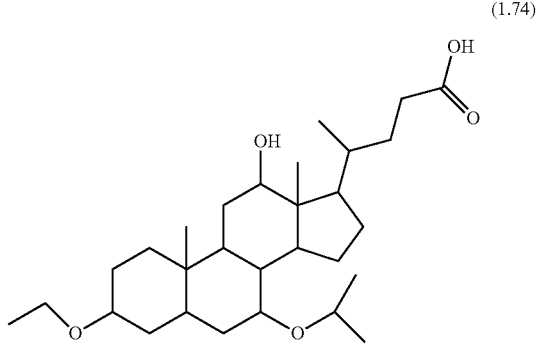
(1.74)
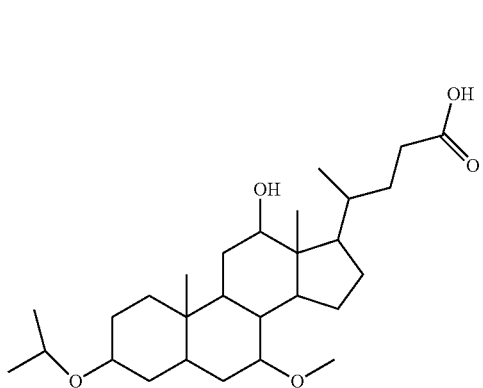
(1.71)
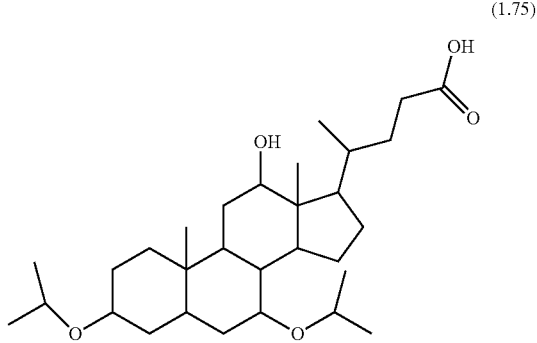
(1.75)
or a pharmaceutically acceptable salt thereof.
In some embodiments of the formulae (1.61-1.75) the compounds having the formulae:
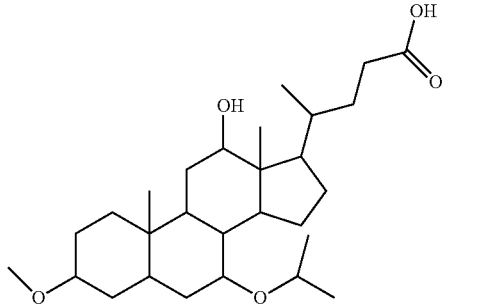
(1.72)
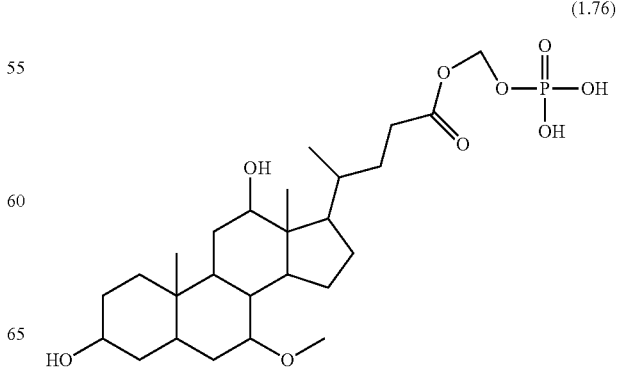
(1.76)

-continued
(1.77)
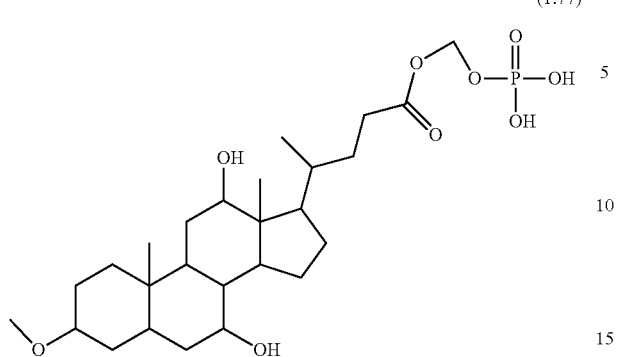
(1.81)
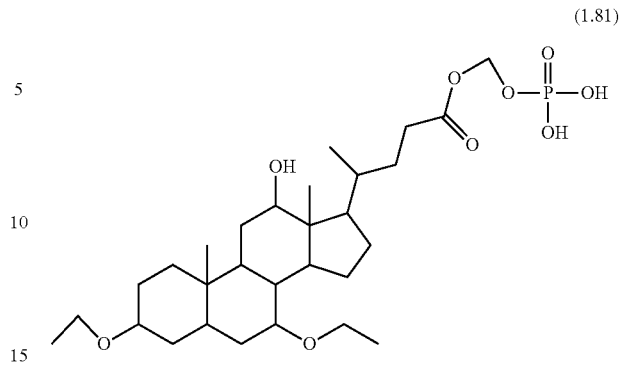
(1.78)
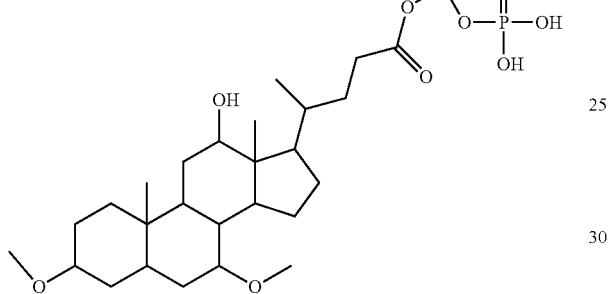
(1.82)
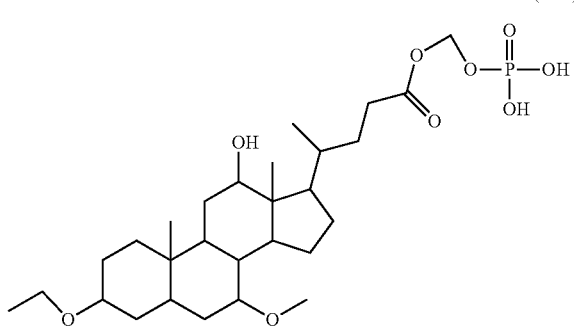
(1.79)
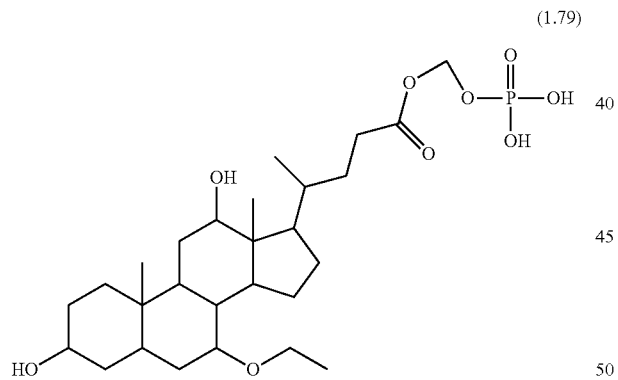
(1.83)
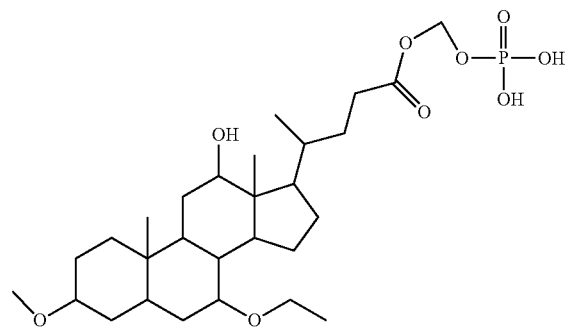
(1.80)
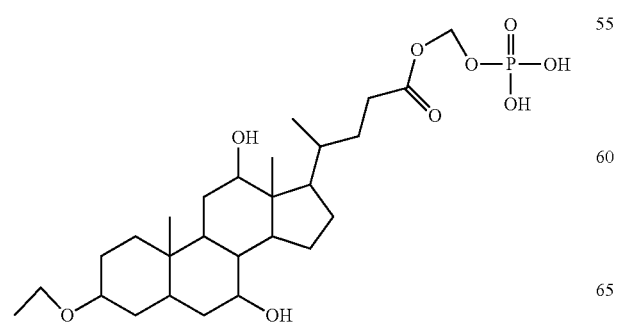
(1.84)
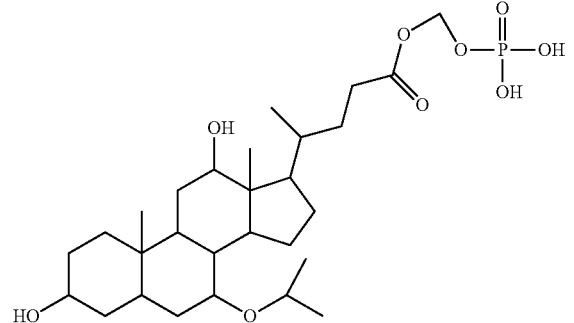

-continued (1.85)
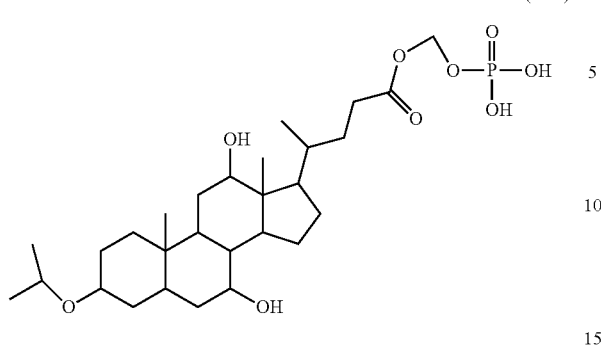

(1.86)
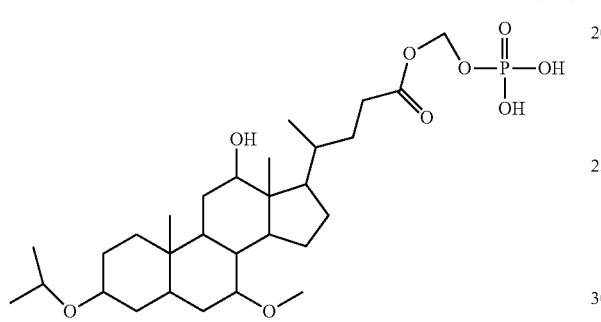

(1.87)
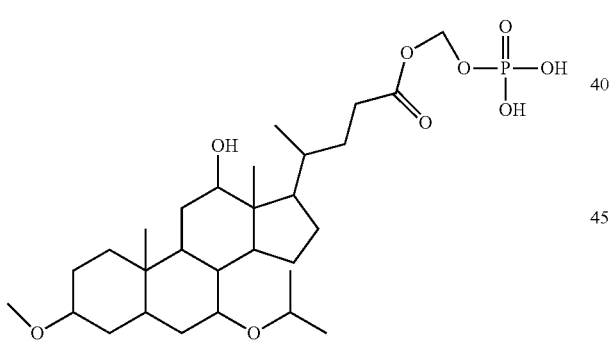

(1.88)
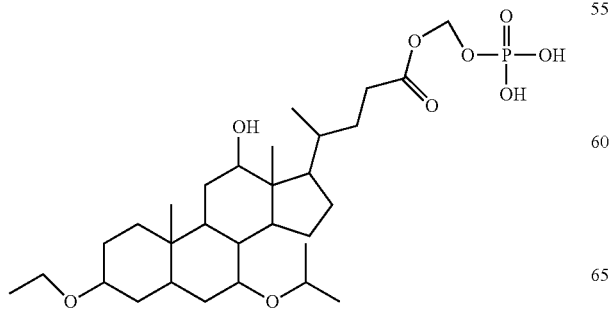

-continued (1.89)
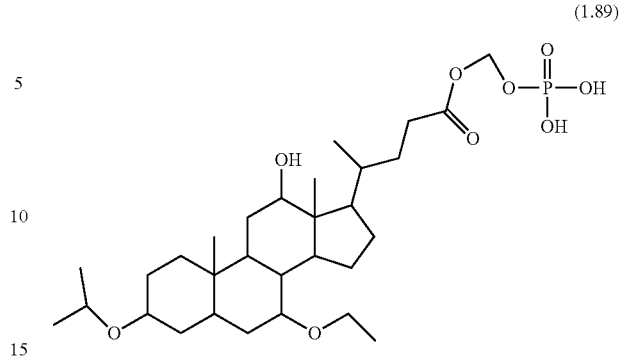

(1.90)
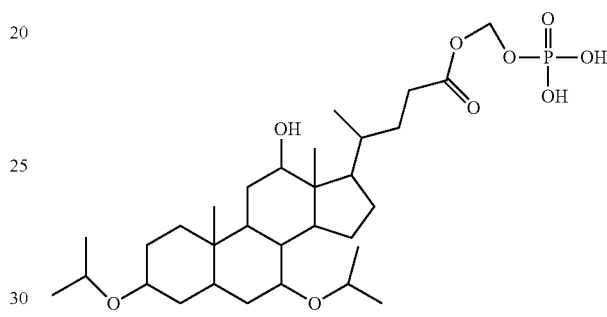

Preferably the structures in formulae (1.1-1.90) are dimethylated compounds. Dimethyl compounds can contain one methyl each at positions 3 and 7; or two methyl groups only at position 3; or two methyl groups only at position 7. Dimethylated compounds may provide superior conjugation chemistry and pharmacokinetics. Preferably the dimethyl structure is a phosphoryloxymethyl carboxyl (POMC) conjugate.

Preferably the compounds in formulae (1.1-1.90) are dimethylated or O-dimethylated at positions 3 and 7.

Preferably the compounds in formulae (1.1-1.90) are diethylated or O-diethylated at positions 3 and 7.

Preferably the compounds in formulae (1.1-1.90) are di-isopropyl or O-di-isopropyl derivatives at positions 3 and 7.

If the compounds (1.1-1.90) are monomethyl structures, preferably the structures are methylated at the position 7 and the methyl group is attached either directly to the carbon 7 or through an oxygen moiety (e.g. (O)-methyl). Preferably the monomethyl structure is a phosphoryloxymethyl carboxyl (POMC) conjugate.

If the compounds (1.1-1.90) are mono-isopropyl structures, preferably the structures are alkylated at the position 7 and the methyl group is attached either directly to the carbon 7 or through an oxygen moiety (e.g. (O)-methyl). Preferably the mono-isopropyl structure is a phosphoryloxymethyl carboxyl (POMC) conjugate.

In another aspect is a bile acid having the Formula (2'):

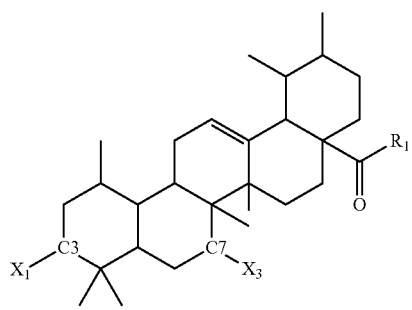

(2')

where $R_1$ is —OH or —O—($CH_2$)—O—P(O)($OH$)$_2$ or —OP(O)($OH$)$_2$; $X_1$ is —O($CH_3$) or —O($C_2H_5$) or —OCH($CH_3$)$_2$ or —OH or —H or —OP(O)($OH$)$_2$; $X_3$ is —O($CH_3$) or —O($C_2H_5$) or —($CH_3$) or —($C_2H_5$) or —OCH($CH_3$)$_2$. Carbons 3 and 7 are identified in Formula (2) above.

In one aspect of the Formula (2') $X_1$ is —O($CH_3$) and $X_3$ is —O($CH_3$) or —O($C_2H_5$) or —($CH_3$) or —($C_2H_5$) or —OCH($CH_3$)$_2$.

In another aspect of the Formula (2') $X_1$ is —O($C_2H_5$) and $X_3$ is —O($CH_3$) or —O($C_2H_5$) or —($CH_3$) or —($C_2H_5$) or —OCH($CH_3$)$_2$.

In another aspect of the Formula (2') $X_1$ is —OCH($CH_3$)$_2$ and $X_3$ is —O($CH_3$) or —O($C_2H_5$) or —($CH_3$) or —($C_2H_5$) or —OCH($CH_3$)$_2$.

In another aspect of the Formula (2') $X_1$ is —OH and $X_3$ is —O($CH_3$) or —O($C_2H_5$) or —($CH_3$) or —($C_2H_5$) or —OCH($CH_3$)$_2$.

In another aspect of the Formula (2') $X_1$ is —H and $X_3$ is —O($CH_3$) or —O($C_2H_5$) or —($CH_3$) or —($C_2H_5$) or —OCH($CH_3$)$_2$.

In another aspect of the Formula (2') $X_1$ is —OP(O)($OH$)$_2$ and $X_3$ is —O($CH_3$) or —O($C_2H_5$) or —($CH_3$) or —($C_2H_5$) or —OCH($CH_3$)$_2$.

In another aspect of the Formula (2') $X_1$ is —O($CH_3$) or —O($C_2H_5$) or —OCH($CH_3$)$_2$ or —OH or —H or —OP(O)($OH$)$_2$ and $X_3$ is —O($CH_3$).

In another aspect of the Formula (2') $X_1$ is —O($CH_3$) or —O($C_2H_5$) or —OCH($CH_3$)$_2$ or —OH or —H or —OP(O)($OH$)$_2$ and $X_3$ is —O($C_2H_5$).

In another aspect of the Formula (2') $X_1$ is —O($CH_3$) or —O($C_2H_5$) or —OCH($CH_3$)$_2$ or —OH or —H or —OP(O)($OH$)$_2$ and $X_3$ is —($CH_3$).

In another aspect of the Formula (2') $X_1$ is —O($CH_3$) or —O($C_2H_5$) or —OCH($CH_3$)$_2$ or —OH or —H or —OP(O)($OH$)$_2$ and $X_3$ is —O($C_2H_5$).

In another aspect of the Formula (2') $X_1$ is —O($CH_3$) or —O($C_2H_5$) or —OCH($CH_3$)$_2$ or - and $X_3$ is —H.

In another aspect of the Formula (2') $X_1$ is —O($CH_3$) or —O($C_2H_5$) or —OCH($CH_3$)$_2$ and $X_3$ is —OH.

In another aspect of the Formula (2') $X_1$ is —O($CH_3$) or —O($C_2H_5$) or —OCH($CH_3$)$_2$ H or and $X_3$ is —OP(O)($OH$)$_2$.

In another aspect of the Formula (2') at least one of the groups $X_1$ and $X_3$ contains a carbon atom.

In another aspect of the Formula (2') at least one of the $X_1$ or $X_3$ groups are alkylated.

In another aspect of the Formula (2') at least one of the $X_1$ or $X_3$ groups are O-alkylated.

In some embodiments of Formula (2') the compound may have the formulae:

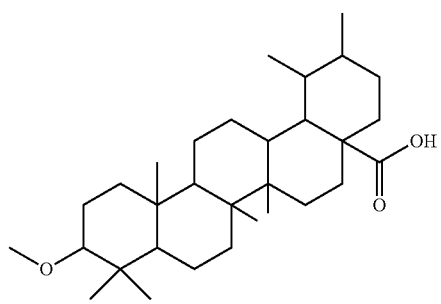

(2.1)

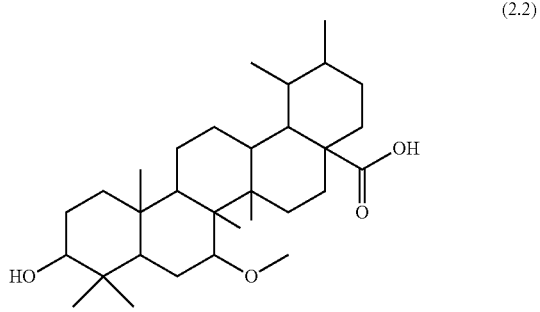

(2.2)

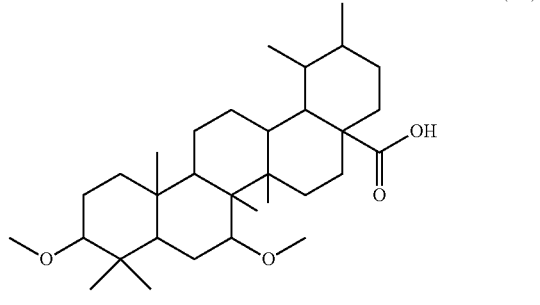

(2.3)

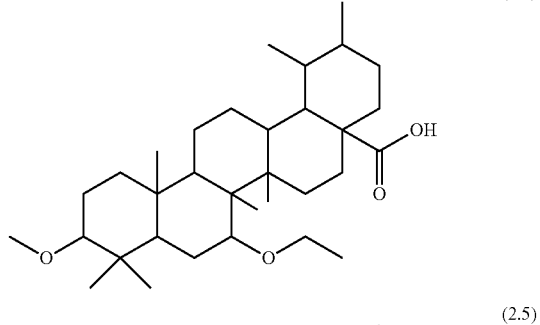

(2.4)

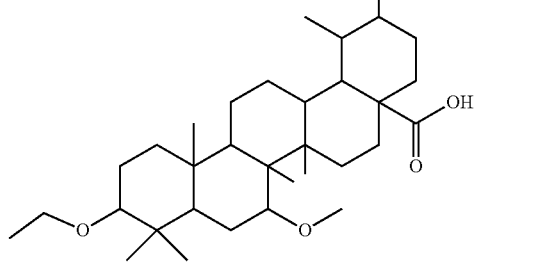

(2.5)

(2.6)
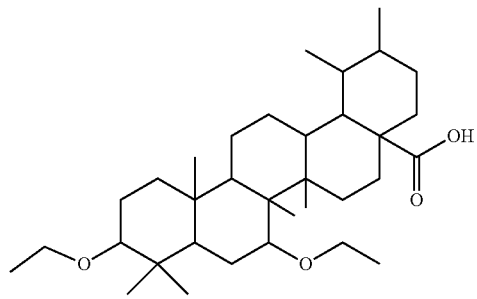
(2.7)
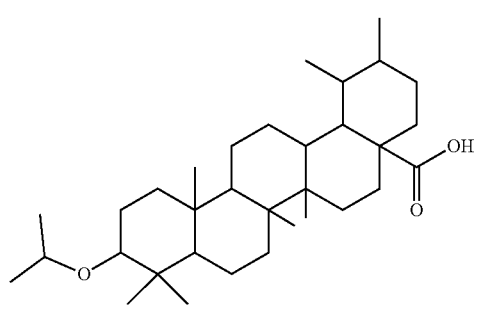
(2.8)
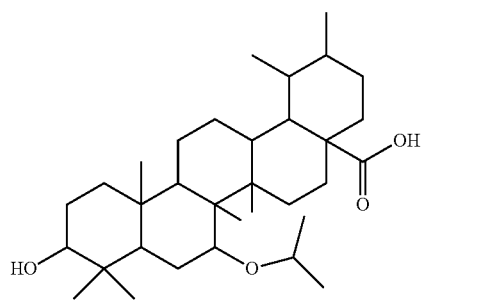
(2.9)
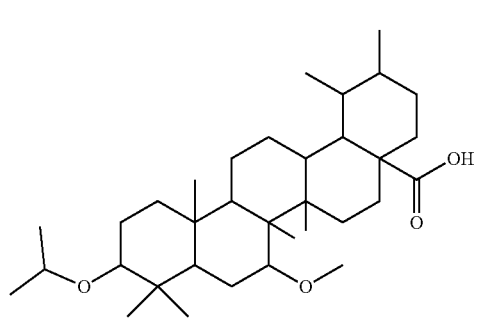
(2.10)
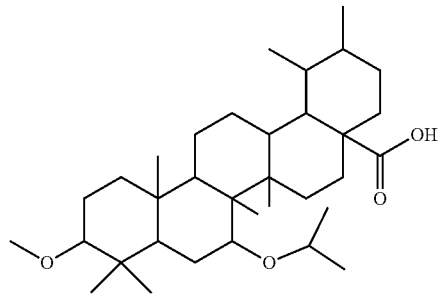
(2.11)
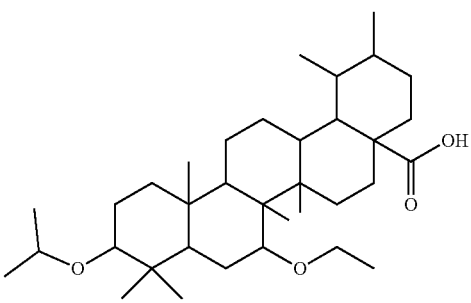
(2.12)
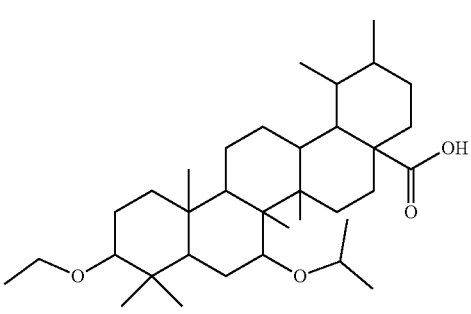
(2.13)
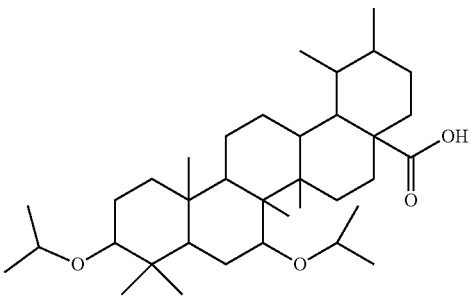
or a pharmaceutically acceptable salt thereof.
In some embodiments of the compounds (2.1-2.13) having the formulae:
(2.14)
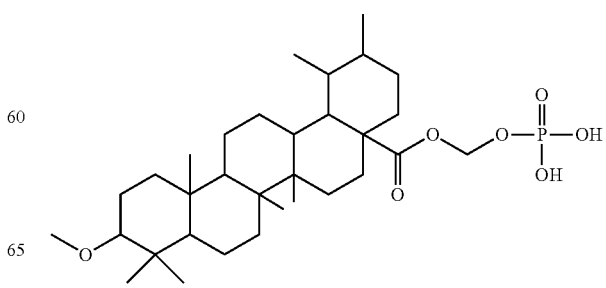

(2.15)
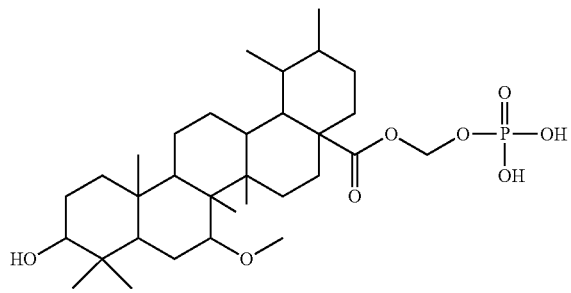
(2.16)
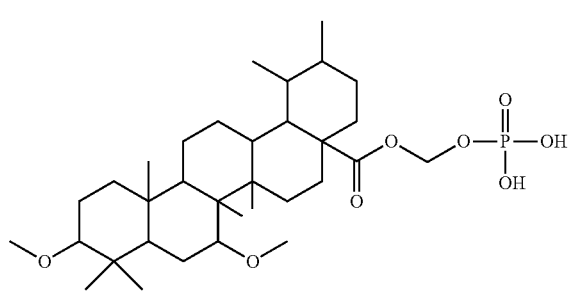
(2.17)
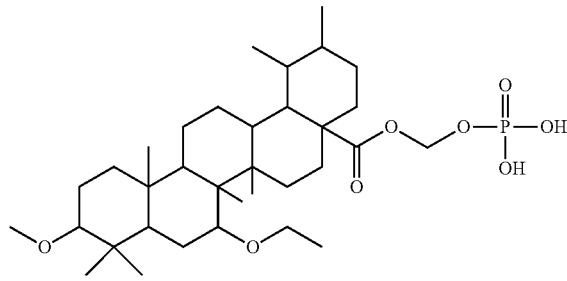
(2.18)
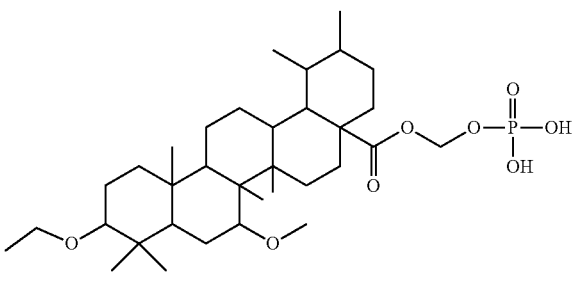
(2.19)
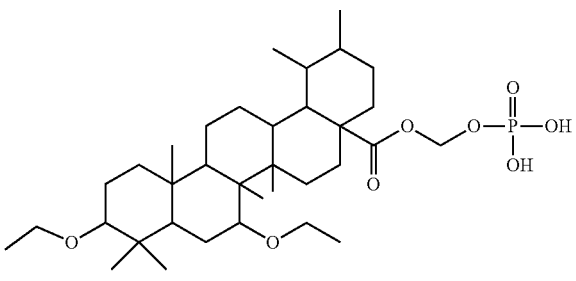
(2.20)
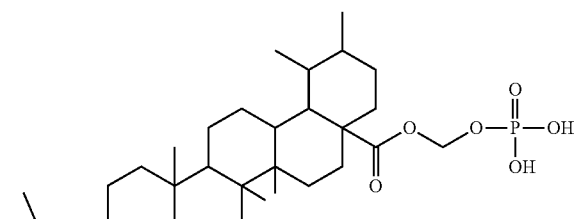
(2.21)
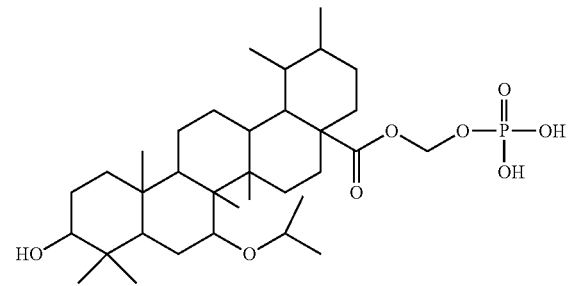
(2.22)
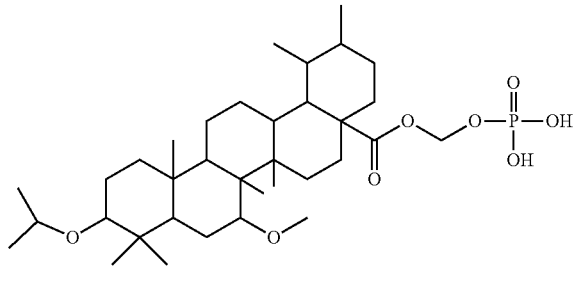
(2.23)
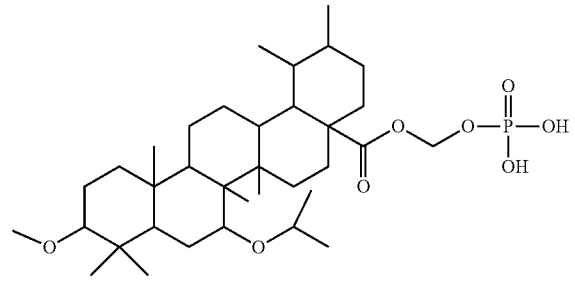
(2.24)
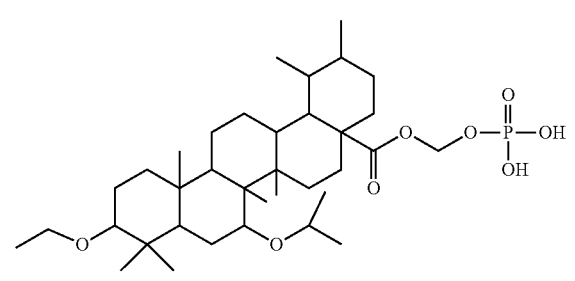

(2.25)

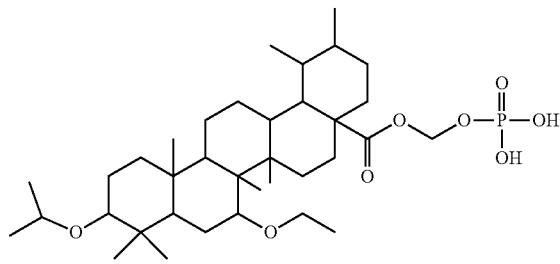

(2.26)

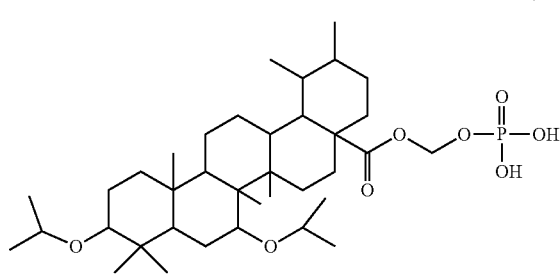

or a pharmaceutically acceptable salt thereof.

Preferably the structures in formulae (2.1-2.26) are dimethylated compounds. Dimethyl compounds can contain one methyl each at positions 3 and 7; or two methyl groups only at position 3; or two methyl groups only at position 7.

Preferably the compounds in formulae (2.1-2.26) are dimethylated or O-dimethylated at positions 3 and 7.

Preferably the compounds in formulae (2.1-2.26) are diethylated or O-diethylated at positions 3 and 7.

Preferably the compounds in formulae (2.1-2.26) are di-isopropyl or O-di-isopropyl derivatives at positions 3 and 7.

If the compounds (2.1-2.26) are monomethyl structures, preferably the structures are methylated at the position 7 and the methyl group is attached either directly to the carbon 7 or through an oxygen moiety (e.g. (O)-methyl). Preferably the monomethyl structure is a phosphoryloxymethyl carboxyl (POMC) conjugate.

If the compounds (2.1-2.26) are mono-isopropyl structures, preferably the structures are alkylated at the position 7 and the methyl group is attached either directly to the carbon 7 or through an oxygen moiety (e.g. (O)-methyl). Preferably the mono-isopropyl structure is a phosphoryloxymethyl carboxyl (POMC) conjugate.

In another aspect is a method of synthesizing a compound of Formula (2):

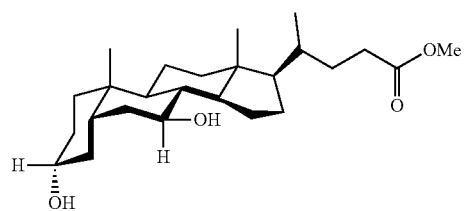

1

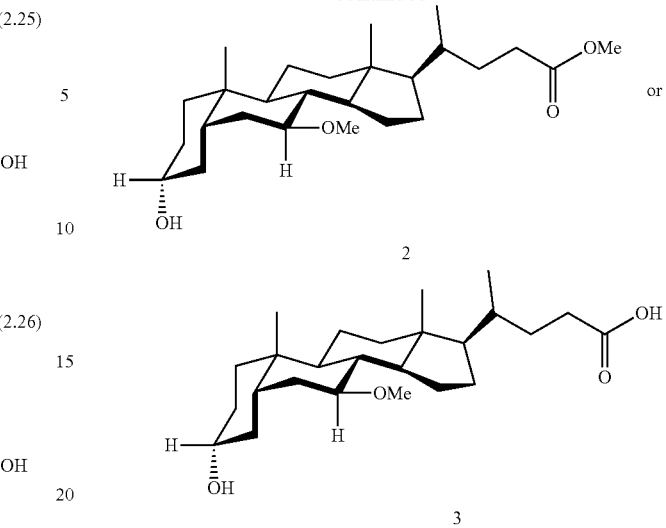

Figure 2:
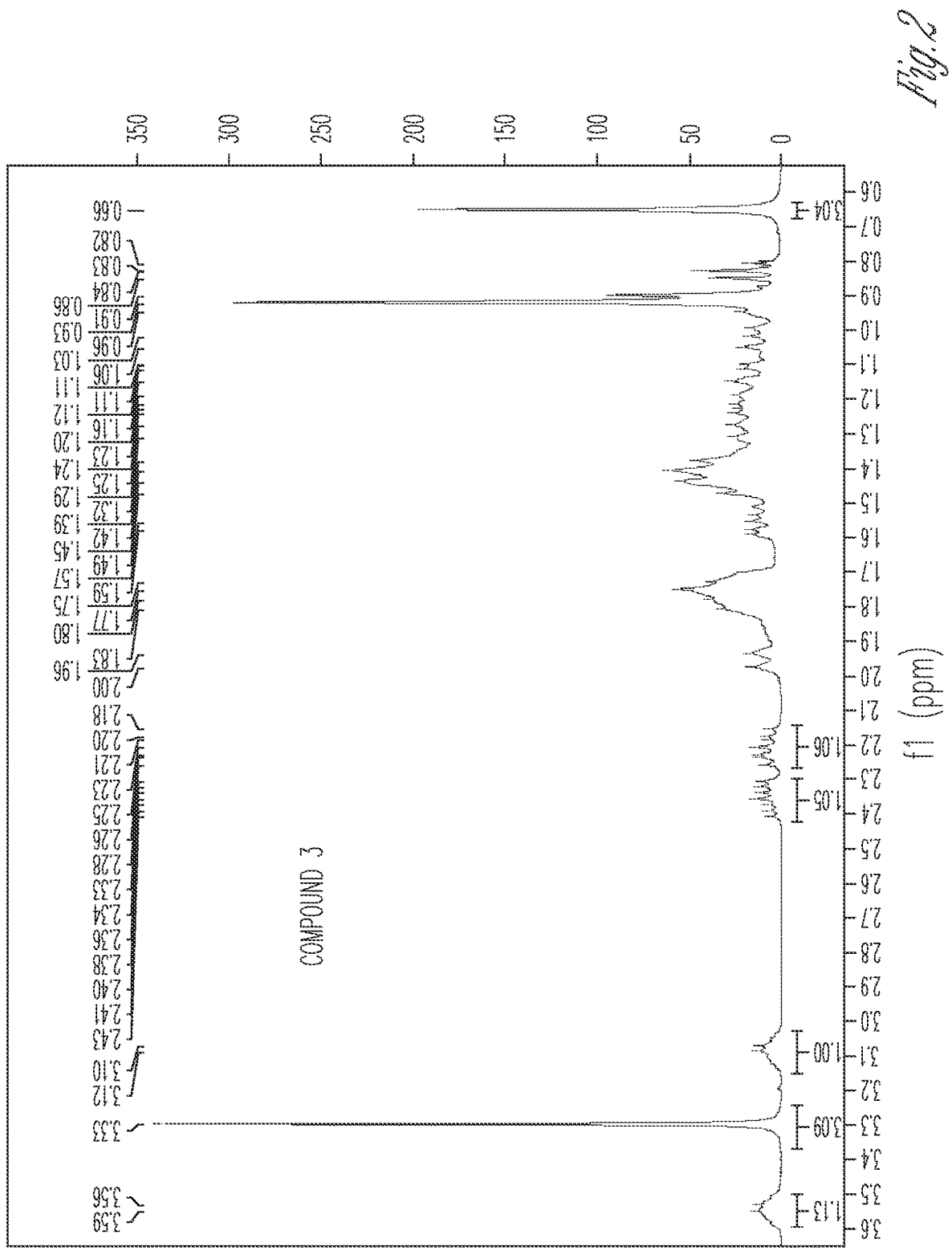
FIG. 2. $^1$H-NMR-Compound 3
FIG. 3. MS spectrum for compound 3 (ESI negative)
FIG. 4. Methylated UDCA prevents DCA-induced cytotoxicity and loss of cell viability in primary rat hepatocytes. Primary rat hepatocytes were incubated with 100 μM UDCA, methylated UDCA, or no addition (control) for 12 h. Cells were then exposed to 50 μM DCA for 40 h before processing for cytotoxicity activity, including LDH (top), and adenylate kinase (middle) assays, and cell viability (bottom). Results are expressed as means±SEM of at least three experiments. *$p<0.01$ from control; †$p<0.05$ and ‡$p<0.01$ from respective DCA.
Figure 3:
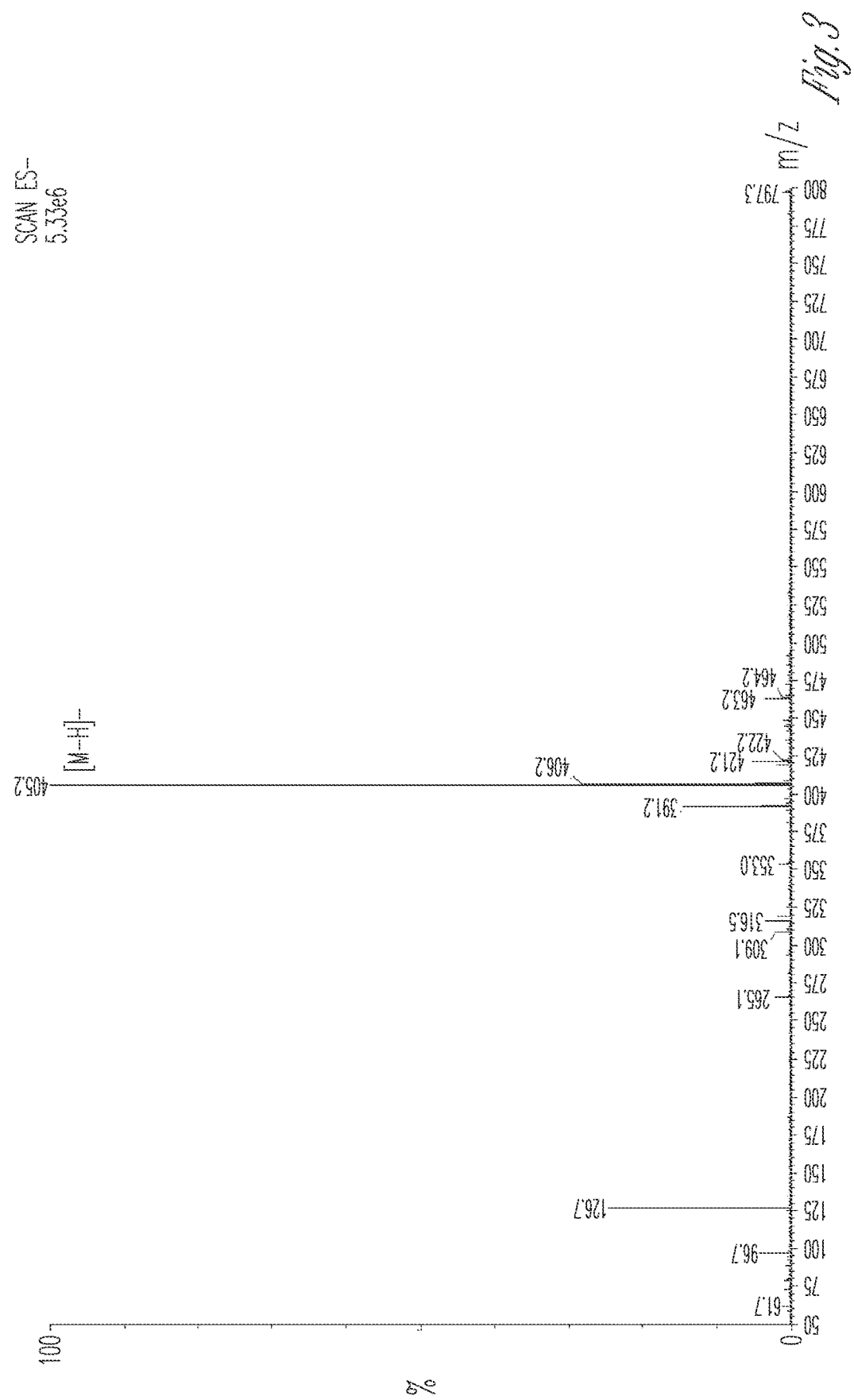

For the synthesis of the target molecule, the starting material used was the ester protected derivative 1. By means of this procedure, the expected ester product 2 was found to be hydrolysed to compound 3. We can observe by $^1$H-NMR (FIGS. 1 and 2) the disappearance of the ester methoxy group at 3.60 ppm observed for compound 1 (FIG. 1) and only one methoxy signal appeared at 3.33 ppm (FIG. 2); the protons 3 and 7 appear in separated signals at 3.59 and 3.12 for the product 3, indicating successful methylation with selectivity for one of the hydroxyls. Mass spectrometry using ESI negative mode showed the expected [M-H]$^-$ peak, confirming the presence of the free carboxylic acid (FIG. 3).

In another example is a method of synthesis of 3α-hydroxy,7β-methoxy-5β-cholan-24-oic acid.

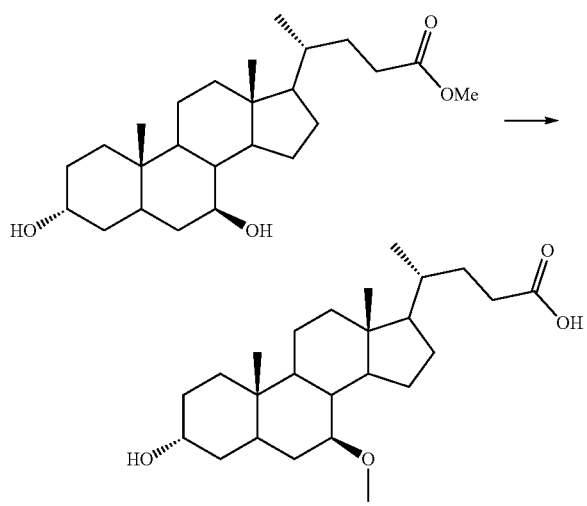

To prepare the LDA base in situ, a solution of DIPA in THF and nitrogen atmosphere, is cooled to −78° C. and TMEDA iadded followed by the dropwise addition of BuLi (0.66 mmol, 2.0 M solution in hexanes). Following the reaction, a solution of the starting material UDCA methyl ester in THF is added dropwise and the mixture i stirred at −78° C. i. MeI is then added and the reaction allowed to reach room temperature. The reaction is completed as judged by TLC. The mixture was carefully acidified to pH 1 with and the product is extracted with EtOAc. The organics are combined, dried over Na2SO4, filtered and concentrated under reduced pressure. The obtained residue was flash chromatographed using n-Hexane/EtOAc gradient to obtain the desired product as a white solid in 80% yield (72 mg, 0.18 mmol). MS (ESI-): m/z 405.2[M-H]–. 1H-NMR (CDCl3): 3.62-3.54 (m, 1H, H-3), 3.33 (s, 3H, OMe), 3.16-3.07 (m, 1H, H-7), 2.43-2.33 (m, 1H, H-23a), 2.28-2.18 (m, 1H, H-23b), 2.00-0.81 (m, XXX), 0.66 (s, 3H, CH3-18). 13C-NMR (CDCl3): 179.6 (C=O), 80.2 (CH), 71.5 (CH), 55.8 (CH), 55.7 (OCH3), 55.0 (CH), 43.9 (CH), 43.8 (CH), 42.5 (CH), 41.4 (Cq), 40.2 (CH2), 39.2 (CH), 37.0 (CH2), 35.4 (CH), 35.0 (CH2), 33.73 (CH2), 31.0 (CH2), 28.7 (CH2), 27.0 (CH2), 26.7 (CH2), 23.5 (CH3), 22.74 (Cq), 21.3 (CH2), 18.5 (CH3), 14.5 (Cq), 12.2 (CH3), 11.6 (Cq).

Abbreviations used herein are in accordance with conventional meaning with the chemical and biological arts. The chemical structures and formulae set forth herein are constructed consistent with the standard rules of chemical valency known in the chemical and biological arts.

Unless otherwise noted each carbon atom includes 4 covalent bonds and where a $2^{nd}$, 3rd or $4^{th}$ atom is not depicted it is a C—H bond.

Compositions

Typically, for preferred embodiments, the compound described herein can be formulated in pharmaceutical compositions. The pharmaceutical composition containing a compound of the present invention can be administered to a subject, typically a mammal such as a human subject, in a variety of forms adapted to the chosen route of administration. The formulations include those suitable for in vitro cell culture as well as, oral, rectal, vaginal, topical, nasal, ophthalmic, parenteral (including subcutaneous, intramuscular, intraperitoneal, intravenous, intrathecal, intraventricular, direct injection into brain tissue, etc.) administration.

The formulations may be conveniently presented in unit dosage form and may be prepared by any of the methods well known in the art of pharmacy. Typically, such methods include the step of bringing the active compound into association with a carrier, which can include one or more accessory ingredients. In general, the formulations are prepared by uniformly and intimately bringing the active compound into association with a liquid carrier, a finely divided solid carrier, or both, and then, if necessary, shaping the product into a desired formulation.

Formulations of the present invention suitable for oral administration may be presented as discrete units such as tablets, troches, capsules, lozenges, wafers, or cachets, each containing a predetermined amount of the apoptosis limiting compound as a powder, in granular form, incorporated within liposomes, or as a solution or suspension in an aqueous liquid or non-aqueous liquid such as a syrup, an elixir, an emulsion, or a draught.

The tablets, troches, pills, capsules, and the like may also contain one or more of the following: a binder such as gum tragacanth, acacia, corn starch, or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The compound may be incorporated into sustained-release preparations and devices if desired.

A compound suitable for use in the methods of the invention can also be incorporated directly into the food of a subject's diet, as an additive, supplement, or the like. Thus, the invention further provides a food product. Any food can be suitable for this purpose, although processed foods already in use as sources of nutritional supplementation or fortification, such as breads, cereals, milk, and the like, are convenient to use for this purpose.

Formulations suitable for parenteral administration conveniently comprise a sterile aqueous preparation of the desired compound, or dispersions of sterile powders comprising the desired compound, which are preferably isotonic with the blood of the subject. Isotonic agents that can be included in the liquid preparation include sugars, buffers, and salts such as sodium chloride. Solutions of the desired compound can be prepared in water, optionally mixed with a nontoxic surfactant. Dispersions of the desired compound can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the desired compound, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the desired compounds over a prolonged period can be achieved by including agents for delaying, for example, aluminum monostearate and gelatin.

Nasal spray formulations can include purified aqueous solutions of the desired compound with preservative agents and isotonic agents. Such formulations are preferably adjusted to a pH and isotonic state compatible with the nasal mucous membranes. Ophthalmic formulations are prepared by a similar method to the nasal spray, except that the pH and isotonic factors are preferably adjusted to match that of the eye. Formulations for rectal or vaginal administration may be presented as a suppository with a suitable carrier such as cocoa butter, or hydrogenated fats or hydrogenated fatty carboxylic acids.

In addition, a compound of the present invention can be modified by appropriate functionalities to enhance selective biological properties. Such modifications are known in the art and include those which increase biological penetration into a given biological system (e.g., blood, lymphatic system, central nervous system, brain), increase oral availability, increase solubility to allow administration by injection, alter metabolism and alter rate of exertion. In addition, a compound may be altered to pro-drug form such that the desired compound is created in the body of the subject as the result of the action of metabolic or other biochemical processes on the pro-drug. Some examples of pro-drug forms include ketal, acetal, oxime, and hydrazone forms of a compound that contains ketone or aldehyde groups.

Preferably, when a compound of the present invention can be delivered in vivo, the dosage level of the compound is on the order of about 10 milligrams to about 15 milligrams per kilogram of body weight per day. Preferably, the effective amount is on the order of about 500 milligrams to about 1000 milligrams per subject per day. When a compound of the present invention is delivered to a subject, the compound can be delivered in one or multiple dosages for injection, infusion, and/or ingestion.

EXAMPLES

The following examples illustrate further embodiments of the invention.

General Experimental

All chemicals and reagents were purchased from Aldrich and used without further purification. Dry solvents (THF and $CH_2Cl_2$) were dispensed under argon from solvent purification systems. Thin layer chromatography was conducted on silica gel 250 micron, F254 plates and were visualized with and $I_2$ or developing the plate with anisaldehyde stain, using EtOAc or EtOAc/n-Hexane mixtures as eluant. Visualization of the TLC spots was additionally achieved by spraying with a 10% solution of sulfuric acid in methanol followed by heating. Silica gel was acquired from Merck (60 G, 0.040-0.063 mm). The crude compounds were purified by a Combiflash Rf chromatography system (Teledyne Technologies, Inc., Thousand Oaks, CA) unless specified otherwise. $^1H$- and $^{13}C$-NMR spectra were recorded on a Bruker Avance 400 (400 MHz and 100 MHz, respectively) and were calibrated using residual undeuterated solvent as an internal reference ($CHCl_3$ @ 7.27 ppm $^1H$-NMR, 77.23 ppm $^{13}C$-NMR and DMSO @ 2.50 ppm $^1H$-NMR, 39.51 ppm $^{13}C$-NMR). The following abbreviations were used to explain NMR peak multiplicities: s=singlet, d=doublet, t=triplet, dd=double doublet, m=multiplet. Coupling constants (J) are reported in Hz.

Compound Synthesis

Example 1: Synthesis of Ursodeoxycholic Acid 7-Fluoro-Analog 6

Compound numbering in this example refers to Scheme 1 shown below.

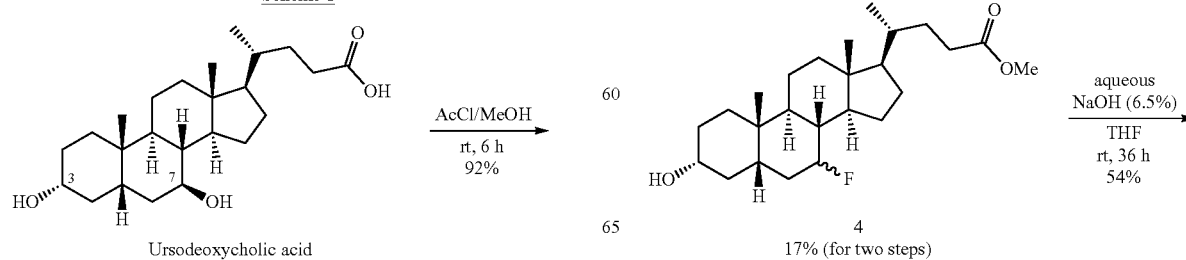

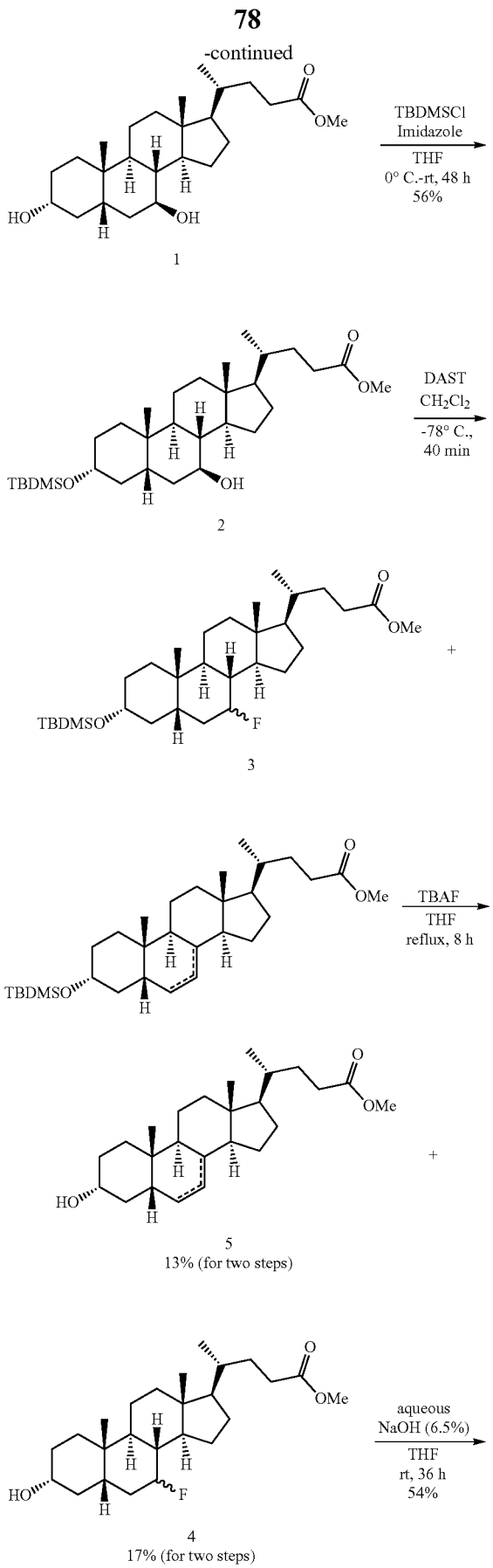

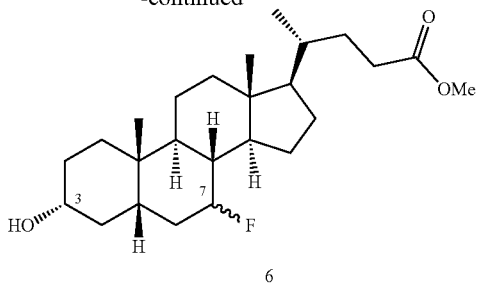

6

Ursodeoxycholic acid 7-fluoro-analog 6 synthesis (scheme 1) started from the protection of commercially available ursodeoxycholic acid as its methyl ester 1. To achieve the fluorination at C-7 position, C-3 hydroxy group was protected as corresponding silylether 2 with TBDMSCl and imidazole. Then the fluorination with DAST(diethylaminosulfur trifluoride) at −78° C. produced the C-7 fluoroester and olefins as inseparable mixture 3. Deprotection of 3 with TBAF resulted the diastereomeric mixture of C-7 fluoroesters 4. At this stage, the isomeric olefins mixture 5 was separated by chromatography. Ester hydrolysis of 4 provided the 6 as 1:1 diastereomeric mixture.

Ester 1: To a suspension of ursodeoxycholic acid (4.02 g, 10.23 mmol) in anhydrous methanol (60 mL), was added acetyl chloride (0.5 mL) dropwise at 0° C. and then left for stirring at room temperature 6 h. The reaction was diluted with water (60 mL) and quenched with saturated NaHCO$_3$ (60 mL). Organic volatiles were evaporated and then extracted with ethyl acetate (3×60 mL). Combined organic fractions were washed with brine (60 mL) and dried over Na$_2$SO$_4$. Evaporation of volatiles in vacuo yielded the ester 1 (3.830 g, 92%) as white solid. R$_f$=0.32 (1:1 hexanes:EtOAc); $^1$H NMR (400 MHz, CDCl$_3$): δ 3.64 (s, 3H), 3.61-3.51 (m, 2H), 2.34 (ddd, J=15.3, 10.1, 5.0 Hz, 1H), 2.20 (ddd, J=15.6, 9.5, 6.5 Hz, 1H), 2.01-1.73 (m, 8H), 1.69-1.53 (m, 4H), 1.51-1.19 (m, 11H), 1.17-0.99 (m, 3H), 0.95-0.89 (m, 6H), 0.66 (s, 3H); $^{13}$C NMR (101 MHz, CDCl$_3$): δ 174.89, 71.49, 71.43, 55.94, 55.09, 51.67, 43.91, 43.88, 42.62, 40.31, 39.39, 37.48, 37.09, 35.44, 35.10, 34.23, 31.24, 31.18, 30.46, 28.77, 27.06, 23.57, 21.34, 18.54, 12.29.

TBDMS ether 2: To a solution of 1 (2.010 g, 4.94 mmol) and imidazole (0.588 g, 8.65 mmol, 1.75 equiv) in anhydrous THF (50 mL) was slowly added the TBDMSCl (0.745 g, 4.94 mmol, 1.0 equiv) in THF (50 mL) by additional funnel over two hours at 0° C. Then the reaction was stirred at room temperature for 48 h. Water was (60 mL) was added to the reaction and extracted with ethyl acetate (3×60 mL). The combined organic fractions were washed with brine (60 mL), dried over Na$_2$SO$_4$, filtered, and evaporated in vacuo. The crude residue was purified by flash column chromatography (silica gel, 0-100% ethyl acetate in hexanes) to give 2 (1.451 g, 56%) as white solid. R$_f$=0.60 (4:1 hexanes:EtOAc); $^1$H NMR (400 MHz, CDCl$_3$): δ 3.66 (s, 3H), 3.64-3.49 (m, 2H), 2.35 (ddd, J=15.1, 10.1, 4.9 Hz, 1H), 2.26-2.16 (m, 1H), 1.97 (dt, J=12.6, 3.3 Hz, 1H), 1.94-1.85 (m, 1H), 1.78 (dtd, J=12.5, 10.9, 5.6 Hz, 4H), 1.64-1.52 (m, 4H), 1.51-1.18 (m, 12H), 1.16-0.97 (m, 3H), 0.94-0.91 (m, 6H), 0.88 (s, 9H), 0.67 (s, 3H), 0.05 (s, 6H); $^{13}$C NMR (101 MHz, CDCl$_3$): δ 174.90, 72.58, 71.56, 55.81, 55.10, 51.68, 43.98, 43.94, 42.81, 40.28, 39.18, 38.05, 37.14, 35.45, 35.36, 34.28, 31.26, 31.22, 31.06, 28.79, 27.09, 26.14, 23.60, 21.36, 18.57, 18.49, 12.30, −4.42.

3: DAST (76 micro-L, 0.58 mmol, 1.0 equiv) was added to 2 (302 mg, 0.58 mmol) in CH$_2$Cl$_2$ (6 mL) at −78° C. and stirred for 40 minutes at the same temperature. Upon completion, the reaction was quenched with water (5 mL) at −78° C. and warmed to room temperature. Organic fraction was separated and then aqueous phase was extracted with additional CH$_2$Cl$_2$ (2×10 mL). Combined organic fractions were washed with brine (20 mL), dried over Na$_2$SO$_4$, filtered and evaporated the volatiles in vacuo. The crude residue was purified by flash column chromatography (silica gel, 0-30% ethyl acetate in hexanes) to give 3 as inseparable mixture (168 mg), which was used for next step without further purification.

Fluoroester 4 & olefin mixture 5: To mixture 3 (150 mg) in anhydrous THF (12 mL) were added water (12 L) and TBAF (120 μL) and heated to reflux for 8 hours. Upon completion of the reaction, saturated NH$_4$Cl (10 mL) was added and then extracted with CH$_2$Cl$_2$ (3×10 mL). Combined organic fractions were washed with brine (20 mL), dried over Na$_2$SO$_4$, filtered and volatiles were evaporated in vacuo. The crude residue was purified by flash column chromatography (silica gel, 0-30% ethyl acetate in hexanes) to give fluoroester 4 (40 mg, 17% for two steps) as white solid along with olefin mixture 5 (29 mg, 13% for two steps).

Fluoroester 4: R$_f$=0.24 (7:3 hexanes:EtOAc); $^1$H NMR (400 MHz, CDCl$_3$): 4.49 (ddd, J=11.5, 9.7, 5.4 Hz, 0.5H), 4.37 (ddd, J=11.5, 9.7, 5.4 Hz, 0.5H), 3.67 (s, 3H), 3.59 (tt, J=9.7, 4.6 Hz, 1H), 2.36 (ddd, J=15.2, 10.1, 5.0 Hz, 1H), 2.23 (ddd, J=15.6, 9.6, 6.5 Hz, 1H), 2.00 (dq, J=11.5, 4.7, 4.0 Hz, 1H), 1.93-1.64 (m, 8H), 1.60-1.50 (m, 3H), 1.48-1.40 (m, 3H), 1.40-1.20 (m, 8H), 1.13-1.03 (m, 2H), 0.98 (s, 3H), 0.93 (d, J=6.4 Hz, 3H), 0.68 (s, 3H); $^{13}$C NMR (101 MHz, CDCl$_3$): δ 174.94, 94.94, 93.24, 71.50, 55.32, 51.71, 43.44, 42.68, 42.56, 41.97, 41.81, 40.11, 38.86, 38.77, 37.44, 35.50, 34.82, 34.26, 34.03, 33.83, 31.29, 31.24, 30.49, 29.91, 28.60, 26.22, 26.16, 23.50, 21.23, 18.57, 12.21; $^{19}$F NMR (376 MHz, CDCl$_3$): δ 172.58, 172.45

Olefin mixture 5: R$_f$=0.33 (7:3 hexanes:EtOAc); $^1$H NMR (400 MHz, CDCl$_3$): δ 5.55-5.42 (m, 0.2H), 5.11 (dq, J=6.0, 2.0 Hz, 0.4H), 3.71-3.56 (m, 4H), 2.38 (dddt, J=17.8, 10.3, 5.1, 3.1 Hz, 2H), 2.28-2.14 (m, 2H), 2.06-1.69 (m, 8H), 1.60-1.20 (m, 14H), 1.17-1.08 (m, 1H), 0.94 (dt, J=5.8, 4.0 Hz, 3H), 0.88-0.81 (m, 4H), 0.55 (s, 1H); $^{13}$C NMR (101 MHz, CDCl$_3$): δ 174.99, 141.82, 137.49, 127.25, 115.64, 71.96, 71.52, 56.79, 55.97, 55.26, 51.71, 43.95, 42.87, 42.47, 41.11, 40.09, 37.87, 37.49, 36.91, 36.47, 36.30, 36.17, 35.99, 35.59, 34.89, 34.82, 34.21, 33.72, 31.65, 31.32, 31.22, 31.17, 31.04, 29.91, 28.87, 28.14, 27.59, 27.24, 26.03, 25.00, 24.71, 23.88, 23.06, 21.87, 20.79, 20.76, 19.65, 18.94, 18.65, 18.47, 18.32, 12.25, 12.11.

6: To compound 4 (50 mg) in THF (1.5 mL) was added 6.5% aqueous NaOH (0.5 mL) at room temperature and allowed to stir for 36 h. 1N HCl (5 mL) was added to the reaction and extracted with EtOAc (3×10 mL). Combined organic fractions were washed with water (15 mL), brine (15 mL), dried over Na$_2$SO$_4$, filtered and evaporated in vacuo. The crude residue was purified by flash column chromatography (silica gel, 0-10% methanol in dichloromethane) to give 6 (26 mg, 54%) as white solid. R$_f$=0.30 (9:1 CH$_2$Cl$_2$:CH$_3$OH); $^1$H NMR (400 MHz, DMSO-d$_6$): 11.94 (s, 1H), 4.47 (dd, J=9.8, 5.1 Hz, 1.5H), 4.37 (td, J=10.5, 5.3 Hz, 0.5H), 3.31 (s, 1H), 2.23 (ddd, J=15.2, 9.7, 5.4 Hz, 1H), 2.10 (ddd, J=15.8, 9.4, 6.9 Hz, 1H), 1.95 (d, J=12.2 Hz, 1H), 1.81 (tt, J=16.7, 6.9 Hz, 4H), 1.58-1.31 (m, 9H), 1.28-1.05 (m, 8H), 0.90 (q, J=7.4, 6.5 Hz, 6H), 0.63 (s, 3H); $^{13}$C NMR (101 MHz, DMSO-d$_6$): δ 174.86, 94.33, 92.64, 69.49, 54.60, 54.33, 42.68, 41.89, 41.77, 41.37, 41.21, 37.99, 37.90, 37.01, 34.73, 34.37, 33.65, 33.49, 30.72, 30.70, 30.11, 27.88, 25.83, 25.79, 23.06, 20.54, 18.21, 11.74; $^{19}$F NMR (376 MHz, DMSO-d$_6$): δ 170.80, 170.67

Example 2: Synthesis of Ursodeoxycholic Acid 7-Fluoro-Analog 7

Compound numbering in this example refers to Scheme 2 shown below.

The 3,7-difluoro analog 7 was prepared from ursodeoxycholic acid using the procedure for the synthesis of compound 3 described in Example 1 above (Scheme 2).

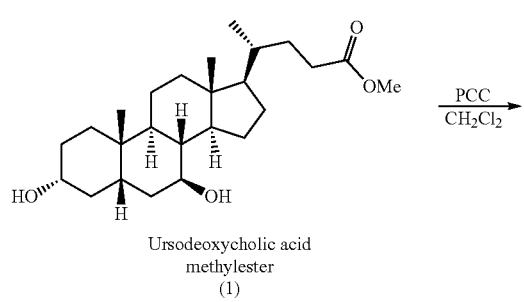

Example 3: Synthesis of Ursodeoxycholic Acid 7-Fluoro-Analog 10

Compound numbering in this example refers to Scheme 3 shown below.

The 3,7-tetrafluoro analog 10 was prepared from methyl ester 1 as shown in Scheme 3 below. PCC oxidation of 1 furnished the diketone 8, which was subjected to fluorination using the procedure for the synthesis of compound 3 as described in Example 1 above. Methyl ester hydrolysis provided the tetrafluoro analog 10.

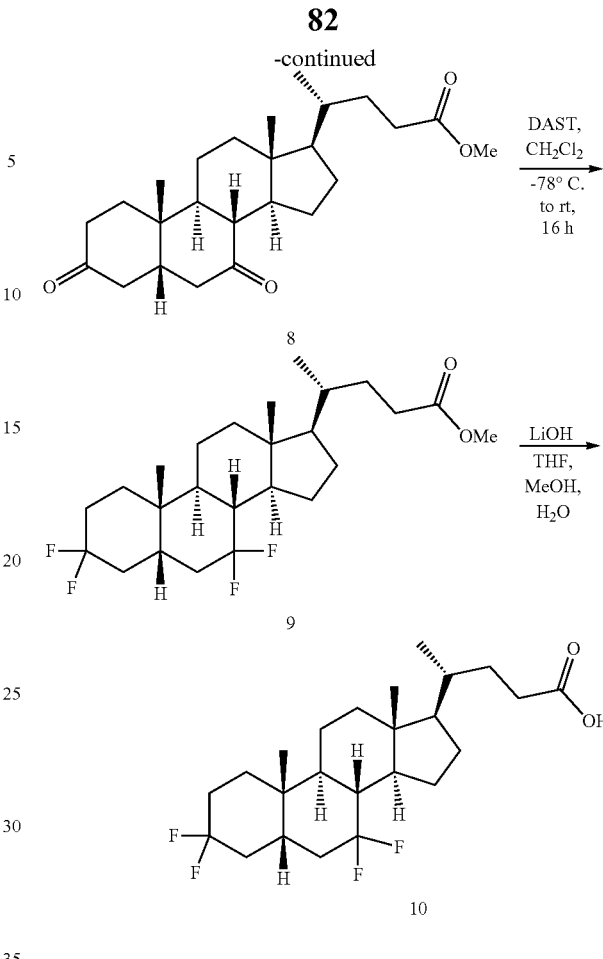

Methyl-3α,7β-dihydroxy-5β-cholanoate (2):

To a solution of commercially available 3α,7 β-dihydroxy-5β-cholanic acid (500 mg, 1.27 mmol) in MeOH (40 mL) was added p-toluenosulfonic acid and the mixture was refluxed under nitrogen atmosphere for 3 h. The reaction mixture was allowed to reach room temperature, poured into water (100 mL) and the product was extracted with EtOAc (3×50 mL). The organics were combined, dried over anhydrous sodium sulfate, filtered and concentrated in the rotatory evaporator to yield a colorless oil (499 mg, 1.22 mmol, 97%). The residue was pure as judged by TLC and was reacted without further purification.

3α-hydroxy,7β-methoxy-5β-cholan-24-oic acid (3):

To prepare the LDA base in situ, a solution of DIPA (0.66 mmol) in THF (2 mL) and nitrogen atmosphere, was cooled to −78° C. and TMEDA (0.66 mmol) was added followed by the dropwise addition of BuLi (0.66 mmol, 2.0M solution in hexanes). After 1 h, a solution of the starting material UDCA methyl ester, 2, (0.22 mmol, 90 mg) in THF (3 mL) was added dropwise and the mixture was stirred at −78° C. for 1 h. MeI (0.24 mmol) was then added and the reaction was allowed to reach room temperature. After 1 h, the reaction was completed as judged by TLC. The mixture was carefully acidified to pH 1 with HCl (10%) and the product was extracted with EtOAc (3×15 mL). The organics were combined, dried over Na2SO4, filtered and concentrated under reduced pressure. The obtained residue was flash chromatographed using n-Hexane/EtOAc gradient to obtain the desired product as a white solid in 80% yield (72 mg, 0.18 mmol). MS (ESI-): m/z 405.2[M-H]$^-$. $^1$H-NMR (CDCl$_3$): 3.62-3.54 (m, 1H, H-3), 3.33 (s, 3H, OMe), 3.16-3.07 (m, 1H, H-7), 2.43-2.33 (m, 1H, H-23a), 2.28-2.18 (m, 1H,

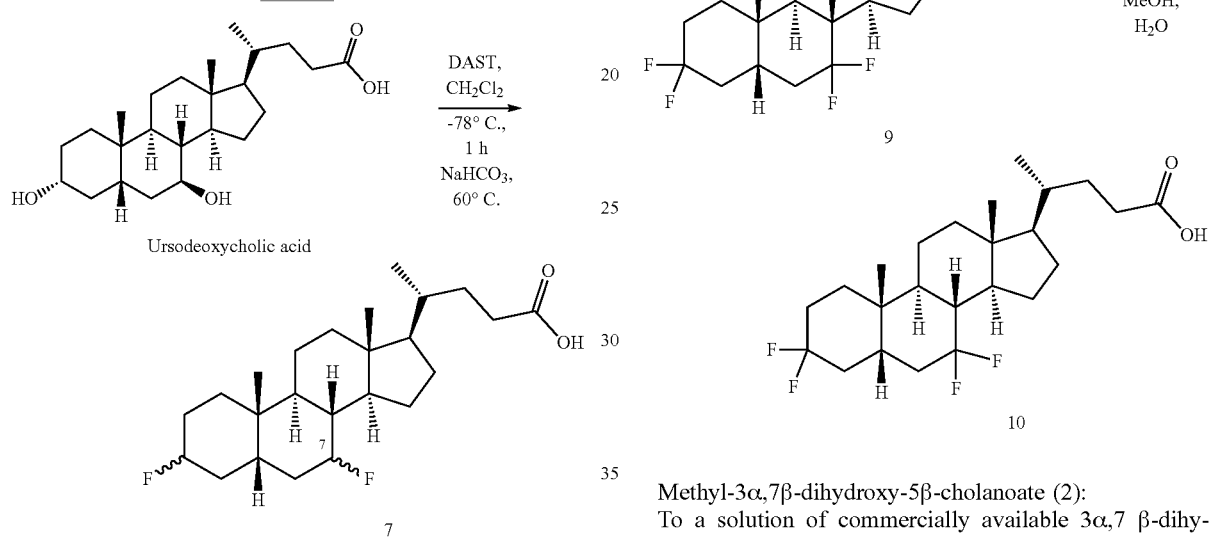

H-23b), 2.00-0.81 (m, 31H), 0.66 (s, 3H, CH$_3$-18). $^{13}$C-NMR (CDCl$_3$): 179.6 (C=O), 80.2 (CH), 71.5 (CH), 55.8 (CH), 55.7 (OCH$_3$), 55.0 (CH), 43.9 (CH), 43.8 (CH), 42.5 (CH), 41.4 (Cq), 40.2 (CH$_2$), 39.2 (CH), 37.0 (CH$_2$), 35.4 (CH), 35.0 (CH$_2$), 33.73 (CH$_2$), 31.0 (CH$_2$), 28.7 (CH$_2$), 27.0 (CH$_2$), 26.7 (CH$_2$), 23.5 (CH$_3$), 22.74 (Cq), 21.3 (CH$_2$), 18.5 (CH$_3$), 14.5 (Cq), 12.2 (CH$_3$), 11.6 (Cq).

Example 5: Synthesis of (R)-4-((3R,5S,7R,8R,9S,10S,12S,13R,14S,17R)-3,7,12-Trimethoxy-10,13-Dimethylhexadecahydro-1H-Cyclopenta[a]Phenanthren-17-Yl)Pentanoic Acid Method 1

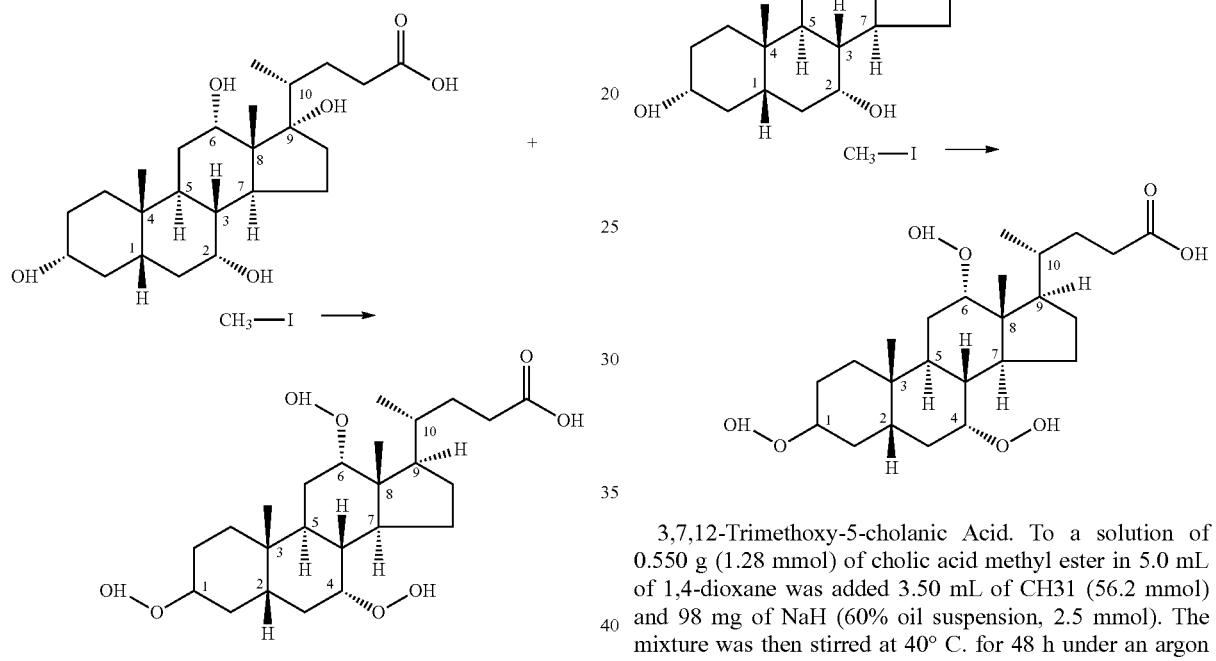

To a suspension of NaH (2.523 g of a 60% suspension in mineral oil, 63.09 mmol) in 100 mL of dry tetrahydrofuran at 0° C., was added via cannula a solution of commercially available cholic acid (5.035 g, 12.30 mmol) in 50 mL of dry tetrahydrofuran. The resulting solution was stirred at 0° C. for 10 min. and then was added methyl iodide (1.8 mL, 4.104 g, 28.91 mmol). The reaction mixture was stirred for 18 h at ambient temperature and then was added a second portion of NaH (2.054 g, 51.36 mmol), followed by more methyl iodide (1.5 mL, 3.42 g, 24.10 mmol). The reaction was stirred for an additional 18 h at ambient temperature. The reaction mixture was quenched by slow addition of methanol then concentrated using rotary evaporation. The resulting mixture was diluted with ethyl acetate (50 mL) and poured on water (40 mL). The aqueous layer was then extracted with ethyl acetate (3×25 mL). The combined organics were washed with brine (25 mL), dried over Na2SO4 and filtered. The solvent was then removed by rotary evaporation and the product was suspended over silica gel. Flash column chromatography purification (3:1 to 1:2hexanes/AcOEt gradient) yielded per methylated cholic acid (S4). (S4), white solid(3.423 g) in 62% yield m.p. 65-70° C.; 1H NMR (400 MHz; CDCl3): 3.35 (s, 1H), 3.33 (s, 3H), 3.25 (s, 3H), 3.20 (s, 3H), 3.13 (s, TH), 3.00 (t, J=11.0 Hz, 1H), 2.40 (td, J=12.7,4.1 Hz, 1H), 2.26-2.02 (m, 4H), 1.90-1.75 (m, 8H), 1.57-1.30 (m, 9H), 1.06-0.92 (m, 5H), 0.90 (d, J=6.1 Hz, 7H), 0.65 (s, 3H). 13C NMR (101 MHz; CDCl$_3$): 180.1, 82.1, 80.9, 77.1, 55.98, 55.82, 55.5, 46.41, 46.27, 42.8, 42.1, 39.8, 35.4, 35.20, 35.05, 34.5, 31.08, 30.88, 28.1, 27.9, 27.5, 26.8, 23.3,23.0, 22.1, 17.5, 12.6. IR (CDCl3): 3500-2480, 2930, 2870, 2820, 1708, 1454, 1371, 1102, 756 cm$^{-1}$.

Method 2 2-Step Reaction:

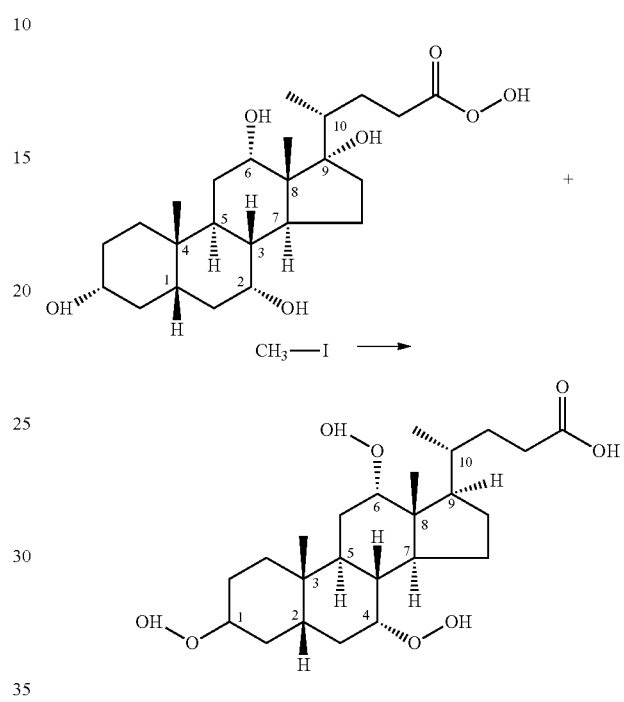

3,7,12-Trimethoxy-5-cholanic Acid. To a solution of 0.550 g (1.28 mmol) of cholic acid methyl ester in 5.0 mL of 1,4-dioxane was added 3.50 mL of CH31 (56.2 mmol) and 98 mg of NaH (60% oil suspension, 2.5 mmol). The mixture was then stirred at 40° C. for 48 h under an argon atmosphere. An additional 0.100 g of NaH (60% oil suspension) (2.5 mmol) was then added and the mixture allowed to stir for 24 h at 40° C. Additional NaH was added in the same manner three additional times for a total of 0.4 g (10 mmol), over the course of 120 h. The product mixture was then diluted by adding 100 mL of CH$_2$Cl$_2$ and washed with 50 mL of 1 M HCl and 2×50 mL of H$_2$O. After concentration under reduced pressure, the crude product mixture (0.820 g) was purified by column chromatography (SiO$_2$, CHCl$_3$/CH$_3$OH; 30/1, v/v) and then preparative thin-layer chromatography (SiO$_2$, CHCl$_3$/acetone, 20/1, v/v) to give 0.321 g (53%) of the title compound. R$_f$ 0.55; 1H NMR (CDCl3): 3.65 (s, 3H), 3.34 (bs, 1H), 3.31 (s, 3H), 3.23 (s, 3H), 3.19 (s, 3H), 3.12 (d, 1H), 2.96 (m, 1H), 0.86-2.35 (m, 30H), 0.64 (s, 3H).

To a solution of 321 mg (0.692 mmol) of 3,7,12-trimethoxy-5-cholanic acid, methylester in 14 mL of 1,4-dioxane was added 5.0 mL of a methanolic solution of 0.300 g (7.5 mmol) of NaOH, and the mixture was stirred at 45° C. for 2 h. The product mixtures was concentrated under reduced pressure, and the crude product was dissolved in 50 mL of CH$_2$Cl$_2$. This solution was then washed, sequentially, with 20 mL of 1 M HCl and 2×20 mL of H$_2$O, and the product was then purified by column chromatography (SiO$_2$, CHCl$_3$/MeOH; 10/1, v/v) to give 199 mg (63%) of the desired acid having. R$_f$=0.52; $^1$H NMR (CDCl3): 3.33 (bs, 1H), 3.29 (s, 3H), 3.22 (s, 3H), 3.18 (s, 3H), 3.11 (d, 1 H), 2.96 (m, 1H), 0.86-2.35 (m, 30H), 0.65 (s, 3H).

Cytotoxicity Assay

Example 4: Cell Culture and Treatments

General Method

Primary rat hepatocytes were isolated from male rats (100-150 g) by collagenase perfusion (Solá S, Ma X, Castro R E, Kren B T, Steer C J, Rodrigues C M P. *Ursodeoxycholic acid modulates E2F-1 and p53 expression through a caspase-independent mechanism in TGF-β1-induced apoptosis of rat hepatocytes. Journal of Biological Chemistry* 2003; 278: 48831-48838). Briefly, rats were anesthetized with phenobarbital sodium (100 mg/kg body weight) injected into the peritoneal cavity. After administration of heparin (200 units/kg body weight) in the tail vein, the abdomen was opened and the portal vein exposed and cannulated. The liver was then perfused at 37° C. in situ with a calcium-free Hanks' Balanced Salt Solution (HBSS) for~10 min, and then with 0.05% collagenase type IV in calcium-present HBSS for another 10 min.

Hepatocyte suspensions were obtained by passing collagenase-digested livers through 125 μm gauze and washing cells in Complete William's E medium (William's E medium, Sigma-Aldrich Corp., St Louis, MO, USA) supplemented with 26 mM sodium bicarbonate, 23 mM HEPES, 0.01 units/mL insulin, 2 mM L-glutamine, 10 nM dexamethasone, 100 units/mL penicillin, and 10% heat-inactivated fetal bovine serum (Invitrogen Corp., Carlsbad, CA, USA). Viable primary rat hepatocytes were enriched by low-speed centrifugation at 200 g for 3 min. Cell viability was determined by trypan blue exclusion and was typically 80-85%. After isolation, hepatocytes were ressuspended in Complete William's E medium and plated on Primaria™ tissue culture dishes (BD Biosciences, San Jose, CA, USA) at 5×104 cells/cm2.

Cells were maintained at 37° C. in a humidified atmosphere of 5% CO2 for 6 h, to allow attachment. Plates were then washed with medium to remove dead cells and incubated in Complete William's E medium supplemented with either 10-400 μM UDCA (Sigma-Aldrich Corp.), newly synthesized methylated UDCA, or no addition (control).

One hour or 12 h after pre-incubation, cells were exposed to 50 μM DCA (Sigma-Aldrich Corp.) for 40 h, or to 1 nM recombinant human TGF-β1 (R&D Systems Inc., Minneapolis, MN, USA) for 36 h before processing for cell viability and cytotoxicity assays.

Cell Viability, Cytotoxicity

General cell death or cytotoxicity was evaluated using the lactate dehydrogenase (LDH) Cytotoxicity Detection KitPLUS (Roche Diagnostics GmbH, Mannheim, Germany), following the manufacturer's instructions. Briefly, cell culture supernatants were combined in microplates with lactate (substrate), tetrazolium salt (coloring solution), and NAD (cofactor), previously mixed equitably according to the protocol. Plates were protected from light and incubated for at least 5 min at room temperature. Finally, absorbance was measured at 490 nm, with 620 nm as reference, using a Bio-Rad model 680 microplate reader (Bio-Rad Laboratories, Hercules, CA, USA).

General cell death was also determined using a bioluminescent cytolysis assay, designed to measure the release of adenylate kinase (AK) enzyme from damaged cells (ToxiLight™ BioAssay Kit, Lonza). Finally, cell viability was determined using the CellTiter-Fluor™ Cell Viability Assay (Promega Corp., Madison, WI, USA), according to the manufacturer's protocol, and further confirmed by the proliferation assay using 3-(4,5-dimethylthiazol-2-yl)-5-(3-carboxymethoxyphenyl)-2-(4-sulfophenyl)-2H-tetrazolium, inner salt (MTS) and an electron coupling reagent (phenazine methosulfate; PMS). MTS is bioreduced by cells into a formazan product that is soluble in tissue culture medium. The absorbance of the formazan at 490 nm can be measured directly from 96-well assay plates without additional processing. The conversion of MTS into aqueous, soluble formazan is accomplished by dehydrogenase enzymes found in metabolically active cells. The quantity of formazan product as measured by the amount of 490 nm absorbance is directly proportional to the number of living cells in culture.

Statistical Analysis

Statistical analysis was performed using GraphPad InStat version 3.00 (GraphPad Software, San Diego, CA, USA) for the analysis of variance and Bonferroni's multiple comparison tests. Values of $p<0.05$ were considered significant.

Results

We tested cell viability and cytotoxicity effects of newly synthesized methylated UDCA, using primary cultures of rat hepatocytes. The results showed that cytotoxicity of UDCA and methylated UDCA remained largely unchanged for concentrations up to 100 μM. Interestingly, methylated UDCA tended to increase cell viability from 10 to 100 μM concentrations, with no relevant signs of cytotoxicity. In contrast, an increase in cytotoxicity was evident for 200 and 400 μM concentrations of both UDCA and methylated UDCA, consistent with decreased viability at the highest bile acid concentrations.

We have previously shown that UDCA significantly inhibits DCA-induced cell death by ~60% (Castro R, Amaral J D, Sola S, Kren B T, Steer C J, Rodrigues C M P. Differential regulation of cyclin D1 and cell death by bile acids in primary rat hepatocytes. *American Journal of Physiology Gastrointestinal Liver Physiology* 2007; 293: G327-G334) and TGF-β1-induced cell death by ~50% (Solá et al., 2003) in primary rat hepatocytes. In dissecting the cytoprotective potential of methylated UDCA, we tested its ability to prevent DCA-induced cytotoxicity, as compared with UDCA.

Figure 4:
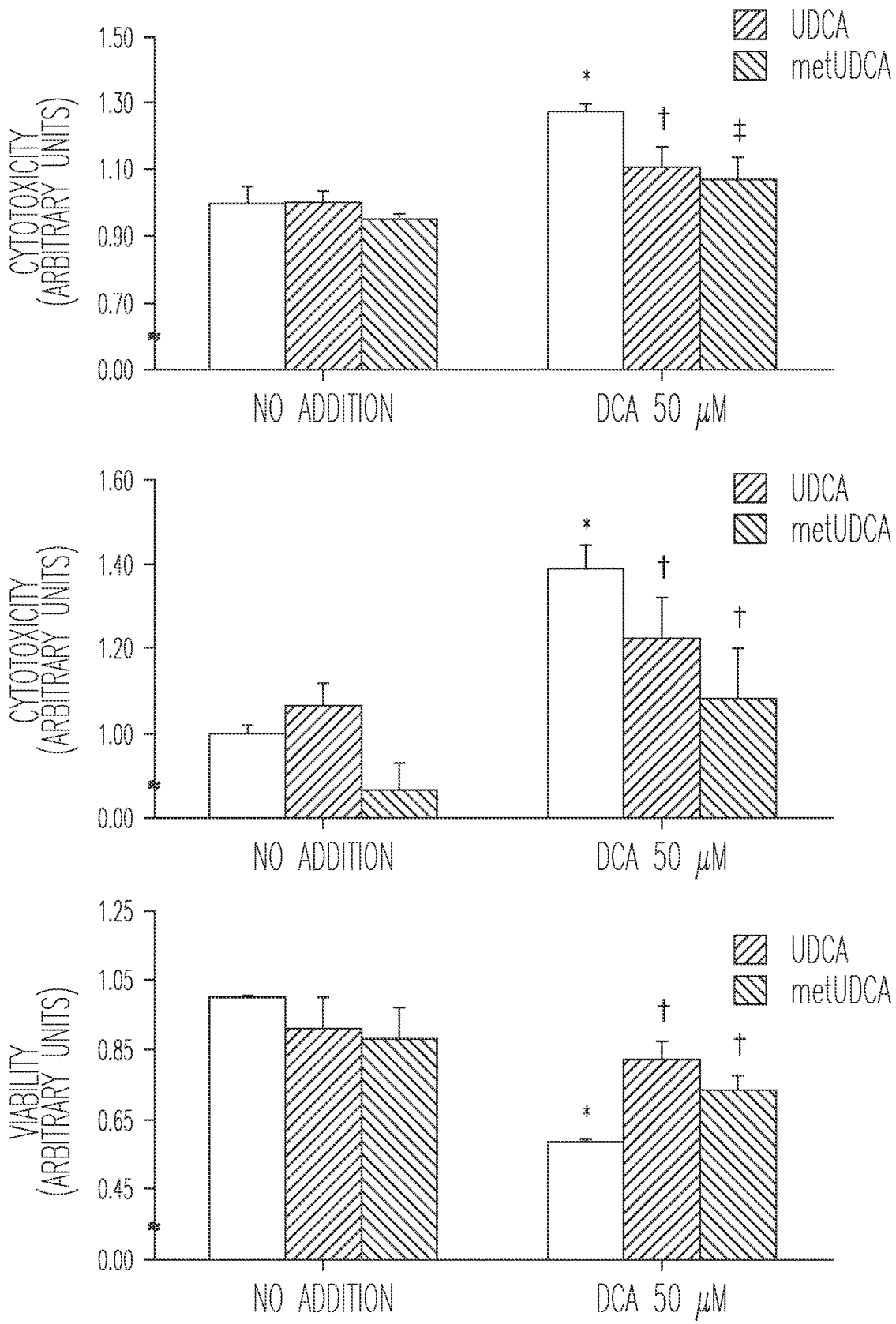
Figure 5:
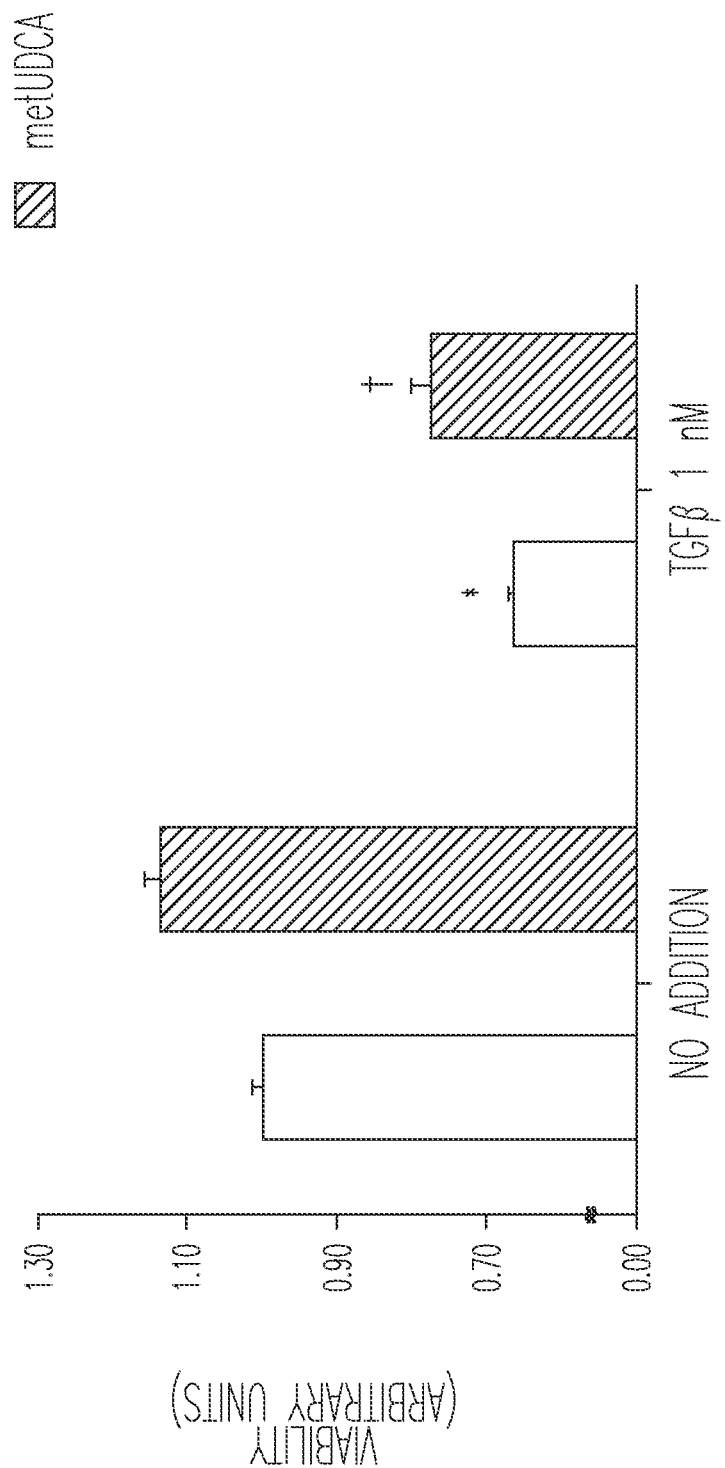
FIG. 5. Methylated UDCA prevents TGF-β1-induced loss of cell viability in primary rat hepatocytes. Primary rat hepatocytes were pre-incubated with 100 μM methylated UDCA, or no addition (control) for 12 h. Cells were then exposed to 1 nM TGF-β1 for 36 h before processing for MTS activity. Results are expressed as means±SEM of at least three experiments. *$p<0.01$ from control; †$p<0.05$ from TGF-β1.

UDCA and methylated UDCA at 100 μM concentrations inhibited 50 μM DCA-induced LDH release by ~70%, (FIG. 5, top). This protective effect was similar for methylated UDCA as compared to UDCA. Similar results were obtained using the ToxiLight Assay, although slightly better protection was obtained for methylated UDCA in cells exposed to 50 μM DCA (FIG. 4, middle). Similarly, both UDCA and its methylated derivative pretreatment were effective at rescuing cell viability in cells exposed to 50 μM DCA (FIG. 4, bottom).

Finally, in cells exposed to a stimulus unrelated to bile acids, such as TGF-β1, methylated UDCA was effective at inhibiting TGF-β1-induced reduction in MTT metabolism, which in turn was comparable to previously reported UDCA effects (FIG. 3).

The results show that the newly synthesized methylated UDCA displays cytoprotective and cell death inhibitory properties in vitro that are comparable to those of parent UDCA molecule.

The above Detailed Description includes references to the accompanying drawings, which form a part of the Detailed Description. The drawings and descriptions show, by way of illustration, specific embodiments in which the present disclosed prodrugs and related methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "including" and "comprising" are open-ended, that is, an assembly, system, or method that includes elements in addition to those listed after such a term in a claim are still deemed to fall within the scope of that claim. Moreover, in the following claims, the terms "first," "second," and "third," etc., if used, are merely used as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

It will be understood from the Detailed Description, that the present subject matter can be implemented in a multitude of different sizes, shapes, fit and function embodiments. While described in the context of a synthesized, water-soluble prodrug compound, it will be apparent to those skilled in the art that the present disclosure could be used in a number of varying applications.

The invention claimed is:
1. A compound selected from the following table:

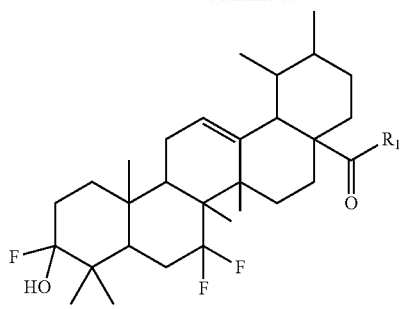

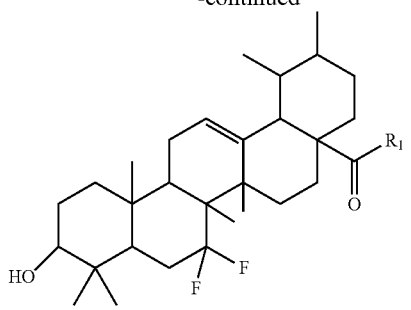

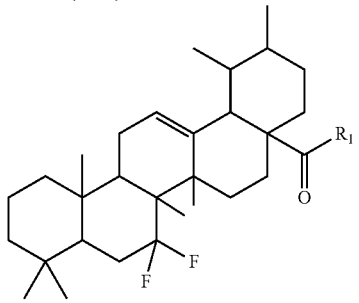

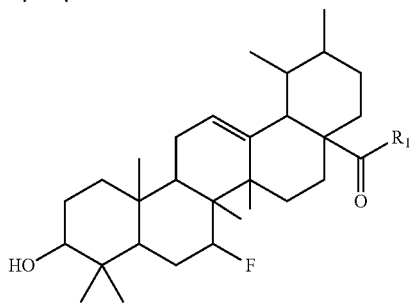

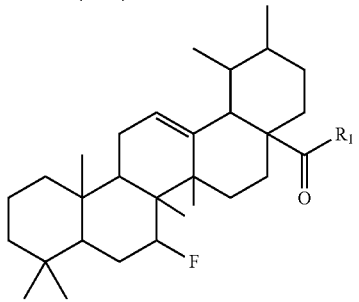

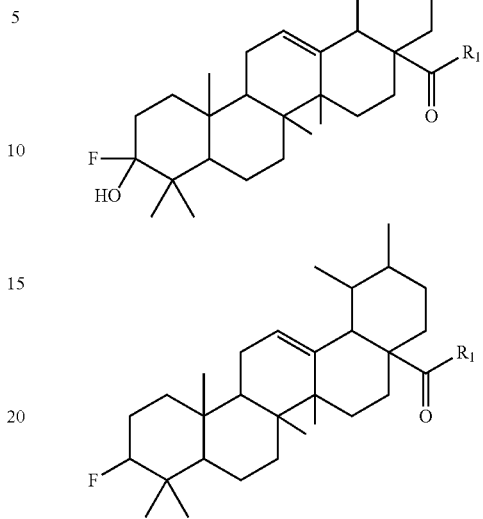

wherein $R_1$ is —OH, —O—(CH$_2$)—O—P(O)(OH)$_2$, —OP(O)(OH)$_2$, or —F;

or a pharmaceutically acceptable salt thereof.

2. A method of treating or preventing a disease that is selected from the group consisting of neurological disease, diabetes, ocular disorders, spinal cord injury, kidney injury or metabolic syndrome in a subject, said method comprising administering to said subject a therapeutically effective amount of a compound according to claim 1.

3. The method according to claim 2, wherein the disease is a neurological disease selected from the group consisting of Alzheimer's, Parkinson's, Huntington's, and amyotrophic lateral sclerosis (ALS).

4. The method according to claim 2, wherein the disease is type 2 diabetes.

5. The method according to claim 2, wherein the disease is acute kidney injury.

6. The method according to claim 2, wherein the disease is an ocular disorder selected from macular degeneration (MD) and diabetic retinopathy.

* * * * *